(12) United States Patent
Kellenberger et al.

(10) Patent No.: US 8,445,451 B2
(45) Date of Patent: *May 21, 2013

(54) MACROLIDES AND USES OF MACROLIDES

(75) Inventors: Johannes Laurenz Kellenberger, Riehen (CH); Jürg Dreier, Witterswil (CH); Stefan Bernhard Reinelt, Weil am Rhein (DE)

(73) Assignee: Basilea Pharmaceutica AG, Basel (CH)

( * ) Notice: Subject to any disclaimer, the term of this patent is extended or adjusted under 35 U.S.C. 154(b) by 47 days.

This patent is subject to a terminal disclaimer.

(21) Appl. No.: 12/865,948

(22) PCT Filed: Feb. 9, 2009

(86) PCT No.: PCT/EP2009/051457
§ 371 (c)(1),
(2), (4) Date: Sep. 20, 2010

(87) PCT Pub. No.: WO2009/098320
PCT Pub. Date: Aug. 13, 2009

(65) Prior Publication Data
US 2011/0021449 A1    Jan. 27, 2011

(30) Foreign Application Priority Data
Feb. 8, 2008 (EP) .................... 08101444

(51) Int. Cl.
*A61K 31/70* (2006.01)
*C07H 17/08* (2006.01)
(52) U.S. Cl.
USPC ................. 514/29; 536/7.2; 536/7.3; 536/7.4
(58) Field of Classification Search
USPC ............................ 536/7.2, 7.3, 7.4
See application file for complete search history.

(56) References Cited

U.S. PATENT DOCUMENTS

| | | | | |
|---|---|---|---|---|
| 6,395,710 B1* | 5/2002 | Chu et al. | | 514/29 |
| 6,720,308 B1 | 4/2004 | Vo | | |
| 7,414,030 B2* | 8/2008 | Vo et al. | | 514/29 |
| 7,524,823 B2* | 4/2009 | Kellenberger et al. | | 514/29 |
| 2004/0038915 A1 | 2/2004 | Vo | | |

FOREIGN PATENT DOCUMENTS

| | | |
|---|---|---|
| EP | 1439186 | 7/2004 |
| WO | 0216380 | 2/2002 |
| WO | 03072588 | 9/2003 |
| WO | 2006084410 | 8/2006 |
| WO | 2008017696 | 2/2008 |
| WO | 2009106419 | 9/2009 |

OTHER PUBLICATIONS

The International Search Report and Written Opinion by the International Searching Authority, issued on Sep. 30, 2009, in the PCT application No. PCT/EP2009/051457.

D4. Hunziker et al., "Novel ketolide antibiotics with a fused five-membered lactone ring-synthesis, physicochemical and antimicrobial properties," Bioorg Med Chem. Jul. 1, 2004;12(13):3503-19.

McEwan et al., "Chemoresistant KM12C Colon Cancer Cells Are Addicted to Low Cyclic AMP Levels in a Phosphodiesterase 4—Regulated Compartment via Effects on Phosphoinositide 3-Kinase," Cancer Res 2007; 67: (11). Jun. 1, 2007.

Odingo, "Inhibitors of PDE4: a review of recent patent literature," Expert Opinion on Therapeutic Patents, Jul. 2005, vol. 15, No. 7 , pp. 773-787.

Hendrix et al., "9 Phosphodiesterase Inhibitors: A Chemogenomic View," Chemogenomics in Drug Discovery: A Medicinal Chemistry Perspective, Oct. 2004, pp. 243-288.

Tanikawa et al., "Synthesis and antibacterial activity of a novel series of acylides: 3-O-(3-pyridyl)acetylerythromycin A derivatives," J Med Chem. Jun. 19, 2003;46(13):2706-15.

Labro, "Anti-inflammatory activity of macrolides: a new therapeutic potential?" Journal of Antimicrobial Chemotherapy vol. 41, Issuesuppl 2 pp. 37-46, (1998).

Mereu et al., "Design, synthesis and in vivo activity of 9-(S)-dihydroerythromycin derivatives as potent anti-inflammatory agents," Bioorganic & Medicinal Chemistry Letters 16 (2006) 5801-5804.

(Continued)

*Primary Examiner* — Elli Peselev

(57) ABSTRACT

Macrolides of Formula (I) or (I-A): and wherein the residues R1, R2, R3, R4, R12, R13 and R14 have certain meanings defined in this application are useful for treating or preventing inflammatory or allergic diseases or, cancer in animals and humans.

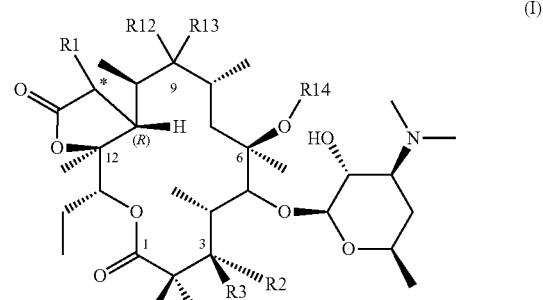

(I)

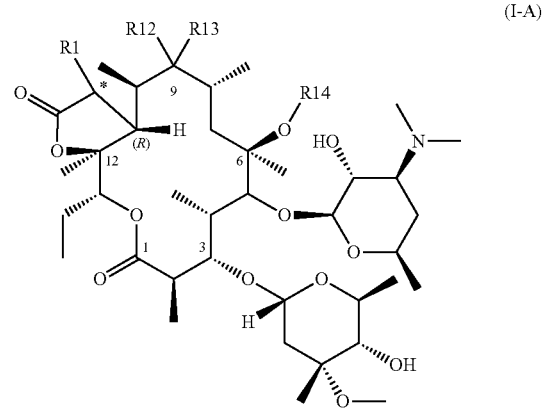

(I-A)

28 Claims, No Drawings

OTHER PUBLICATIONS

Lipworth, "Phosphodiesterase-4 inhibitors for asthma and chronic obstructive pulmonary disease," The Lancet, vol. 365, Issue 9454, pp. 167-175.

Giembycz, "Life after PDE4: overcoming adverse events with dual-specificity phosphodiesterase inhibitors," Curr Opin Pharmacol. Jun. 2005;5(3):238-44.

Baker et al., "Modification of macrolide antibiotics. Synthesis of 11-deoxy-11-(carboxyamino)-6-O-methylerythromycin A 11,12-(cyclic esters) via an intramolecular Michael reaction of O-carbamates with an alpha,beta-unsaturated ketone," J. Org. Chem., 1988, 53 (10), pp. 2340-2345.

Kashimura et al., "Synthesis and Antibacterial Activity of the Tricyclic Ketolides TE-802 and Its Analogs," J. Antibiot., vol. 54;No. 8; pp. 664-678(2001).

Han et al., "A Soluble Polymer-Bound Approach to the Sharpless Catalytic Asymmetric Dihydroxylation (AD) Reaction: Preparation and Application of a [(DHQD)zPHAL.PEG-OMe] Ligand," Tetrahedron Letters, vol. 38, No. 9, pp. 1527-1530, 1997.

Elliott et al., "Anhydrolide Macrolides. 1. Synthesis and Antibacterial Activity of 2,3-Anhydro-6-O-methyl 11,12-Carbamate Erythromycin A Analogues," J. Med. Chem., 1998, 41 (10), pp. 1651-1659.

Agouridas et al., "Synthesis and antibacterial activity of ketolides (6-O-methyl-3-oxoerythromycin derivatives): a new class of antibacterials highly potent against macrolide-resistant and -susceptible respiratory pathogens," J. Med. Chem. Oct. 8, 1998;41(21):4080-100.

Torphy et al., "Stimulation of beta adrenoceptors in a human monocyte cell line (U937) up-regulates cyclic AMP-specific phosphodiesterase activity," JPET Dec. 1992 vol. 263 No. 3, pp. 1195-1205.

The Communication about intention to grant a European patent from the European Patent Office, issued on Sep. 4, 2012, in the European Application No. 09707590.7.

* cited by examiner

MACROLIDES AND USES OF MACROLIDES

This application is a National Stage Application of PCT/EP2009/051457, filed Feb. 9, 2009, which claims priority from European Patent Application 08101444.1 filed on Feb. 8, 2008. The priority of both said PCT and European Patent Application is claimed.

The invention relates to the treatment and/or prevention of inflammatory and allergic diseases and diseases associated with uncontrolled cellular growth, proliferation and/or survival in animals or humans, e.g. cancer, by use of certain macrolide compounds and pharmaceutical compositions containing said compounds. The invention relates furthermore to macrolide compounds with anti-inflammatory, anti-allergic and anti-cancer activity in the aforementioned sense mediated through inhibition of phosphodiesterases, in particular, phosphodiesterase 4 (PDE4), making these compounds useful for the treatment and/or prevention of diseases such as chronic obstructive pulmonary disease (COPD), asthma, rheumatoid arthritis, atopic dermatitis or inflammatory bowel disease, cancer diseases and other diseases.

Cyclic adenosine monophosphate (cAMP) is a key second messenger in cells. Increased levels of cyclic AMP are known to suppress cellular responses in various types of inflammatory and immune cells including lymphocytes, monocytes, macrophages, neutrophils, eosinophils, basophils and lung epithelial cells. Intracellular concentrations of cAMP are regulated by adenylyl cyclase and by cyclic nucleotide phosphodiesterases (PDEs). PDEs are a family of enzymes that inactivate cyclic nucleotides cAMP and cGMP through hydrolysis to AMP and GMP. The cAMP-specific enzyme PDE4 is the predominant enzyme in pro-inflammatory cells. PDE4 has been shown to be involved in inflammatory processes (cf. e.g. Lipworth B. J., Lancet (2005) 365, p. 167 or Giembycz M. A., Curr. Opin. Pharmacol. (2005), 5, p. 238). Therefore, inhibitors of PDE4 are useful in the treatment and/or prophylaxis of inflammatory and allergic diseases such as asthma, chronic bronchitis, emphysema, atopic dermatitis, urticaria allergic rhinitis, allergic conjunctivitis, psoriasis, rheumatoid arthritis, chronic obstructive pulmonary disease (COPD), septic shock, ulcerative colitis, Crohn's disease, adult respiratory distress syndrome and multiple sclerosis. PDE4 inhibitors are also potentially useful for the treatment of cancer diseases as indicated e.g. by D. G. McEwan et al. in "Chemoresistant KM12C Colon Cancer Cells Are Addicted to Low Cyclic AMP Levels in a Phosphodiesterase 4-Regulated Compartment via Effects on Phosphoinositide 3-Kinase", Cancer Res. 2007; 67(11); Jun. 1, 2007.

Numerous PDE4 inhibitors have been disclosed in the literature. (see for example J. O. Odingo, Expert. Opin. Ther. Patents, 2005, 15(7), 773; M. Hendrix, C. Kallus, Methods and Principles in Medicinal Chemistry (2004), Vol. 22 (Chemogenomics in Drug Discovery), 243-288 (Wiley-VCH)). Many of the known PDE4 inhibitors show dose-limiting side-effects such emesis and headache. Among the most advanced PDE4 inhibitors are roflumilast and cilomilast.

Erythromycin derivatives having a thio-substituted, five-membered lactone ring fused to the 11,12-positions of the macrolactone ring have been disclosed in e.g. WO 02/16380, WO 03/072588, WO2006/084410, U.S. Pat. No. 0,038,915 and in U.S. Pat. No. 6,720,308. Documents WO 02/16380, WO 03/072588 and U.S. Pat. No. 0,038,915 describe so-called ketolides having a carbonyl group at position 3 of the erythromycin scaffold. Document U.S. Pat. No. 6,720,308 describes so-called anhydrolides. Document WO2006/084410 describes compounds with a cladinose moiety attached to position 3 of the macrolide. Compounds with a hydroxyl group in position 3 of the erythromycin scaffold are found as intermediates in the synthesis of the final compounds. Formation of 3-acyl-derivatives is described in e.g. J. Med. Chem. 2003, 46, 2706.

All macrolide compounds described in the above-mentioned documents have been disclosed as useful for the treatment of bacterial infections. Erythromycin-derived macrolides have also been reported to possess anti-inflammatory activity (e.g. Journal of Antimicrobial Chemotherapy, 1998, 41, Suppl. B, 37-46; Bioorg. Med. Chem. Lett., 2006, 16, p5801). Furthermore, erythromycin-derived macrolides are known to accumulate in inflammatory cells.

Surprisingly, it has now been found that certain macrolide compounds having a five-membered lactone ring fused to the erythromycin scaffold and being substituted with specific side chains selectively inhibit PDE4, a newly found activity not available to the public so far for this kind of molecules. These macrolides are therefore useful for the prevention and/or treatment of inflammatory diseases, the prevention and/or treatment of allergic diseases or for the prevention and/or treatment of cancer, in animals or particularly in humans. The molecules described herein are structurally distinct to currently known PDE4 inhibitors and therefore have, in particular, the potential to overcome the above-mentioned side effects of the known PDE4 inhibitors.

Some of the macrolides found are novel. In one aspect therefore the present invention accordingly relates to macrolide compounds of formula (I)

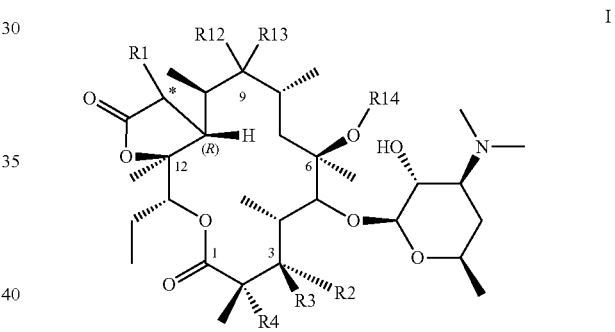

wherein
R1 is a residue —Y—X-Q;
Y is S, SO or $SO_2$;
X is a bond or a linear group consisting of hydrogen atoms and 1 to 9 atoms selected from C, N, O and/or S, of which up to 2 atoms can be N and one atom can be O or S, one carbon atom can appear as a CO group and the sulphur atom can appear as an $SO_2$ group and two adjacent C atoms can be present as —CH═CH— or —C≡C— and which group X is unsubstituted or is substituted with —COO—W or —CONH—W;
Q is a residue —V-A1-L-A2-W or, if X does not represent a bond, may also be —NR6R7;
V is a optionally substituted divalent aromatic or heterocyclic group;
W is optionally substituted aryl or heterocyclyl; or in a group —V-A1-L-A2-W, wherein at least one of the groups A1, L or A2 is present, can also be a monovalent substituted or unsubstituted, saturated or unsaturated linear group with up to 5 atoms consisting of C, N, O and/or S of which one carbon can appear as a CO group one sulphur atom can appear as an $SO_2$ group,
A1 and A2 are, independently of each other, either absent or a $C_1$-$C_4$alkylene group;
L is a single bond, —O—, —S—, —$SO_2$—, —NH—, —CO—, —(CO)O—, —O(OC)—, —(CO)NH—, —NH (CO)—, —(SO₂)NH—, —HN(SO₂)—, —HN(CO)NH—, —O(CO)NH—, —HN(CO)O—, or can also be absent if A1 and/or A2 are present;

R2 is OR2a and

R3 is hydrogen or

R2 and R3 taken together with the carbon atom to which they are linked, represent a C=O group;

R2a is hydrogen, acetyl, —(C=O)CH2NR2bR2c, or —(C=O)CH2CH2NR2bR2c;

R2b and R2c are, independently of each other, hydrogen or C1-C6 alkyl which can be substituted or unsubstituted, and where up to two atoms can be N, O or S and one carbon atom can appear as C=O or taken together with the nitrogen atom to which they are linked form a 4-7 membered-ring of which up to two atoms can be N, O or S and one carbon can appear as C=O;

R4 is hydrogen or

R2 and R4 taken together with the bond between the carbon atoms to which they are linked, form a double bond;

R6 and R7 are independently of each other selected from hydrogen, methyl; from optionally substituted aryl; aralkyl; heterocyclyl and heterocyclylalkyl; and one of R6 and R7 can also be a group -L-A2-W;

R12 is hydrogen and

R13 is OR14 or

R12 and R13, taken together with the carbon atom to which they are linked, represent a C=O group;

R14 is, independently at each occurrence in formula I, hydrogen or a saturated or unsaturated aliphatic group with 1 to 6 carbon atoms; and \* indicates a chiral centre which is in the (R) or (S) form.

In a more specific aspect the present invention relates to macrolides of formula (I) for use in the treatment of diseases and disorders in animals or humans which can be ameliorated or relieved by inhibition of phosphodiesterases, in particular phosphodiesterase 4 (PDE4).

Furthermore, the present invention relates compounds of said formula (I) for use for the prevention and/or treatment of inflammatory diseases in animals or humans, the prevention and/or treatment of allergic diseases in animals or humans or for the prevention and/or treatment of cancer in animals or humans.

The compounds of formula (I) are particularly preferred for use for the prevention and/or treatment of cancer in animals or humans. Use for the treatment of cancer is preferred.

The invention furthermore relates to macrolides compound of formula (I-A)

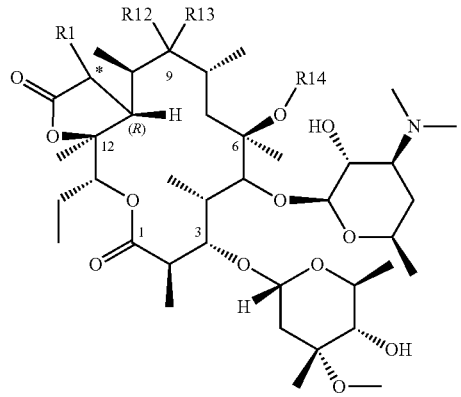

I-A wherein

R1 is a residue —Y—X-Q;

Y is S, SO or SO₂;

X is a bond or a linear group consisting of hydrogen atoms and with up to 9 atoms selected from C, N, O and/or S, of which up to 2 atoms can be N and one atom can be O or S, one carbon atom can appear as a CO group and the sulphur atom can appear as an SO₂ group and two adjacent C atoms can be present as —CH=CH— or —C≡C— and which group X is unsubstituted or is substituted with —COO—W or —CONH—W;

Q is a residue —V-A1-L-A2-W or, if X does not represent a bond, may also be —NR6R7;

V is an optionally substituted divalent aromatic or heterocyclic group;

W is optionally substituted aryl or heterocyclyl; or in a group —V-A1-L-A2-W, wherein at least one of the groups A1; L or A2 is present, can also be a monovalent substituted or unsubstituted, saturated or unsaturated linear group with up to 5 atoms consisting of C, N, O and/or S of which one carbon can appear as a CO group one sulphur atom can appear as an SO₂ group, A1 and A2 are independently of each other either absent or a C₁-C₄alkylene group;

L is a single bond, —O—, —S—, —SO₂—, —NH—, —CO—, —(CO)O—, —O(OC)—, —(CO)NH—, —NH(CO)—, —(SO₂)NH—, —HN(SO₂)—, —HN(CO)NH—, —O(CO)NH—, —NH(CO)O—, or can also be absent if A1 and/or A2 are present;

R6 and R7 are independently of each other selected from aryl; aralkyl; heterocyclyl and heterocyclylalkyl; and one of R6 and R7 can also be a group -L-W R12 is hydrogen and R13 is OR14 or R12 and R13 taken together with the carbon atom to which they are linked, represent a C=O group;

R14 is, independently at each occurrence in formula (I-A), hydrogen or a saturated or unsaturated aliphatic group with 1 to 6 carbon atoms; and \* indicates a chiral centre which is in the (R) or (S) form;

specifically for use for the prevention and/or treatment of cancer in animals or humans. Treatment of cancer is preferred.

The compounds of formula (I-A) and their use in the treatment of diseases and disorders in humans which can be ameliorated or relieved by inhibition, in particular of phosphodiesterase 4 (PDE4), and, based on this activity, their usefulness for the prevention and/or treatment of inflammatory diseases as well as for the treatment and/or prevention of allergic diseases, but not for the prevention and/or treatment of diseases associated with uncontrolled cellular growth, proliferation and/or survival, e.g. cancer, in animals or humans, has already been described in International Application No. PCT/EP2007/058247 filed by the present applicant on Aug. 8, 2007 and published as WO2008/017696.

For the purposes of the present invention the term "macrolide compound" is understood to include the separate stereomeric forms of the compounds as well as diastereomeric mixtures.

Furthermore, for the purposes of the present invention the term "macrolide compound", is understood to include pharmaceutically acceptable salts and N-oxides of the compounds of formula (I) or (I-A), as well as in vivo cleavable esters of said compounds.

The compounds of the invention exhibit substantial inhibitory activity towards phosphodiesterases (PDEs), in particular towards PDE4, which has been shown to be involved in inflammatory processes (cf. e.g. Lipworth B. J., Lancet (2005) 365, p. 167 or Giembycz M. A., Curr. Opin. Pharmacol. (2005), 5, p. 238). This is shown in the examples. The use of the compounds according to the present invention for the treatment of diseases and disorders in animals and particularly in humans which can be ameliorated or relieved by inhibition of phophodiesterases, in particular phosphodiesterase 4 (PDE4) is therefore one of the aspects of the present invention. Based on this activity the present compounds are particularly useful in subjects selected from animals, in particular mammals, and yet more preferred humans, for the prevention and/or treatment of inflammatory diseases as well as for the treatment and/or prevention of allergic diseases and for treatment of diseases associated with uncontrolled cellular growth, proliferation and/or survival.

Particularly important examples of such diseases e.g include chronic obstructive pulmonary disease (COPD), asthma, rheumatoid arthritis, atopic dermatitis or inflammatory bowel disease and diseases associated with uncontrolled cellular growth, proliferation and/or survival.

For the purposes of the present invention the terms "aromatic group" and "aryl" refer to aromatic groups with one or more preferably 6-membered nuclei and having from 6 to 14 carbon atoms. Examples are in particular phenyl, naphthyl, anthryl and phenanthryl. These groups may be further substituted with 1, 2, 3 or 4 substituents selected from, for example, alkyl such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as difluoromethyl or trifluoromethyl, trichloroethyl, halogen substituted alkoxy groups such as difluoromethoxy, cyano, nitro, amino, alkylamino, dialkylamino, alkylthio, mercapto, hydroxy, carbamoyl, a carboxyl group. In case more than one substituent is attached to the aryl group, these substituents can be identical or different from each other. Also encompassed by the scope of the present invention are different possible regioisomers (constitution isomers) of a specific group, for example "dimethoxy-phenyl" means that both methoxy substituents may be attached to the phenyl ring in the 2,3-position, the 2,4-position, the 2,5-position, the 2,6-position, the 3,4-position, the 3,5-position and the 3,6-position.

As used herein the term "heterocyclic group" or "heterocyclyl" refers to an unsaturated or saturated, unsubstituted or substituted 5- to 10-membered (mono- or bicyclic) heterocyclic ring system containing at least one hetero atom selected from the group consisting of sulfur, oxygen, and, preferably, nitrogen. Exemplary heterocyclic substituents include, but are not limited to, for example, the following groups: piperidinyl, morpholinyl, 2-, 3- or 4-pyridyl, pyrrolidinyl, piperazinyl, 1H-pyrazol-1-yl, 1H-imidazol-1-yl, 1H-imidazol-2-yl, pyrazinyl, pyrimidyl, pyridazinyl, pyrazolyl, triazinyl, thiazolyl, thiadiazolyl, oxadiazolyl, triazolyl, e.g. 1H-[1,2,4]-triazol-1-yl, 1H-tetrazolyl, 2H-tetrazolyl; thienyl, furyl (2-furanyl or 3-furanyl), 1H-azepinyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, oxazolidinyl, tetrahydrothienyl, and the like, or condensed heterocyclic ring systems such as quinolinyl, e.g. quinolin-8-yl, quinolin-5-yl, quinolin-2-yl, quinolin-6-yl, quinolin-3-yl, isoquinolinyl (6-isoquinolinyl), quinazolinyl, 1H-benztriazolyl, 1H-imidazo[4,5-c]pyridinyl, 5H-imidazo[4,5-c]pyridinyl, 1H-imidazo[4,5-b]pyridin-1-yl, 3H-imidazo[4,5-b]pyridin-3-yl, 1H-pyrazolo[3,4-b]pyridinyl, 1,2,3,4-tetrahydro-quinolinyl, 1,2,3,4-tetrahydro-isoquinolinyl, thieno[2,3-b]pyridinyl, benzothiazolyl (e.g. 2-benzothiazolyl), 1H-benzoimidazolyl, 1H-indolyl, 1,2,3,4-tetrahydroquinolinyl, purinyl, e.g. 9H-purin-9-yl, 6-amino-9H-purin-9-yl, 2,6-diamino-9H-purin-9-yl, 1H-purin-6-yl, 1H-2,3-dihydroindol-1-yl, 2,1,3-benzoxadiazol-5-yl, 2,1,3-benzoxadiazol-4-yl, 1,3-benzodioxol-5-yl, 2,3-benzoxazolinyl, 1,2-dihydro-oxazolo[5,4-c]pyridinyl, 6-quinoxalinyl, 2-benzo[b]thien-3-yl, 3,4-dihydro-1H-2-oxo-quinolin-6-yl.

The heterocyclyl groups may be further substituted by one or more substituents. Such substituents include, for example, alkyl groups such as defined hereinafter, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined hereinafter, halogen substituted alkyl groups such as trifluoromethyl, trichloroethyl, halogen substituted alkoxy groups such as difluoromethoxy, nitro, amino, alkylamino, dialkylamino, alkylthio, mercapto, hydroxy, carbamoyl, carboxyl, an oxo group. In case more than one substituent is attached to the heterocyclyl group, these substituents can be identical or different from each other. Different regioisomers are also included within the scope of the present definition, for example "dimethylpyridyl" means that both methyl substituents may be attached to the pyridyl at all chemically possible positions. For example both methyl substituents may be attached to the 2-pyridyl in the 3,4-position, the 4,5-position, the 5,6-position, the 3,5-position, the 3,6-position, and the 4,6-position. Both methyl substituents may be attached to the 3-pyridyl in the 2,4-position, the 2,5-position, the 2,6-position, the 4,5-position, the 4,6-position, and the 5,6-position. Both methyl substituents may be attached to the 4-pyridyl in the 2,3-position, the 2,5-position, the 2,6-position, and the 3,5-position.

Especially preferred substituents for the heterocyclyl groups are alkyl, alkoxy, oxo, halogen, amino, alkylamino or dialkylamino, wherein alkyl and alkoxy are as defined hereinabove.

Examples of preferred substituted heterocyclic rings are 1H-pyrimidin-2,4-dione, 1H,3H-pyrimidin-2,4-dione-5-methyl, 1H-pyrimidin-4-amino-2-on, 6-amino-9H-purin, 6-dimethylamino-9H-purin, 2,6-diamino-9H-purin, 6-amino-8-[(3-pyridinylmethyl)amino]-9H-purin, 4-amino-imidazo[4,5-c]pyridine, 4-methoxy-imidazo[4,5-c]pyridine, 1-ethyl-pyrazolo [3,4-b]pyridine, 4-phenyl-1H-pyrazol, 3-(pyridin-3-yl)-1H-pyrazol, 3-(pyridin-4-yl)-1H-pyrazol-1-yl, 3-(pyridin-3-yl)-1H-imidazol-1-yl, 3-(pyridin-4-yl)-1H-imidazol-1-yl, 3-(pyridin-3-yl)-1H-[1,2,4]triazol, 3-(pyridin-4-yl)-1H-[1,2,4]triazol and 2-oxo-1,2,3,4-tetrahydro-quinoline.

As used herein the term "alkyl" refers to branched or straight chain saturated hydrocarbon groups having preferably 1 to 6 carbon atoms. Such groups are for example methyl, ethyl, n-propyl, isopropyl, tertiary butyl, pentyl, hexyl, and the like. Such alkyl groups may be further substituted with one or more substituents selected from, for example, lower alkoxy such as $C_1$-$C_4$alkoxy like methoxy, ethoxy, propyloxy or n-butoxy, $C_3$-$C_7$cycloalkyloxy or $C_3$-$C_7$cycloalkyl-$C_1$-$C_4$alkoxy like cyclopentyloxy, cyclopropylmethyloxy, halogen such as defined below, halogen substituted alkyl groups such as difluoromethyl or trifluoromethyl, trichloroethyl, cyano, nitro, amino, alkylamino, dialkylamino, alkylthio, mercapto, hydroxy, carbamoyl, carboxyl, or oxo. If more than one substituent are present, then these substituents can be either identical or different from each other.

The term aliphatic group refers to branched or preferably straight chain hydrocarbon groups having preferably 1 to 6 carbon atoms, which can be saturated or unsaturated. Examples include those mentioned for alkyl, vinyl, n-propenyl, n-propinyl, butenyl groups, butadienyl, pentenyl groups, and the like.

The term "halogen" refers to fluorine, chlorine, bromine or iodine, preferably fluorine and chlorine.

In the combinations "heterocyclylalkyl" and "aralkyl" the single parts "heterocyclyl", "ar" (=aryl), and "alkyl" have the same meanings as indicated above.

The term $C_1$-$C_4$alkylene group refers e.g. to methylene, ethylene, n-propylene, iso-propylene or n-butylene.

R1 is a residue of formula —Y—X-Q.

In this formula Y may generally be S, SO or $SO_2$; preferred are S and $SO_2$, in particular S.

X is either a bond; i.e. is "absent", or a linear group consisting of hydrogen atoms and up to 9 atoms selected from C, N, O and/or S, of which up to 2 atoms can be N and one atom can be O or S, one carbon atom can appear as a CO group and the sulphur atom can appear as a $SO_2$ group. Two adjacent C atoms can also be present as —CH=CH— or —C≡C—. The group X can be unsubstituted or is substituted with a substituent of formula —COO—W or —CONH—W, wherein W has the meaning defined herein. As already indicated the spacer group X with up to 9 atoms may carry additional hydrogen atoms to saturate a C atom to form e.g. a methylene group or to saturate a N atom to form an amino group. Preferably, this spacer consists of 2 to 5 atoms selected from C, N, O and/or S.

Preferred groups X are:

$(CH_2)_n$, $(CH_2)_mOCH_2$, $(CH_2)_2NCH_3(CH_2)_2$, $CH_2CH_2NH$, $(CH_2)_pCOO$, $(CH_2)_pCONH$; $O(CH_2)_p$ or $HN(CH_2)_p$, where n and p are 1, 2 or 3 and m is 0 or preferably 1, 2 or 3 and which are linked with the group Y via a carbon atom.

Particularly preferred groups X are 1,2-ethylene, n-propylene or iso-propylene and $O(CH_2)_p$ or $HN(CH_2)_p$, where p is 2 or 3, preferably 2.

Suitable combinations of Y and X are e.g as follows:

For Y=S, X is 1,2-ethylene, 1,2- and 1,3-propylene, $CH_2CO$, $CH_2COCH_2$, $CH_2CONR$, $CH_2CONRCH_2$, $CH_2CONRCH_2CH_2$, $CH_2CH_2O$, $CH_2CH_2CONR$, $CH_2CH_2CONRCH_2$, $CH_2CH_2NR$, $CH_2CH_2NRCO$, $CH_2CH_2NRSO_2$, $CH_2CH_2NRCOO$, $CH_2CH_2OCH_2$, $CH_2SO_2NR$, $CH_2SO_2NRCH_2$, $CH_2CH_2OCONR$, $CH_2CH=CH$ or $CH_2C≡C$; where R in the above expressions is hydrogen or methyl and which are linked with the group Y via a carbon atom.

Particularly preferred combinations of Y and X are $SCH_2CH_2$, $SCH_2CH_2NH$, $SCH_2CH_2O$, $SCH_2CH_2CH_2$, $SCH_2CH_2CH_2NH$ and $SCH_2CH_2CH_2O$.

In formula I, Q is a residue of the formula either —V-A1-L-A2-W. Alternatively and if X does not represent a bond, Q in formula I may also be —NR6R7.

V can be a divalent aromatic or heterocyclic group, e.g. one of those specifically mentioned above.

In another preferred group of compounds of formula (I) or (I-A) the group V is a divalent group of formula

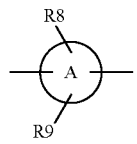

wherein

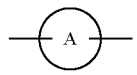

is a phenylene ring or a x-membered saturated or unsaturated divalent heterocycloaliphatic or heteroaromatic ring containing from 2 to (x-1) carbon atoms with x being 5 to 8, preferably 5 or 6, and from 1 to 4 hetero atoms selected from the group consisting of sulfur, and preferably oxygen and nitrogen, R8 and R9 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, an oxo group; or from aryl or heterocyclyl, which may be unsubstituted or substituted with one or more of the above identified substituents other than aryl or heterocyclyl, or when both substituents R8 and R9 are located at adjacent carbon atoms of the ring Ⓐ, these two substituents, taken together with said adjacent carbon atoms, can also form a 5- or 6-membered aromatic or a x-membered saturated or unsaturated heterocycloaliphatic or heteroaromatic ring containing from 2 to (x-1) carbon atoms with x being 5 to 8, preferably 5 or 6, and from 1 to 4 hetero atoms selected from the group consisting of sulfur and preferably, oxygen and nitrogen, and wherein V can have altogether one to four substituents of the kind as defined for R8 and R9 and the free valences can be located either on one or on both rings of the group V.

Particularly preferred meanings of V include:

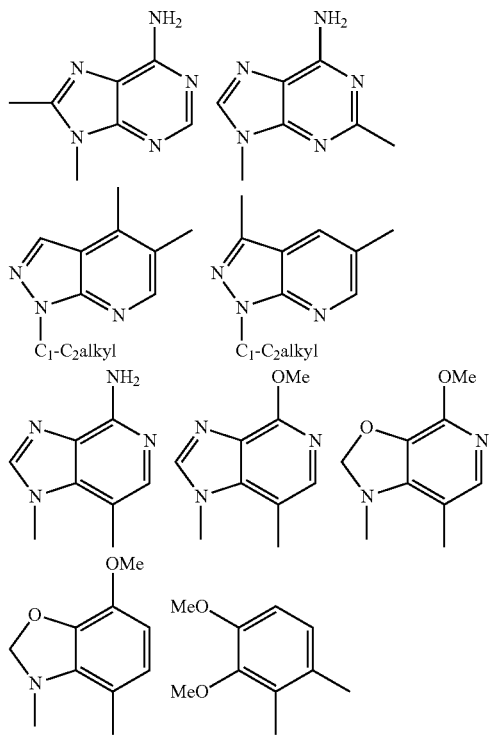

-continued

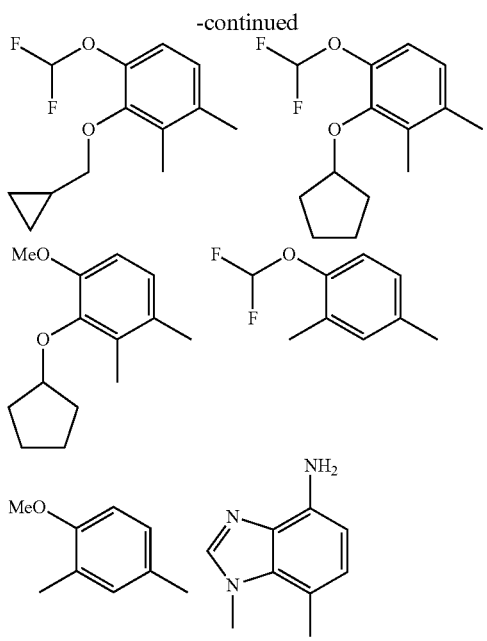

W in formula (I) or (I-A) can be either aryl or, preferably, heterocyclyl, both as explained above.

In a group —V-A1-L-A2-W, wherein at least one of the groups A1; L or A2 is present, W can also be a monovalent substituted or unsubstituted, saturated or unsaturated linear group with up to 5 atoms consisting of C, N, O and/or S of which one carbon can appear as a CO group one sulphur atom can appear as an $SO_2$ group. In this case W may also carry additional hydrogen atoms to saturate a C or a N atom, as already described above with reference to group X.

In a preferred embodiment of formula (I) or (I-A) the residue W represents a group of formula

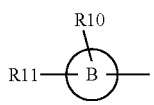

wherein

is a phenyl ring or a x-membered saturated or unsaturated heteroaliphatic or heteroaromatic ring containing from 2 to (x-1) carbon atoms with x being 5 to 8, preferably 5 or 6, and from 1 to 4 hetero atoms selected from the group consisting of sulfur, and preferably oxygen and nitrogen, R10 and R11 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, and an oxo group; or when both substituents R10 and R11 are located at adjacent carbon atoms of the ring

, these two substituents, taken together with said adjacent carbon atoms, can also form a 5- or 6-membered aromatic or a x-membered saturated or unsaturated heteroaliphatic or heteroaromatic ring containing from 2 to (x-1) carbon atoms with x being 5 to 8, preferably 5 or 6, and from 1 to 3 hetero atoms selected from the group consisting of sulfur and preferably, oxygen and nitrogen, wherein W can have alltogether one to four substituents of the kind as defined for R10 and R11 and the free valence can be located on either ring of the group W.

Particularly preferred examples of W are the following groups:

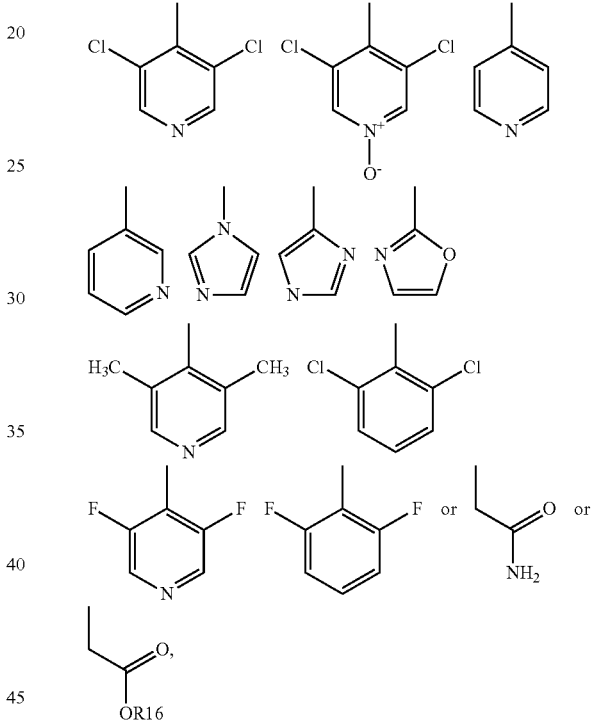

wherein R16 is hydrogen or $C_1$-$C_4$alkyl, in particular methyl.

In a group —V-A1-L-A2-W groups A1 and A2 are, in general, independently of each other either absent or a $C_1$-$C_4$alkylene group. L is generally selected from a single bond, —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH— and —NH(CO)O—, preferably from —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH— and —NH(CO)O—, in such group, but may also be absent if A1 and/or A2 are present.

In preferred examples of macrolide compounds according to the invention A1 and A2 are independently of each other either absent or represent a $C_1$-$C_2$alkylene group; and L is selected from —NH—, —(CO)NH— and —NH(CO)—; or is absent.

Particularly preferred are the compounds of formula (I) and (I-A) wherein

A1, A2 are independently of each other either absent or a C$_1$-C$_2$alkylene group;

L is —NH—, —(CO)NH— or —NH(CO)—;

V is a divalent group of formula

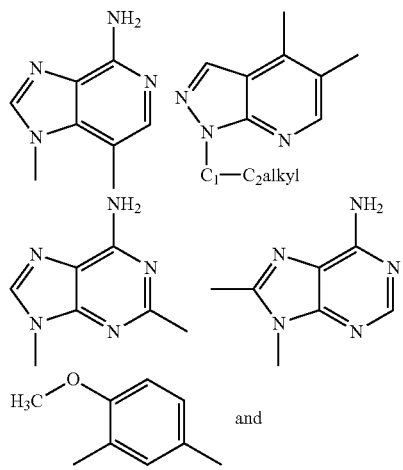

and

W is a group of formula

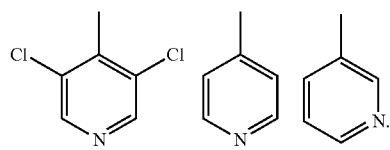

Also preferred are the compounds of formula (I) or (I-A), e.g. those mentioned in the preceding paragraph, wherein Y is —S— and X is —CH$_2$—CH$_2$—CH$_2$— or, preferably, —CH$_2$—CH$_2$—NH— or —CH$_2$—CH$_2$—O— linked to the residue Q via the NH group or O atom respectively, or —CH$_2$—CH$_2$—, most preferably —CH$_2$—CH$_2$—.

If X does not represent a bond in formula (I) or (I-A), then Q may also be —NR6R7. In this case R6, and R7 may be independently selected from aryl, aralkyl, heterocyclyl and heterocyclylalkyl, e.g. as explained above, and one of R6 and R7 can also be a group -L-A2-W; preferably -L-W, wherein A2, L and W have one of the meanings mentioned above.

Preferred examples of corresponding macrolide compounds according to the invention are compounds of formula I wherein Q is a group —NR6R7 and has one of the following formulae

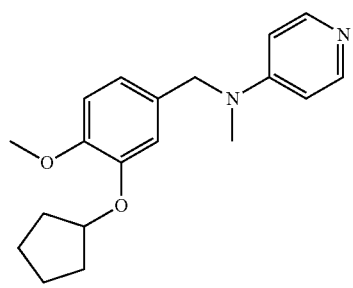

-continued

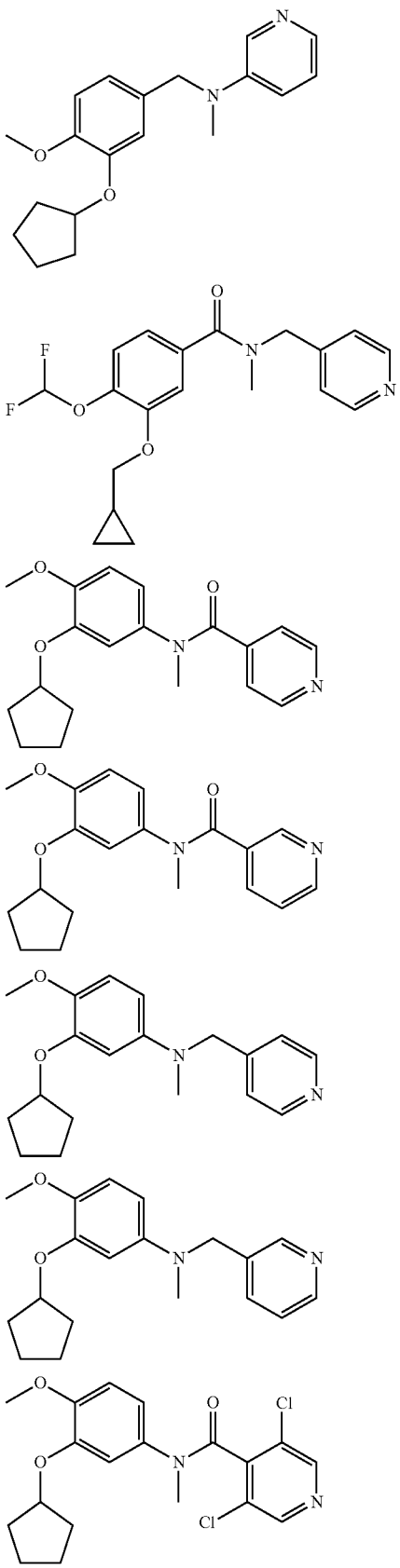

-continued

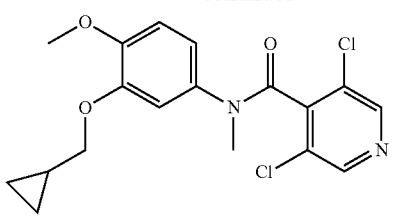

wherein

means a methoxy residue.

In other specific embodiments of the compounds of formula (I) or (I-A) the group Q represents a residue W as generally defined above. Specific compounds of this type comprise as group W a group of one of the formulae

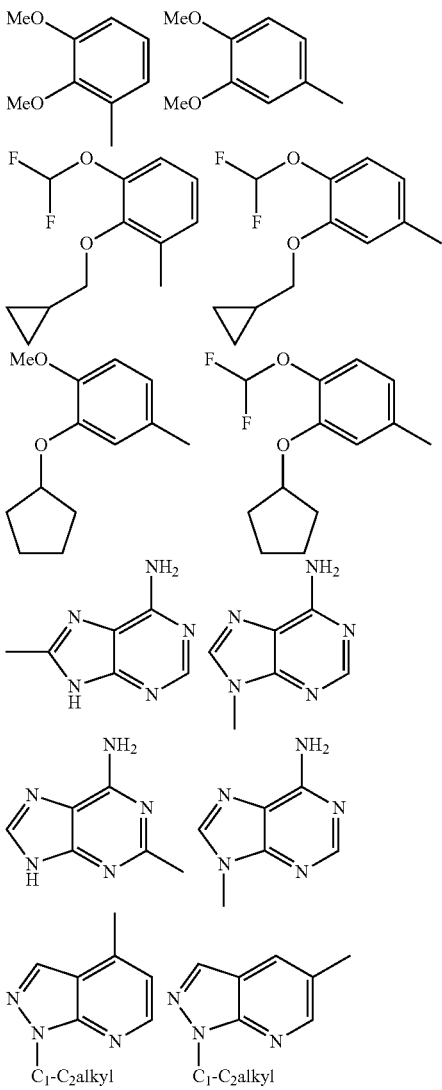

-continued

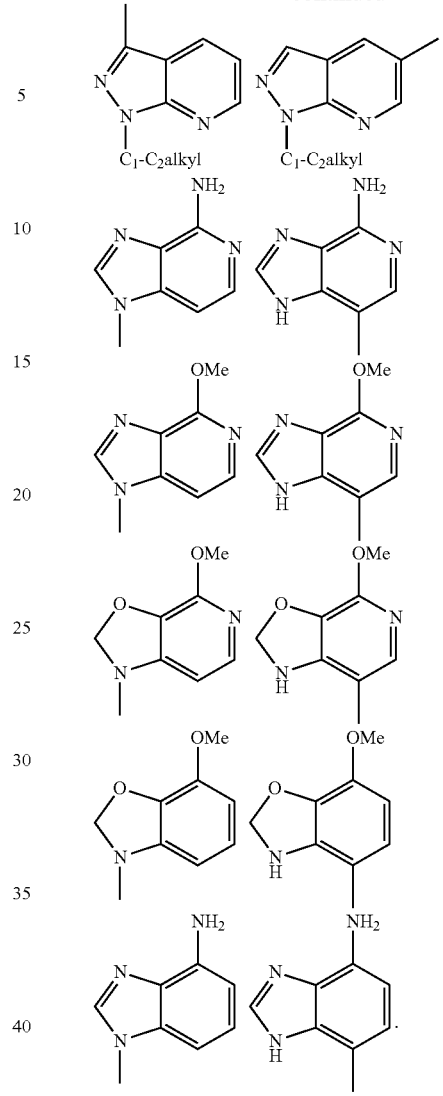

Particularly preferred are the compounds of formula (I), wherein R12 and R13, taken together with the carbon atom to which they are linked, represent a C=O group and R14 is a methyl group.

Furthermore, the following preferences apply, also in combination with other preferences described herein:

When a group R2a is present in the compounds of formula (I), this is preferably hydrogen.

Preferred as well are compounds of formula (I), wherein R2 and R3, taken together with the carbon atom to which they are linked, represent a C=O group Also preferred are compounds of the formula (I), wherein R2 and R4, taken together with the bond between the carbon atoms to which they are linked, form a double bond and the compounds of formula (I), wherein R4 is hydrogen.

Further preferred embodiments of the compounds of formula (I) and formula (I-A) for use in the present invention include:

such compounds wherein R13 is hydroxyl or allyloxy;

such compounds wherein R12 and R13 taken together with the carbon atom to which they are linked, represent a C=O group, such compounds wherein R14 represents hydrogen or, preferably, methyl, in particular said compounds wherein OR14 in position 6 of the macrolide ring represents methoxy.

Again, said preferences can be combined with one or more of the other preferences described herein.

Specific examples of the compounds for use according to the present invention include, e.g. compound has one of the following formulae:

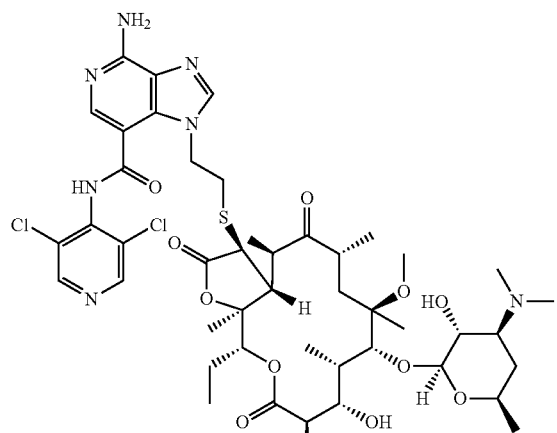

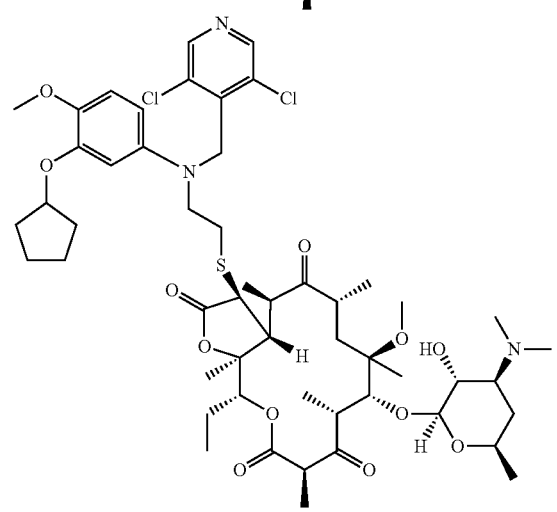

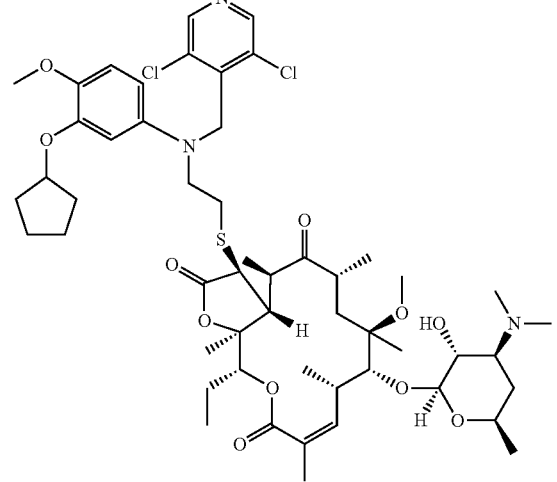

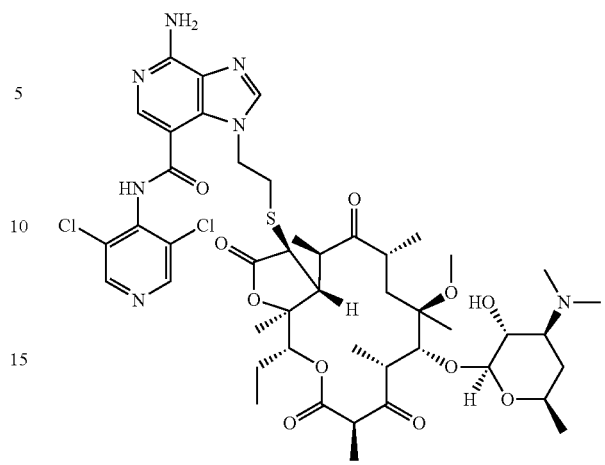

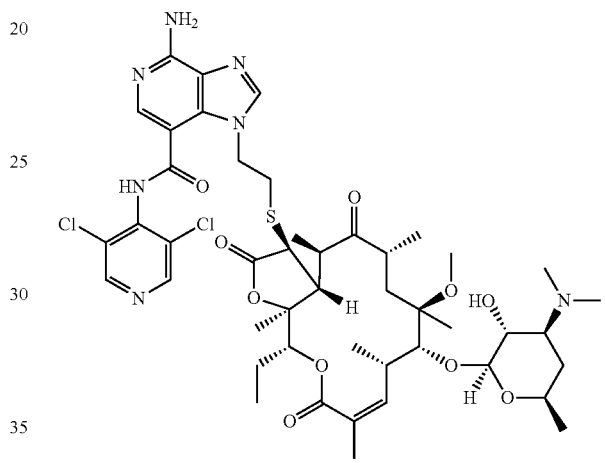

The following compounds represent new examples of compounds according to the present invention for use specifically in the prevention and/or treatment of cancer in animals or humans:

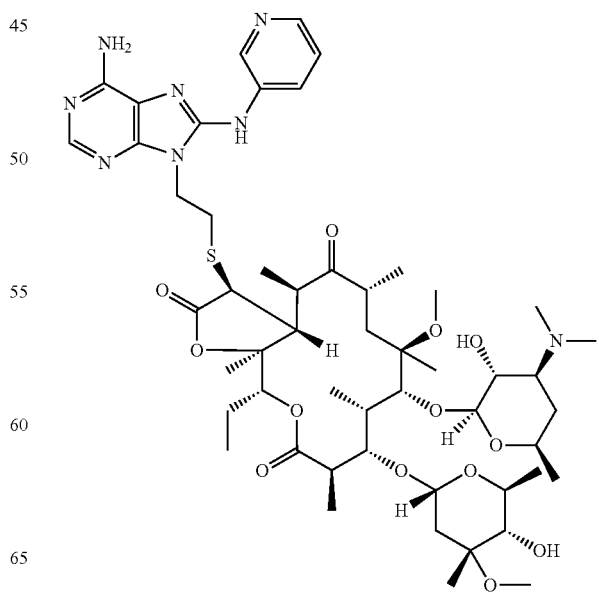

17
-continued
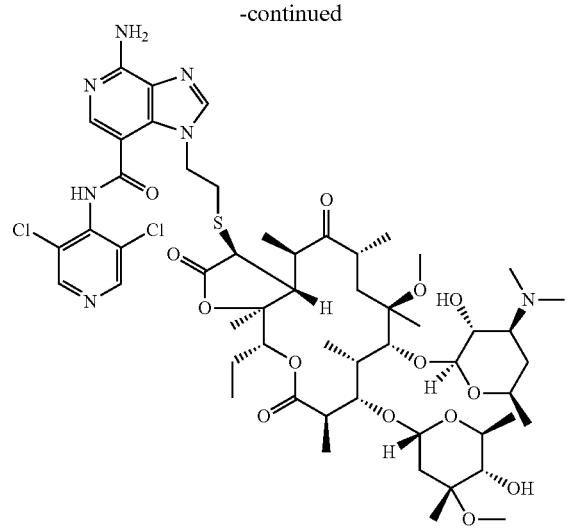
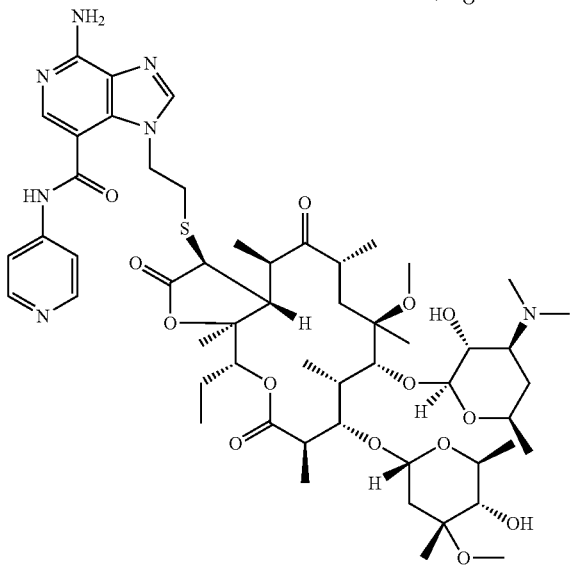
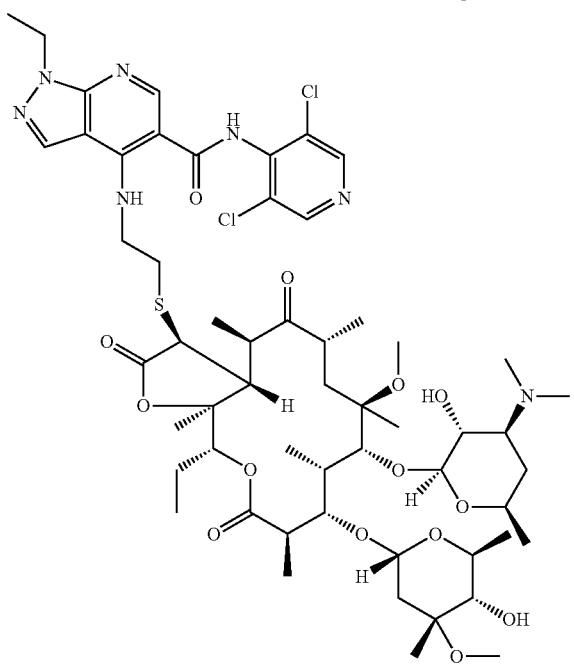
18
-continued
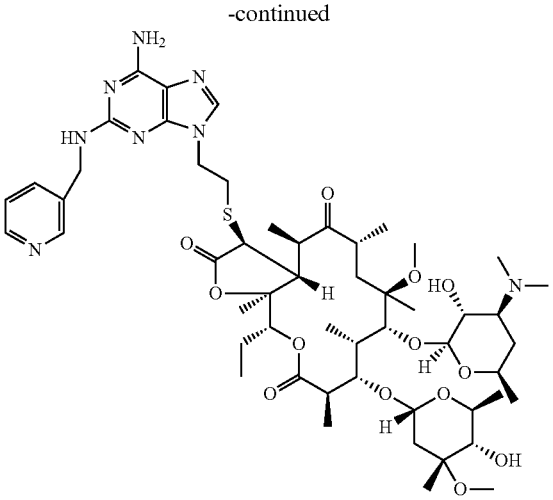
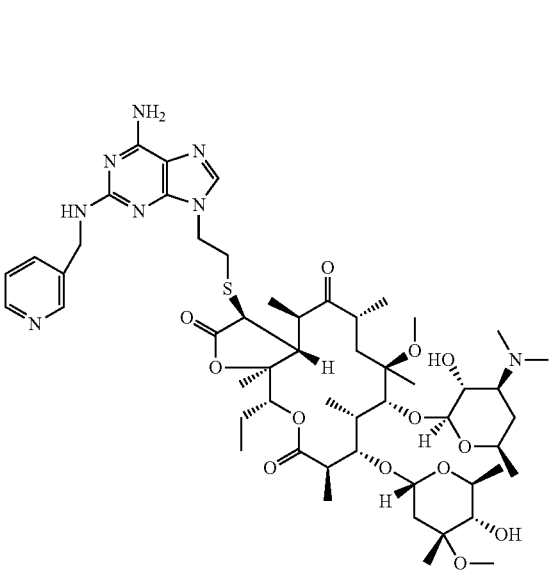
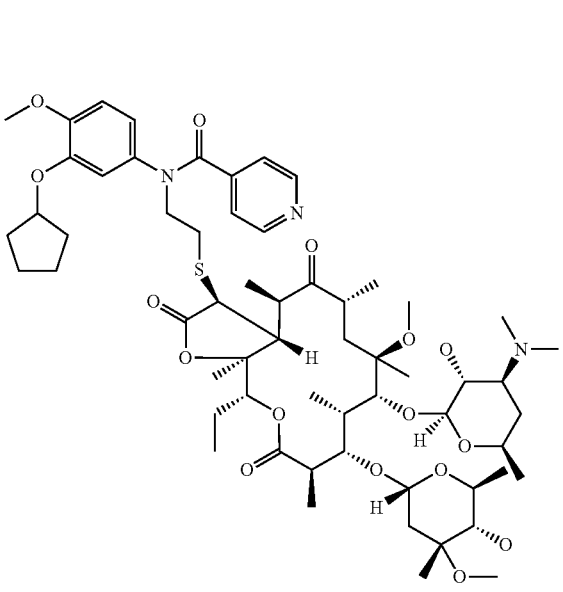

-continued
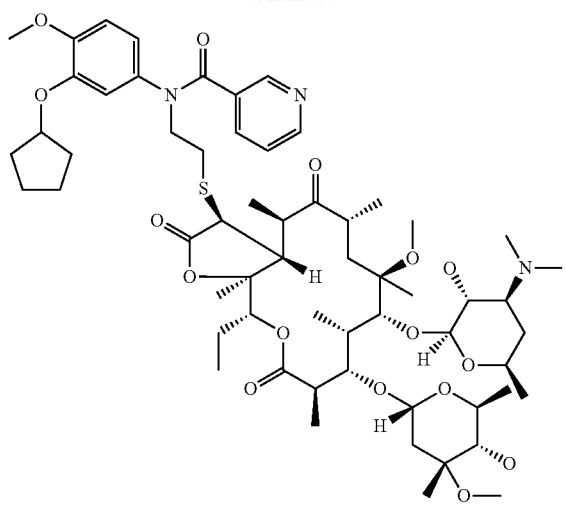
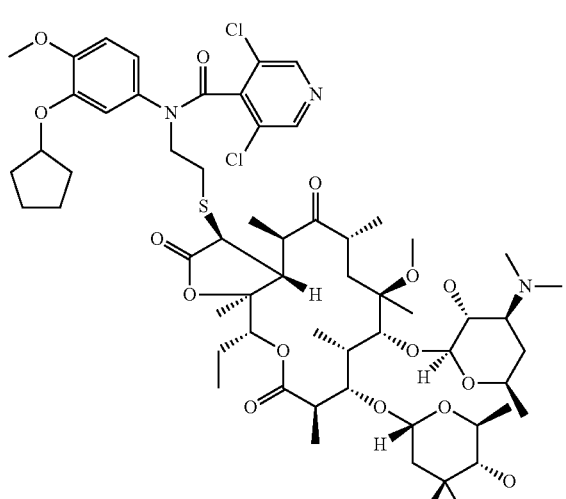
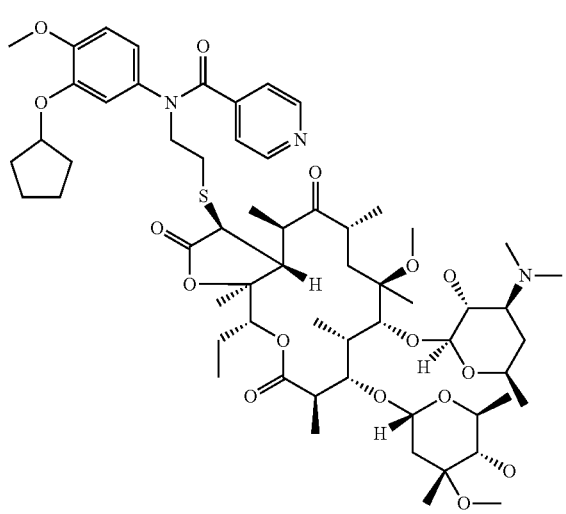
-continued
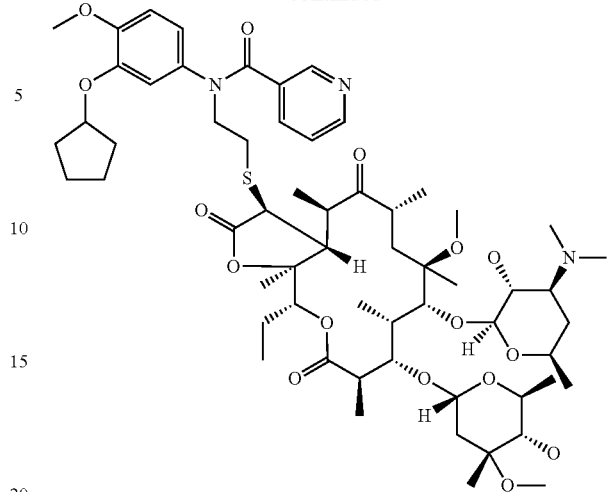
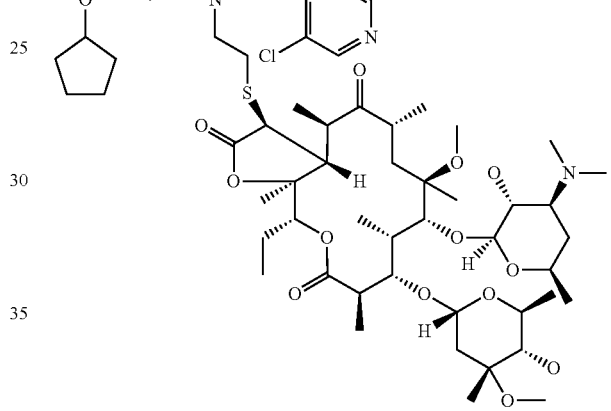
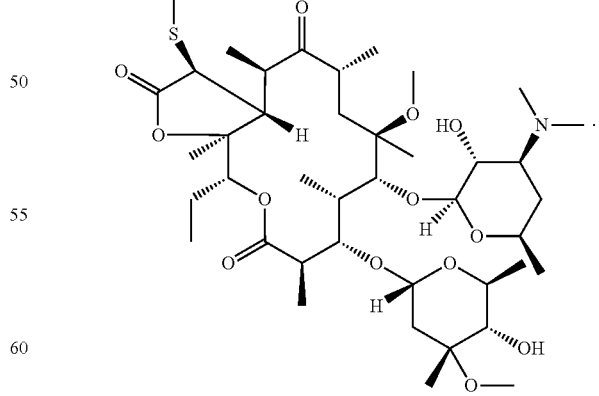
As already indicated above, the macrolide compounds of formula (I) or formula (I-A) can, if desired, also be present and used as pharmaceutically acceptable acid addition salts. Not only salts with inorganic acids, but also salts with organic acids come into consideration. Hydrochlorides, hydrobromides, sulfates, nitrates, citrates, acetates, trifluoroacetates, maleates, succinates, methanesulphonates, p-toluenesulphonates and the like are examples of such salts.

Furthermore, the compounds of formula (I) or formula (I-A) can be in form of and used as in vivo cleavable esters, for example esters with of the 2'-hydroxy group of the amino sugar moiety. Suitable esters are generally acetates, pivaloyl esters, tartrates, maleates, succinates, and the like.

The compounds of formula (I) and their pharmaceutically acceptable acid addition salts or in vivo cleavable esters can according to the present invention e.g. be used for the prevention and/or treatment of diseases such as chronic obstructive pulmonary disease (COPD), asthma, rheumatoid arthritis, atopic dermatitis or inflammatory bowel disease or for the prevention and/or treatment of diseases such as chronic bronchitis, emphysema, urticaria, allergic rhinitis, allergic conjunctivitis, psoriasis, septic shock, adult respiratory distress syndrome and multiple sclerosis.

Both, the compounds of formula (I) as well as the compounds of formula (I-A) can furthermore be used according to the present invention for the prevention and/or treatment of cancer.

Suitable subjects for a treatment according to the invention are, in principle, animals, in particular mammals, and humans. The use for humans is preferred.

The compounds of formula (I) and formula (I-A) can, in accordance with the invention, also be used as a medicament in form of a pharmaceutical composition comprising one or more of said compounds and a pharmaceutically acceptable carrier. The compounds of formula (I) and (I-A) possess good oral absorption properties.

Further embodiments of the present invention are thus pharmaceutical compositions comprising a compound of formula (I) or one of its preferred embodiments described above or a pharmaceutically acceptable acid addition salt thereof, a N-oxide thereof or an in vivo cleavable ester thereof and a pharmaceutically acceptable carrier for use in a method for the prevention and/or treatment of disorders and/or diseases in a subject selected from an animal or a human, wherein said method is based on an inhibition of phosphodiesterases, in particular of phosphodiesterase 4 in said subject;

for use for the prevention and/or treatment of inflammatory or allergic diseases or diseases associated with uncontrolled cellular growth, proliferation and/or survival, in animals or humans; in particular for the prevention and/or treatment of asthma, chronic bronchitis, emphysema, atopic dermatitis, urticaria, allergic rhinitis, allergic conjunctivitis, psoriasis, rheumatoid arthritis, chronic obstructive pulmonary disease (COPD), septic shock, ulcerative colitis, inflammatory bowel disease, e.g. Crohn's disease, adult respiratory distress syndrome or multiple sclerosis in humans, more preferably, for the prevention and/or treatment of chronic obstructive pulmonary disease (COPD), asthma, rheumatoid arthritis or atopic dermatitis in humans; and for use for the prevention and/or treatment of cancer, in humans; particularly for use for the treatment of cancer.

Another specific embodiment of the present invention are pharmaceutical compositions comprising a compound of formula (I-A) or one of its preferred embodiments described above or a pharmaceutically acceptable acid addition salt thereof, a N-oxide thereof or an in vivo cleavable ester thereof and a pharmaceutically acceptable carrier for the prevention and/or prevention and/or treatment of diseases associated with uncontrolled cellular growth, proliferation and/or survival in humans, e.g. cancer.

The pharmaceutical compositions and products in accordance with the invention can be administered, for example, perorally, such as in the form of tablets, film coated tablets, sugar coated tablets, hard and soft capsules, solutions, emulsions or suspensions, or rectally, such as in the form of suppositories, or parenterally e.g. by injection, or nasally, or by inhalation or transdermally, or locally for example by topical administration, preferably the compounds are administered topically or orally.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

Although the compounds of formula (I) or (I-A) may, in principle, be used according to the invention as such, it is preferred to incorporate the compounds into compositions specifically suitable for the envisaged administration route, i.e. in suitable oral, parenteral or topical dosage forms which are known to those skilled in the art or can be developped with usual skills. These pharmaceutical compositions can contain, as optional ingredients, any of the various adjuvants which are used ordinarily in the production of pharmaceutical preparations.

Thus, for example, for formulating the present compositions as oral dosage forms, one may use, as optional ingredients, fillers, such as microcrystalline cellulose, calcium phosphate or lactose; disintegrating agents, such as starch, crosslinked carboxymethylcellulose sodium or crosslinked polyvinylpyrrolidone; and lubricating agents, such as talc, magnesium stearate, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, film coated tablets, sugar coated tablets and hard capsules there can be used, for example, lactose, maize starch or derivatives thereof, talc, stearic acid or its salts. Suitable carriers for soft capsules are, for example, vegetable oils, waxes, fats and semi-solid and liquid polyols (depending on the nature of the active substance). Suitable carrier materials for the preparation of solutions and syrups are, for example, water, alcohols, polyols, saccharose, invert sugar and glucose. Suitable carrier materials for suppositories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavoring agents, salts for adjusting the osmotic pressure, buffers, coating agents and antioxidants.

The compounds of formula (I) or (I-A) and their acid addition salts, N-oxides or in vivo cleavable esters thereof can also be used for parenteral administration. For such purpose, in particular as a preparation for injection, the compounds are used in form of lyophilisates or dry powders for dilution together with customary agents, such as water or isotonic common salt solution.

The compounds of formula (I) or (I-A) and their acid addition salts, N-oxides or in vivo cleavable esters thereof can also be used for topical administration and are, for this purpose, are preferably used in form of topical preparations like ointments, creams or gels.

Accordingly, the use of a compound of formula (I) or their acid addition salts, N-oxides or in vivo cleavable esters for the manufacture of a medicament for the treatment of a disorder or disease which can be ameliorated by inhibition of human phosphodiesterases, particularly of human phosphodiesterase 4. and for the manufacture of a medicament for the prevention and/or treatment of an inflammatory or allergic disease or a disease associated with uncontrolled cellular growth, proliferation and/or survival, e.g. cancer in a subject selected from an animal and a human as well as the use of a compound of formula (I-A) or their acid addition salts, N-oxides or in vivo cleavable esters for the manufacture of medicament for the prevention and/or treatment of or a disease associated with uncontrolled cellular growth, proliferation and/or survival, e.g. cancer, in a subject selected from an animal and a human are further aspects of the present invention.

In yet another aspect, the present invention relates to a method for treating a subject affected by a disorder or disease which can be ameliorated by inhibition of phosphodiesterases, particularly of phosphodiesterase 4, wherein the subject is selected from an animal, in particular a mammal, and more preferably a human in need of such treatment and an amount of a compound of formula (I) is administered to said subject which amount is effective for ameliorating said disorder or disease or, more particularly, for treating or preventing an inflammatory or allergic disease, in said subject and wherein an amount of a compound of formula (I) is administered to said subject, which amount is effective in preventing or treating said inflammatory or allergic disease in said subject, or relates to a method for treating a subject selected from an animal, in particular a mammal, and more preferably a human affected by cancer wherein an amount of a compound of formula (I) or formula (I-A) is administered to said subject which amount is effective for treating cancer in said subject.

For the treatment and/or prevention of inflammatory, allergic diseases or cancer in mammals, in particular in humans, a daily dosage of about 10 mg to about 2000 mg, especially about 50 mg to about 1000 mg, is usual, with those of ordinary skill in the art appreciating that the dosage will among other known parameters also depend upon the age, type and weight of and condition of the mammal, and the kind of disease to be prevented or treated. The daily dosage can be administered in a single dose or can be divided into several doses. An average single dose of about 10 mg, 100 mg, 250 mg, 500 mg and 1000 mg can be contemplated as being suitable in general.

Compounds of formula (I-A) as used according to the invention can be prepared starting from erythromycin A, clarithromycin, or any other 6-O-alkyl-erythromycin A, 6-O-alkenyl-erythromycin A or 6-O-alkynyl-erythromycin A. The preparation of compounds of formula II, III and IV wherein $Rp_1$ and $Rp_2$ are H, acetyl, benzoyl or any other suitable hydroxyl protecting group can be prepared by methods well known in the art (Scheme 1).

Scheme 1

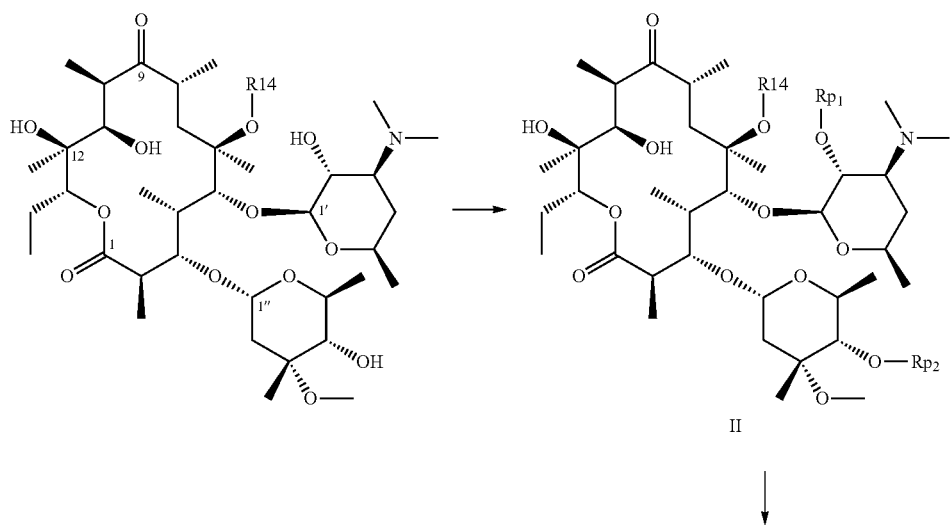

-continued

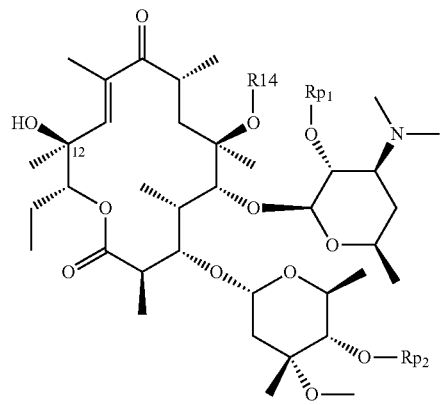

IV

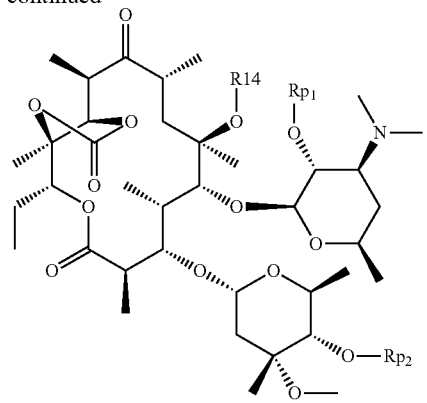

III

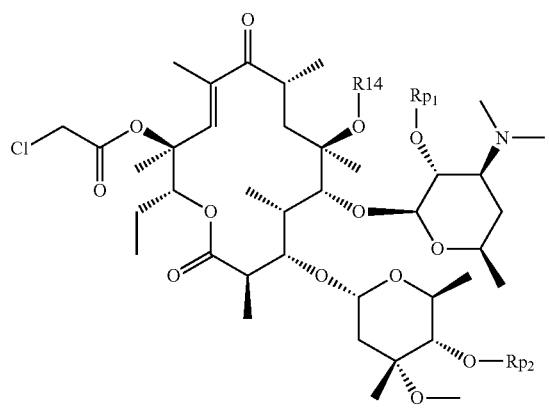

V

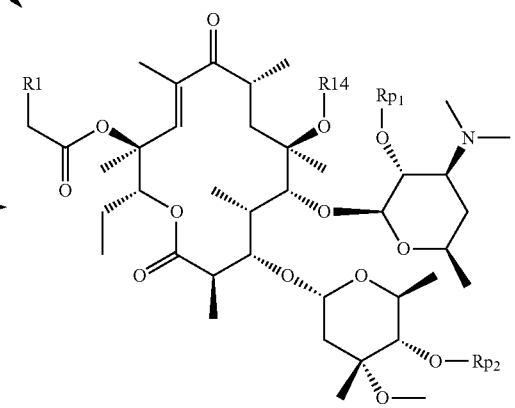

VI

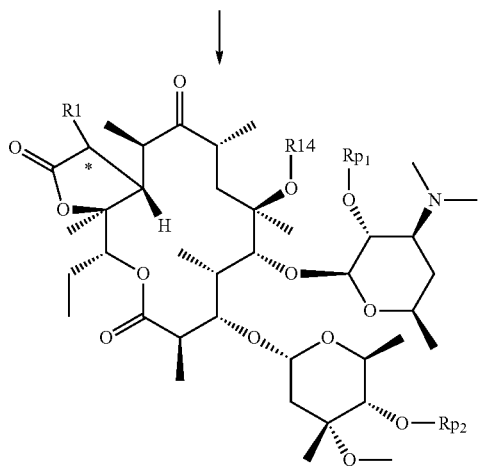

VII

To obtain compounds of formula II wherein $Rp_1$ and $Rp_2$ are as defined above the 2'- and 4"-hydroxyl groups of starting macrolide can be protected either sequentially or simultaneously by reaction with a suitable acid anhydride or acid chloride as described in, for example, Baker et al., J. Org. Chem. 1988, 53, 2340-2345 and Kashimura et al., J. Antibiotics, 2001, 54, 664-678. Compounds of formula II can then for example be transformed into compounds of formula IV in a similar way as described in Baker et al., J. Org. Chem. 1988, 53, 2340-2345.

The hydroxy group at position 12 of compounds of formula IV is esterified by treatment with 2-chloro acetic acid, an activating agent such as DCC and DMAP or with 2-chloro acetic anhydride, pyridine, DMAP in a chlorinated solvent such as methylene chloride. The intermediate V is then treated with the appropriate nucleophile Q-X—SH in acetone in the presence of a base such as DBU to give compounds of formula VI wherein R1, $Rp_1$ and $Rp_2$ are as defined above. Depending on the nature of R1 compounds of formula VI can also be synthesised by reacting compound of formula IV with an appropriate carboxylic acid ($R1CH_2COOH$), an activating agent such as DCC and DMAP in a suitable solvent such as methylene chloride to give compounds of formula VI. Compounds of formula VI are treated with an alkali metal base such as NaH or potassium tert.-butoxide or LDA in an aprotic solvent such as DMF or THF to give compounds of formula VII (Scheme 1).

Compounds of formula VII wherein R1, $Rp_1$ and $Rp_2$ are as defined above are deprotected at the 2'-position with methanol at temperatures ranging from 20° C. to 60° C. during 2-5 days to give compounds of formula VIII (scheme 2). The 4"-hydroxyl group is deprotected by treatment of the compound with DBU in refluxing methanol for 3 to 12 hours (J. Antibiotics, 2001, 54(8), 664) or by treatment with guanidine/ guanidinium nitrate in methanol/dichloromethane (Tetrahedron Letters 1997, 38(9), 1627) or with potassium carbonate in methanol or with a mixture of MeONa in methanol, preferably with DBU in refluxing methanol for 5 to 7 hours to give compounds of formula Ia.

Alternatively compounds of formula VII can be deprotected at the 2'- and the 4"-position simultaneously using one of the methods described above for the deprotection of the 4"-hydroxyl group to give compounds of formula Ia (Scheme 2).

Scheme 2

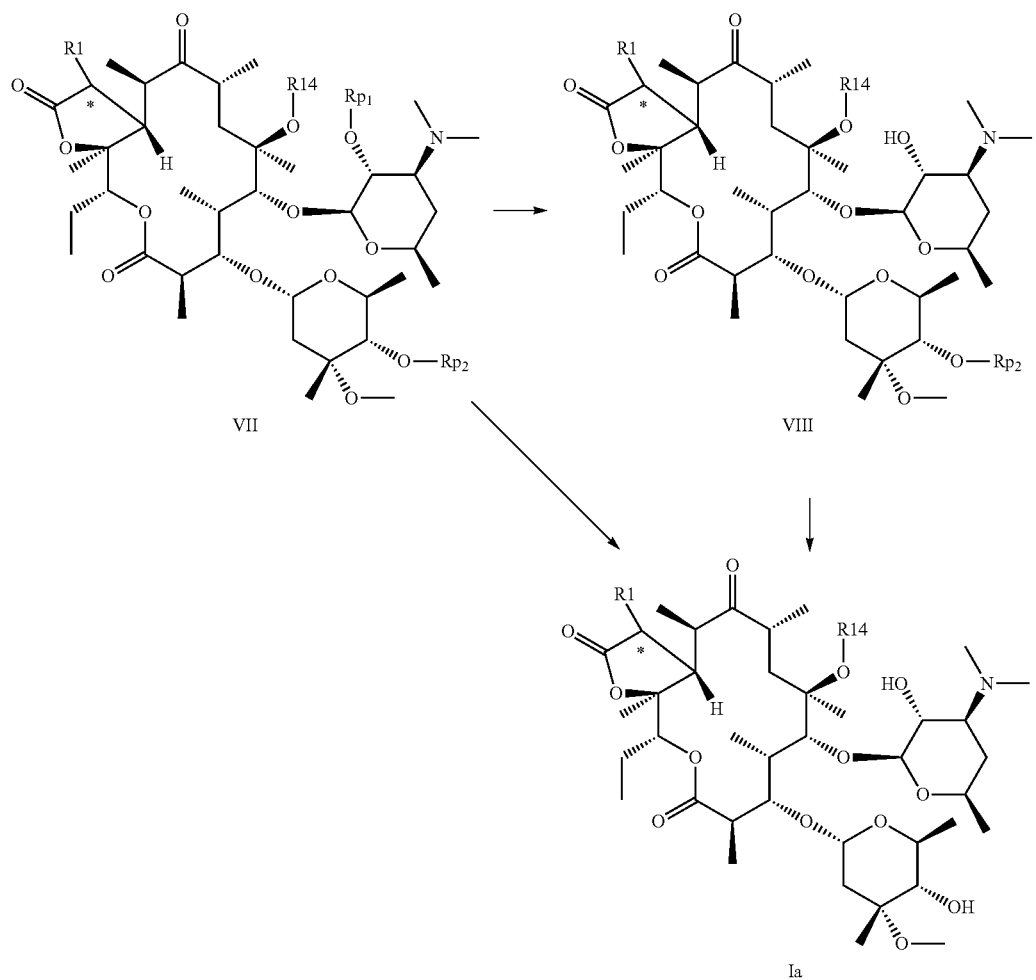

In the case where R1 is $S-Rp_3$ and $Rp_3$ is a sulphur protecting group e.g. benzyl, 4-methoxybenzyl, 3,4-dimethoxybenzyl or 4-nitro-benzyl, preferably 4-methoxybenzyl the intermediate VIIa is transformed in the presence of molecular sieves into disulfide derivative IX wherein $Rp_1$ and $Rp_2$ are as defined above and $Rp_4$ is e.g. 3-nitro-2-pyridinyl or methyl similar to the method described in WO03/072588.

Compounds of formula IX are treated with a reducing agent such as a trialkyl phosphine, preferably tributyl phosphine, or a triaryl phosphine, preferably triphenyl phosphine, in a solvent such as aqueous acetone, aqueous dimethyl formamide, aqueous dioxane or aqueous tetrahydrofuran, preferably aqueous dimethyl formamide, preferably at 0° C. to 60° C., for 1 minute to 1 hour, to give compound X. Compound X is treated, preferably without isolation, directly in the same solvent system with compounds of the formula Q-X-Lg, in which Q and X are defined as before and Lg is a leaving group, e.g. chloride, bromide, iodide, methanesulfonyloxy, p-tosylsulfonyloxy, trifluormethansulfonyloxy or a vinyl group in the case where X represents a carbonyl or a sulfonyl group to give compounds of formula VII. The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo[5.4.0]undec-7-ene or 1,5-diazabicyclo[4.3.0]non-5-ene, preferably 1,8-diazabicyclo[5.4.0]undec-7-ene at temperature between 0° C. and 50° C. It can be advantageous to add catalytic amounts of an iodide salt, preferably sodium iodide, to the reaction mixture (Scheme 3).

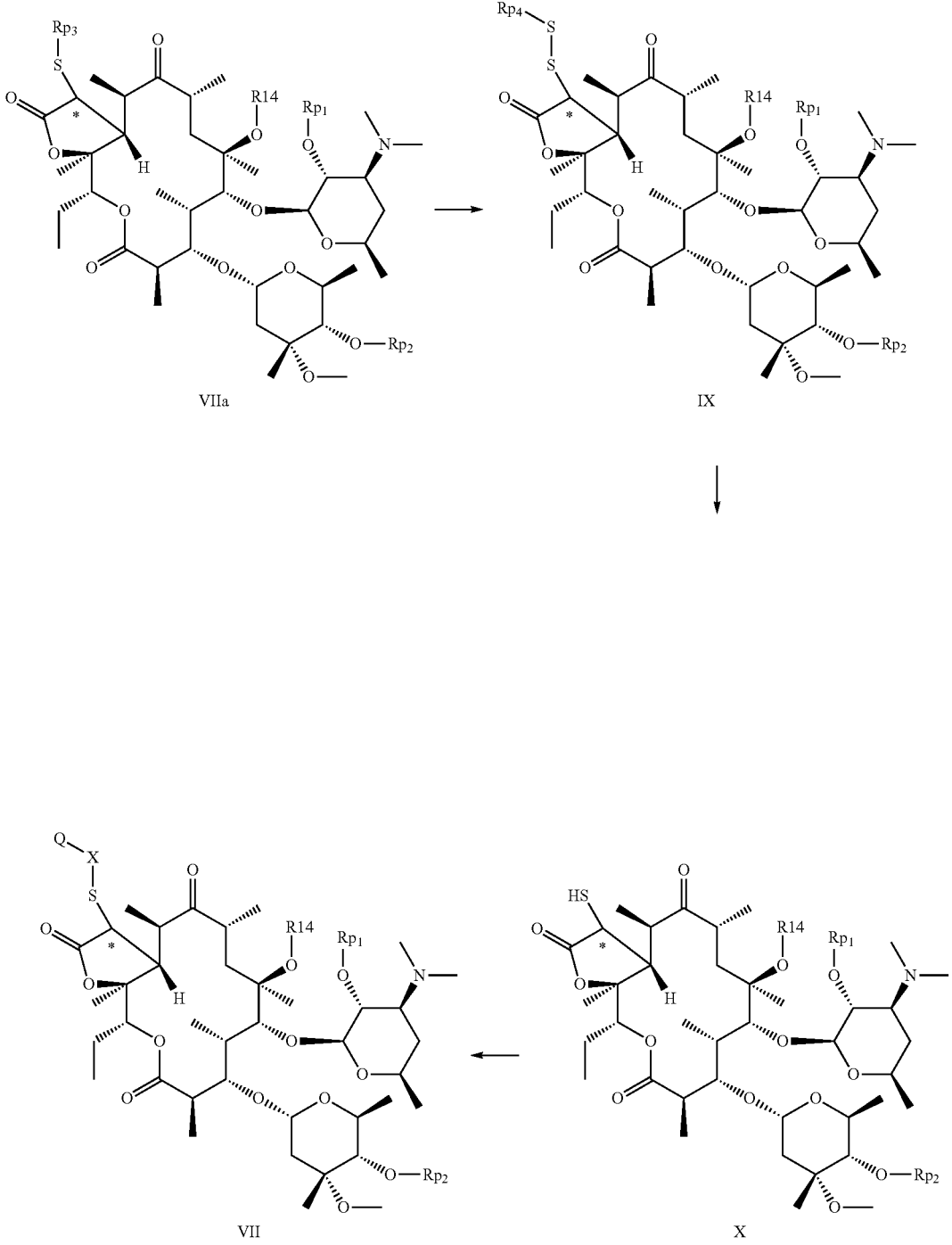

Alternatively, compounds of formula I-A, wherein R2 and R3 taken together form a group C=O and R4 has the meaning above and R1 is a residue —Y—X-Q, wherein X and Q have the same meaning as described above and Y is S; can also be prepared by a) converting a macrolide compound having the formula

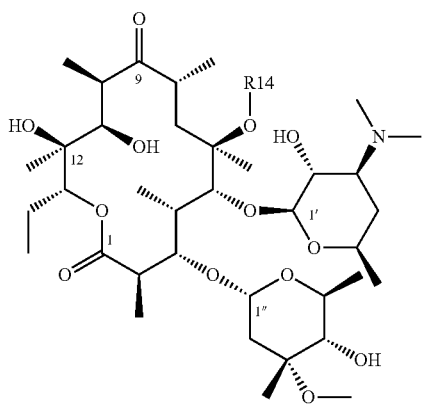

in a manner known per se to a compound of formula IV, e.g. as described above with regard to Scheme 1

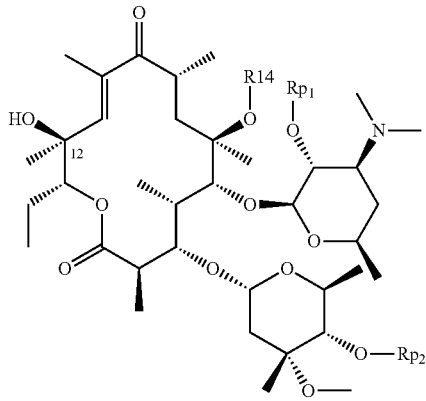

IV wherein $Rp_1$ and $Rp_t$ each are a hydroxyl protecting group and R4 is as defined above, b1) converting said compound of formula IV in the presence of an activated chloroacetic acid derivative, like e.g. di(chloroacetic acid) anhydride, in a manner known per se to a compound of formula V, e.g. as described above under Scheme 1

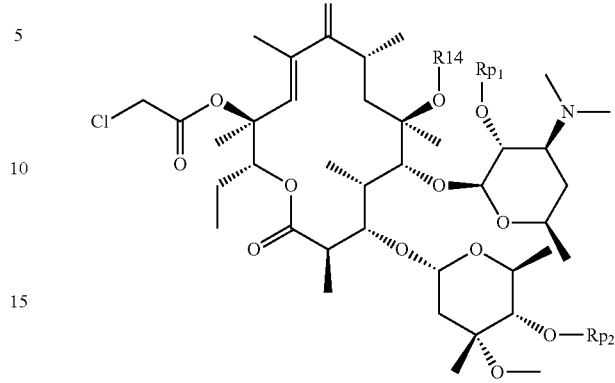

V wherein $Rp_1$ and $Rp_2$ and R4 have the meaning above;

b2) further reacting said compound of formula V with a compound of formula

MS—X-Q, wherein M represents alkali metal atom and X and Q have the meaning described above, to form a compound of to a compound of formula VI

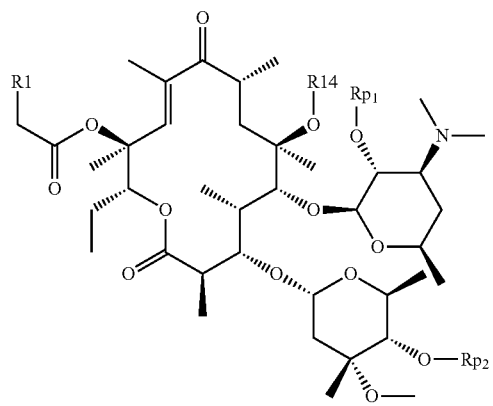

VI wherein R1 is —S—X-Q, and X, Q, $Rp_1$ and $Rp_2$ and R4 have the meaning above, c) reacting said compound of formula VI in an aprotic solvent with an alkali metal base to form a compound of formula VII

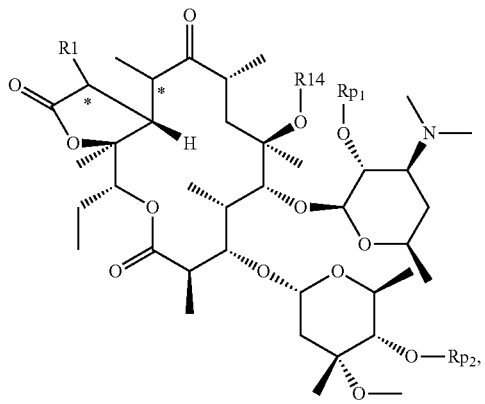

VII wherein R1 and Rp$_1$ and Rp$_2$ and R4 have the meaning above, and removing the hydroxyl protecting groups Rp$_1$ and Rp$_2$ simultaneously or consecutively to form the compound of formula I-A.

These compounds can be converted, if desired, in a manner known per se, e.g. as indicated in Scheme 5 to a compound of formula I wherein R12 is hydrogen and R13 is selected from hydroxyl or —O-(aliphatic group), said aliphatic group representing a saturated or unsaturated aliphatic group with 1 to 6 carbon atoms.

Compounds of formula Ic can e.g. be prepared by treatment of compounds of formula Ib (compound of formula I where Y=S) with 2 to 2.5 equivalent of 3-chloroperoxybenzoic acid (mCPBA) and 4 to 5 equivalent of NaHCO$_3$ in a solvent such as methylene chloride at temperatures ranging from 0° C. to room temperature preferably 0° C. during 1 hour to 3 hours. The N-oxide which is formed on the dimethylamino group of the sugar residue during the reaction is reduced at work-up by treating the organic phase with a aqueous solution of sodium pyrosulfite at room temperature during 5 minutes to 24 hours to give the desired compounds of formula Ic as a mixture of diastereoisomers. Alternatively, if appropriate, the N-oxide is reduced by catalytic hydrogenation according to standard procedures. Compounds of formula Ic can be further oxidised as described above but at room temperature during 1 to 48 hours to give, after reduction of the N-oxide, compounds of formula Id. Compounds Id can also be obtained in one step from compounds of formula Ib by using 3,5 to 10 equivalent of the oxidising agent and 7 to 20 equivalent of NaHCO$_3$ at temperatures ranging from 0° C. to room temperature during 5 to 48 hours followed by the workup procedure described above (scheme 4).

In the case where Q is further substituted with oxidation sensitive substituents like amino groups, these substituents might need to be protected before submitting the sulfide Ia to oxidation. Suitable protecting groups commonly known in the art can be introduced according to standard procedures described in T. W. Green et al., Protective Groups in Organic Synthesis, John Wiley & Sons, 1999. After oxidation, the protecting group can be removed following standard procedures also described in T. W. Green et al.

Scheme 4

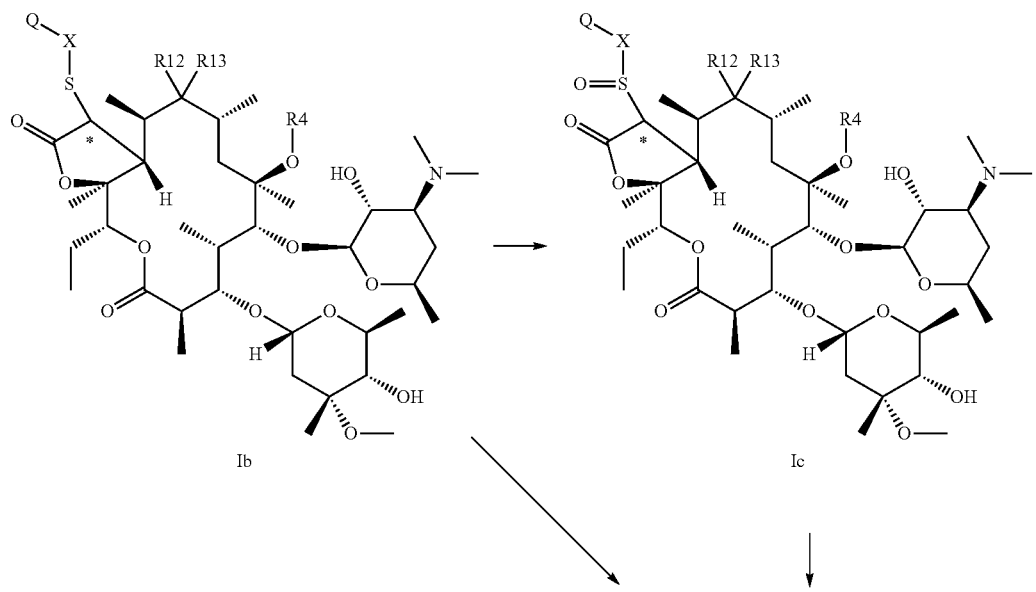

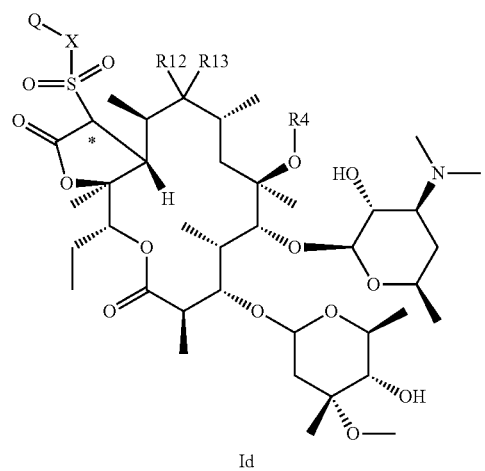
Id
Scheme 5
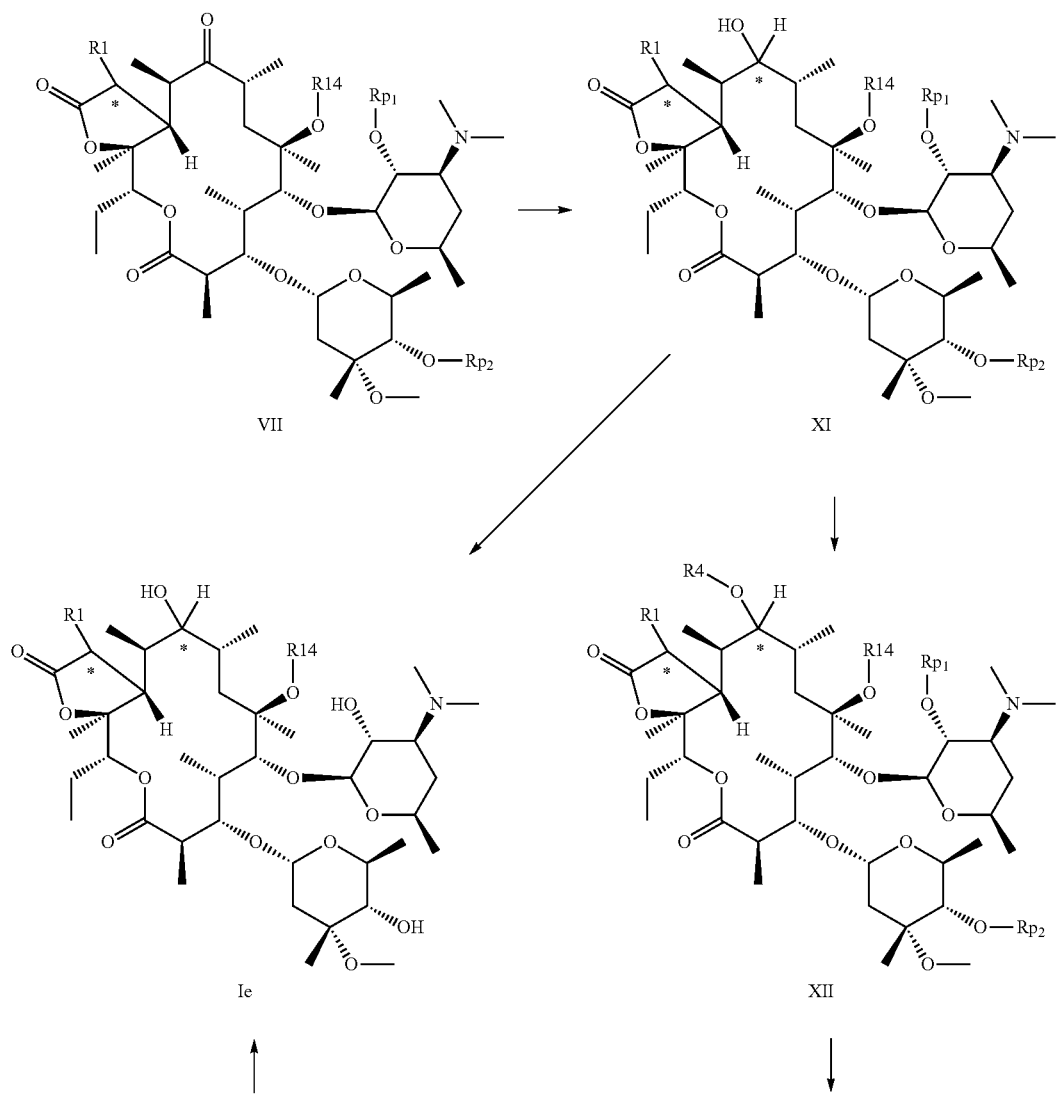

-continued

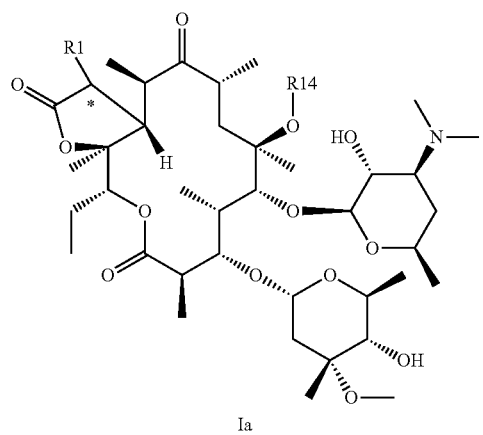

Ia

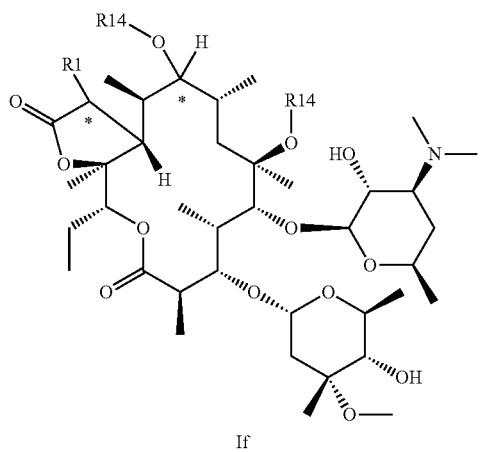

If

Compounds of formula XI can e.g. be prepared by treatment of compounds of formula VII with a reducing agent such as NaBH₄ in a solvent such as methanol, ethanol, isopropanol, THF, THF/water or diethylether at temperatures ranging from 0° C. to room temperature, during 1 hour to 24 hours. Compounds of formula XI are then deprotected as described above to obtain compounds of formula Ie. Alternatively, compounds of formula Ie can also be prepared starting from compounds of formula Ia following the method described for the reduction of compounds of formula VII. In the case where $Rp_1$ is acetyl the protecting group might get partially removed during reduction in a solvent such as methanol requiring a re-protection of the 2'-hydroxy group prior to the alkylation of the newly formed hydroxy group.

The hydroxyl group of compound of formula XI is alkylated following standard procedures known for the alkylation of hydroxyl groups to give compounds of formula XII. In the case where Q is further substituted with substituents that are alkylated under the conditions used for the transformation of XI into XII, these substituents might need to be protected before submitting compound XI to alkylation. Suitable protecting groups commonly known in the art can be introduced according to standard procedures described in T. W. Green et al., Protective Groups in Organic Synthesis, John Wiley & Sons, 1999. After alkylation, the protecting group can be removed following standard procedures also described in T. W. Green et al. Compounds of formula XII are deprotected following procedures described above to give compounds of formula If.

The compounds XII-1 (Scheme 6) for use in the present invention can e.g. be obtained from compounds XII (cf. Scheme 5) through selective cleavage of the cladinose moiety of the compounds of formula VII or XII by methods known in the art, e.g. by reaction of said compounds with 1 to 5% HCl in an alcoholic solvent such as methanol or ethanol or in water or a mixture thereof for 12 to 72 hours at temperatures preferably from minus 15° C. to 40° C. as described e.g. in WO 02/16380.

Scheme 6

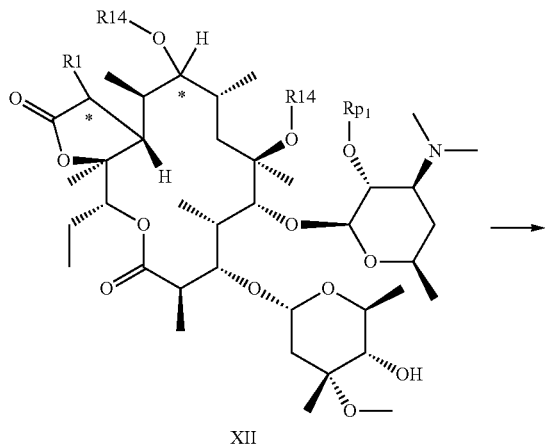

XII

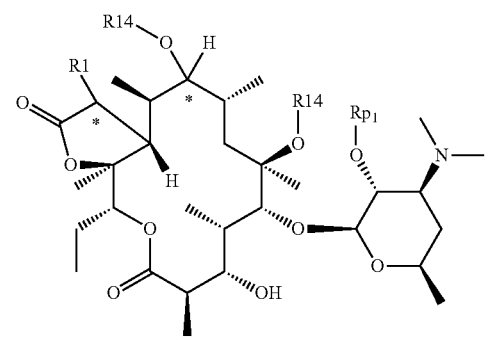

XII-1

The preparation of compounds of formula (I) wherein R2 and R4 taken together form a double bond, R3 is hydrogen and R1 and R14 are as defined above (compounds Ig) is carried out according to Scheme 7.

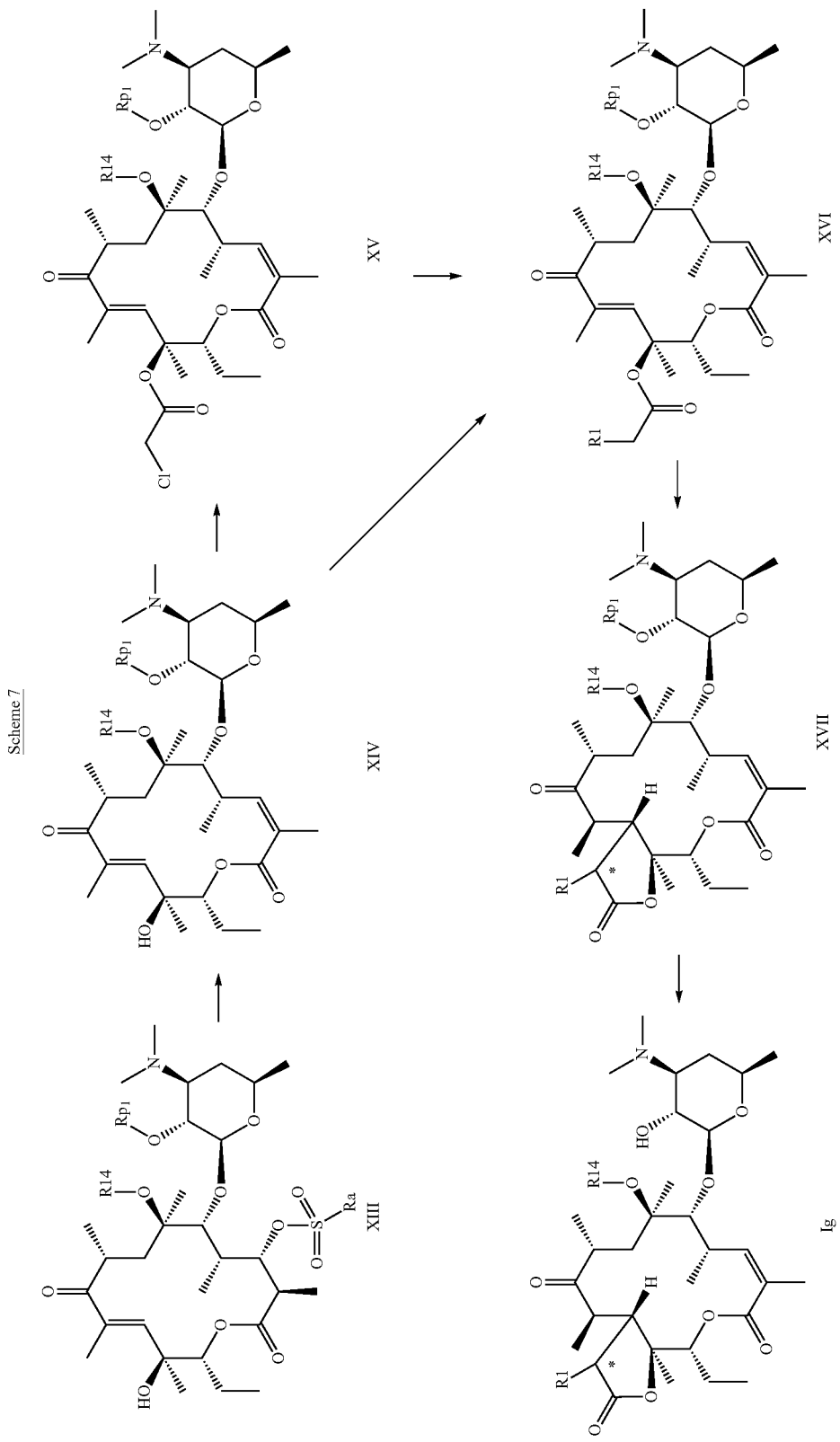

Compounds of formula Ig may e.g. be prepared starting from compounds of formula XIII where $Rp_1$ is acetyl, benzoyl or the like and Ra is methyl, trifluoromethyl or methylphenyl. The preparation of compound of formula XIII where $Rp_1$ is acetyl and Ra is methyl is e.g. described in J. Med. Chem. 1998, 41, 1651. Compound of formula XIII is treated with a base such as sodium hydride or DBU in a solvent such as acetone, toluene, DMF or THF or a mixture thereof at 0° C. to 50° C. to give the compound of formula XIV. The compound of formula XIV is esterified by treatment with 2-chloro acetic acid, an activating agent such as DCC and DMAP or with 2-chloro acetic anhydride, pyridine, DMAP in a solvent such as dichloromethane, chloroform or tetrahydrofuran preferably dichloromethane to give a compound of formula XV. The intermediate XV is then treated with the appropriate nucleophile Q-X—SH where Q and X are as defined above in acetone in the presence of a base such as DBU to give compounds of formula XVI. Depending on the nature of R1 compounds of formula XVI can also be synthesized by reacting compound of formula XIV with an appropriate carboxylic acid ($R1CH_2COOH$), an activating agent such as DCC and DMAP in a suitable solvent such as methylene chloride to give compounds of formula XVI. Compounds of formula XVI are treated with an alkali metal base such as NaH or potassium tert.-butoxide or LDA in an aprotic solvent such as DMF or THF to give compounds of formula XVII. Compounds of formula XVII wherein $Rp_1$ is as defined above are deprotected with methanol at temperatures ranging from 20° C. to 60° C. during 2-5 days or by treatment of the compound with DBU in refluxing methanol for 3 to 12 hours (J. Antibiotics, 2001, 54(8), 664) or by treatment with guanidine/guanidinium nitrate in methanol/dichloromethane (Tetrahedron Letters 1997, 38(9), 1627) or with potassium carbonate in methanol or with a mixture of MeONa in methanol, preferably with methanol for 2-5 days at 20-50° C. to give compounds of formula Ig.

The preparation of compounds of formula I wherein R2 and R3, taken together with the carbon atom to which they are linked, form a C═O group, R4 is hydrogen and R1 is as defined above (Compounds Ih) and of compounds of formula I where R2 is —OH and R3 and R4 are hydrogen and R1 is as defined above (Compounds Ii) is carried out according to Scheme 8. The synthesis of compounds of general formula XVIII has been described in e.g. WO03/072588 and WO2006/084410. Compounds of formula XIX can be obtained by treatment of compounds of formula XVII with 1% to 5% HCl in an alcoholic solvent e.g. methanol or ethanol, or in water or a mixture thereof at temperatures ranging from 0° C. to 30° C. Compounds of formula Ih are obtained from compounds of formula XIX by the same methods as described above for the preparation of compounds of formula Ig from compounds of formula XVII.

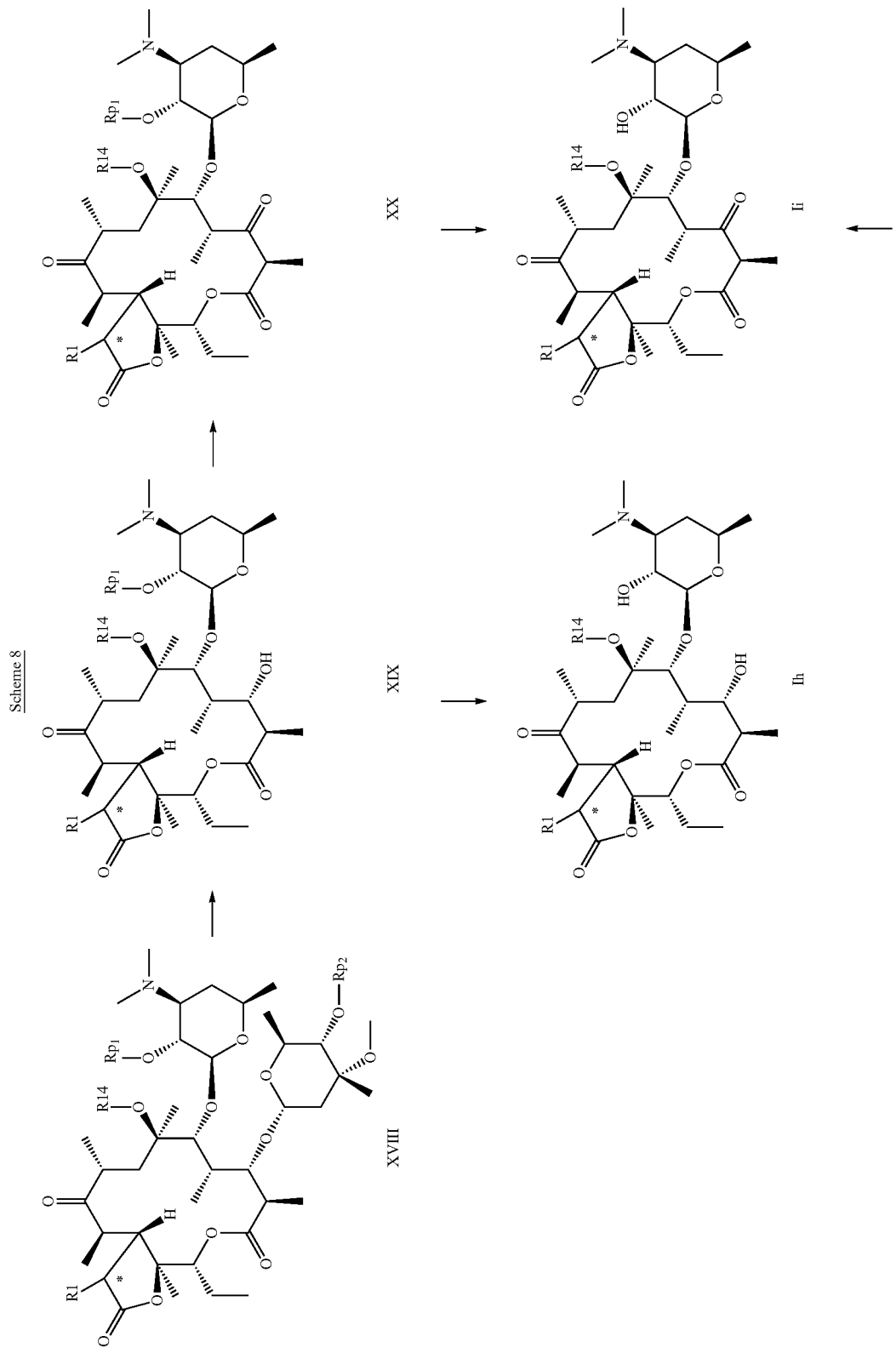

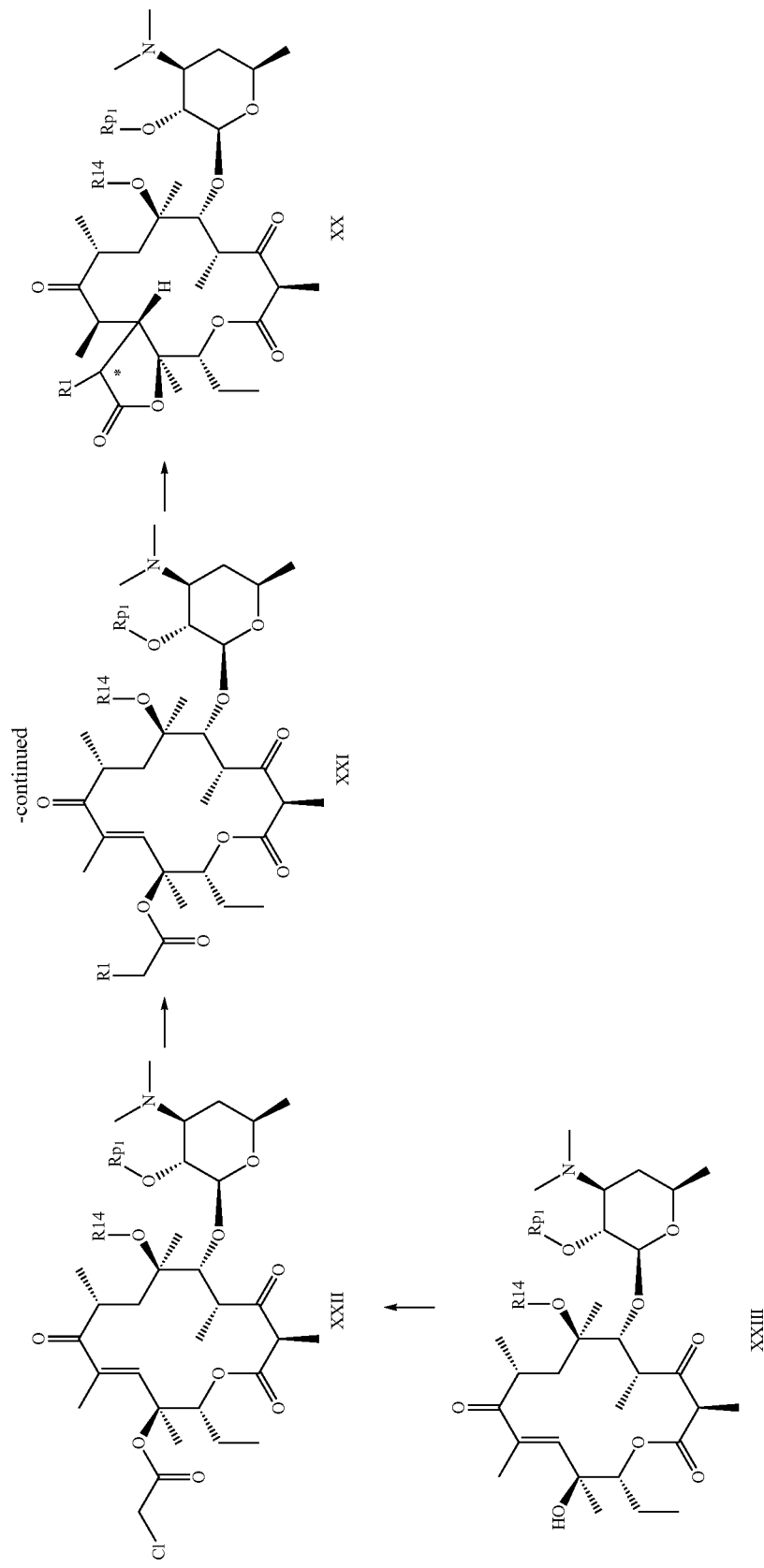

The oxidation of compounds XIX is carried out with EDC*HCl, DMSO and pyridinium trifluoroacetate in a chlorinated solvent such as methylene chloride or using 1,1,1-triacetoxy-1,1-dihydro-1,2-benziodoxol-3-(1H)-one (Dess-Martin reagent) in a chlorinated solvent such as methylene chloride or using N-chlorosuccinimide and dimethylsulfide in a suitable solvent such as methylene chloride to give compounds of formula XX. Compounds of formula II are obtained from compounds of formula XX by the same methods as described above for the preparation of compounds of formula Ig from compounds of formula XVII. Alternatively compounds of formula II may be obtained starting from compound XXIII according to procedures described in Scheme 7. The synthesis of compound of formula XXIII is described in J. Med. Chem. 1998, 41, 4080.

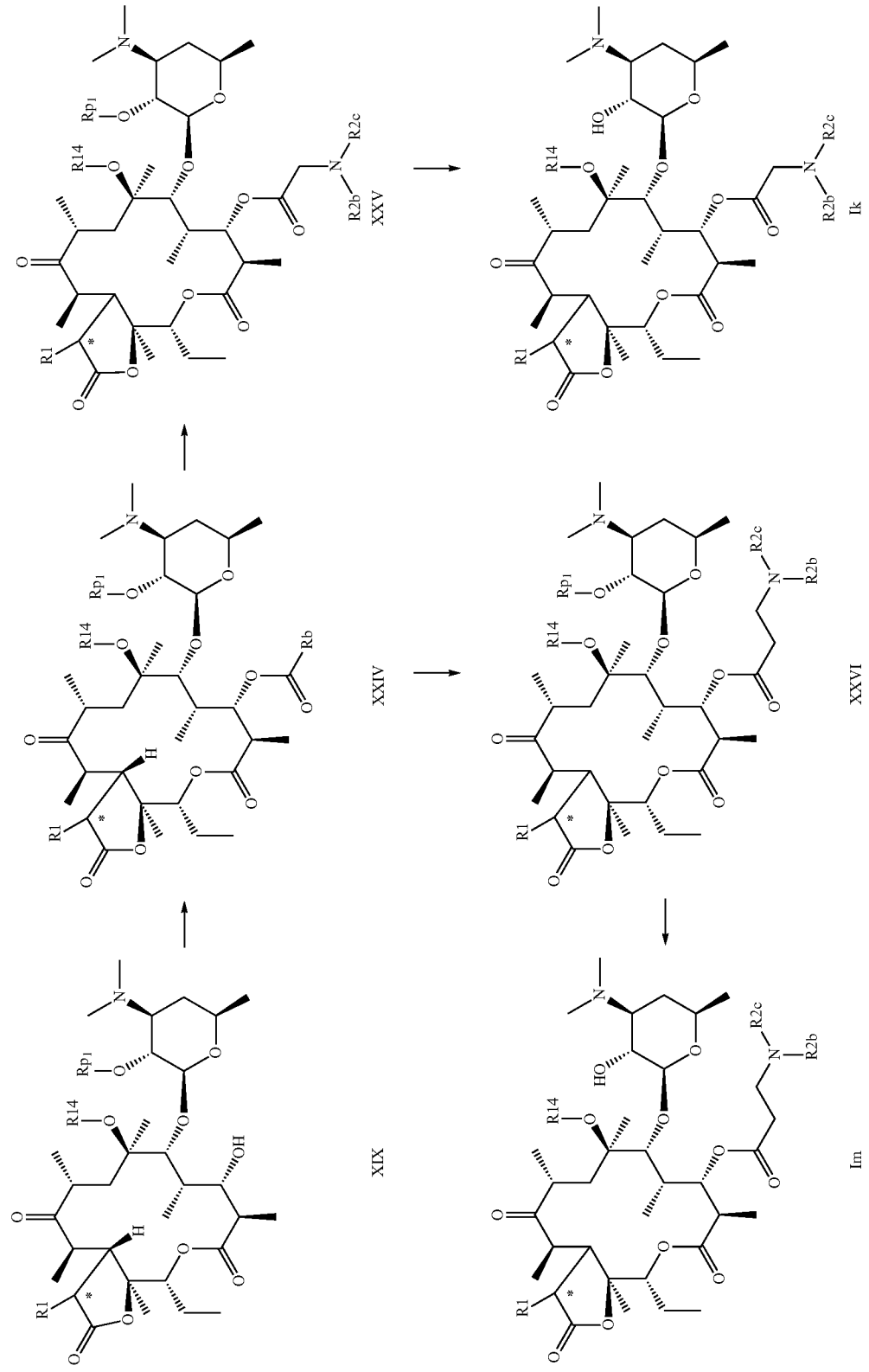

Compounds of formula Ik may be obtained by reacting compound XIX with 2-chloroacetylchloride, 2-chloroacetic acid anhydride or 2-chloroacetic acid according to methods well known in the art for the esterification of hydroxyl groups to give compounds of formula XXIV (Rb=CH$_2$Cl). This compound is then reacted with an appropriate nucleophile such as for example dimethylamine or morpholine followed by a deprotection as described above to give compounds of formula Ie (Scheme 9). Compounds of formula Im are obtained in a similar way by reacting compound XIX with acroyl chloride according to methods well know in the art to give compound XXIV where Rb is CH=CH$_2$.followed by treatment with the appropriate nucleophile.

In the case where R1 is S-Rp$_3$ (Scheme 10) and Rp$_3$ is a sulphur protecting group e.g. benzyl, 4-methoxybenzyl, 3,4-dimethoxybenzyl or 4-nitro-benzyl, preferably 4-methoxybenzyl, the intermediate XXVII is transformed into disulfide derivative XXVIII wherein R2-R4, R14 and Rp$_1$ are as defined above and Rp$_4$ is e.g. 3-nitro-2-pyridinyl or methyl similar to the method described in WO03/072588 or in WO2006084410. Compounds of formula XXVIII are treated with a reducing agent such as a trialkyl phosphine, preferably tributyl phosphine, or a triaryl phosphine, preferably triphenyl phosphine, in a solvent such as aqueous acetone, aqueous dimethyl formamide, aqueous dioxane or aqueous tetrahydrofuran, preferably aqueous dimethyl formamide, at 0° C. to 60° C., for 1 minute to 1 hour, to give compound XXIX.

Compound XXIX is treated, preferably without isolation, directly in the same solvent system with compounds of the formula Q-X-Lg, in which Q and X are as defined before and Lg is a leaving group, e.g. chloride, bromide, iodide, methanesulfonyloxy, p-tosylsulfonyloxy, trifluormethan-sulfonyloxy to give compounds of formula XXX which may be deprotected according to methods described above to give compounds of formula I with Y=S. The reaction is preferably effected in the presence of a base such as alkali metal carbonate or hydrogen carbonate, e.g. potassium carbonate, cesium carbonate or sodium hydrogen carbonate, or an organic base, e.g. triethylamine, N-ethyl N,N-diisopropylamine, 1,8-diazabicyclo[5.4.0]undec-7-ene or 1,5-diazabicyclo[4.3.0]non-5-ene, preferably 1,8-diazabicyclo[5.4.0]undec-7-ene at temperature between 0° C. and 50° C., preferably at 20° C. It can be advantageous to add catalytic amounts of an iodide salt, preferably sodium iodide, to the reaction mixture. If required, protecting groups are removed according to methods well known in the art as described e.g. in T. W. Green et al., Protective Groups in Organic Synthesis, John Wiley & Sons, 1999.

Scheme 10

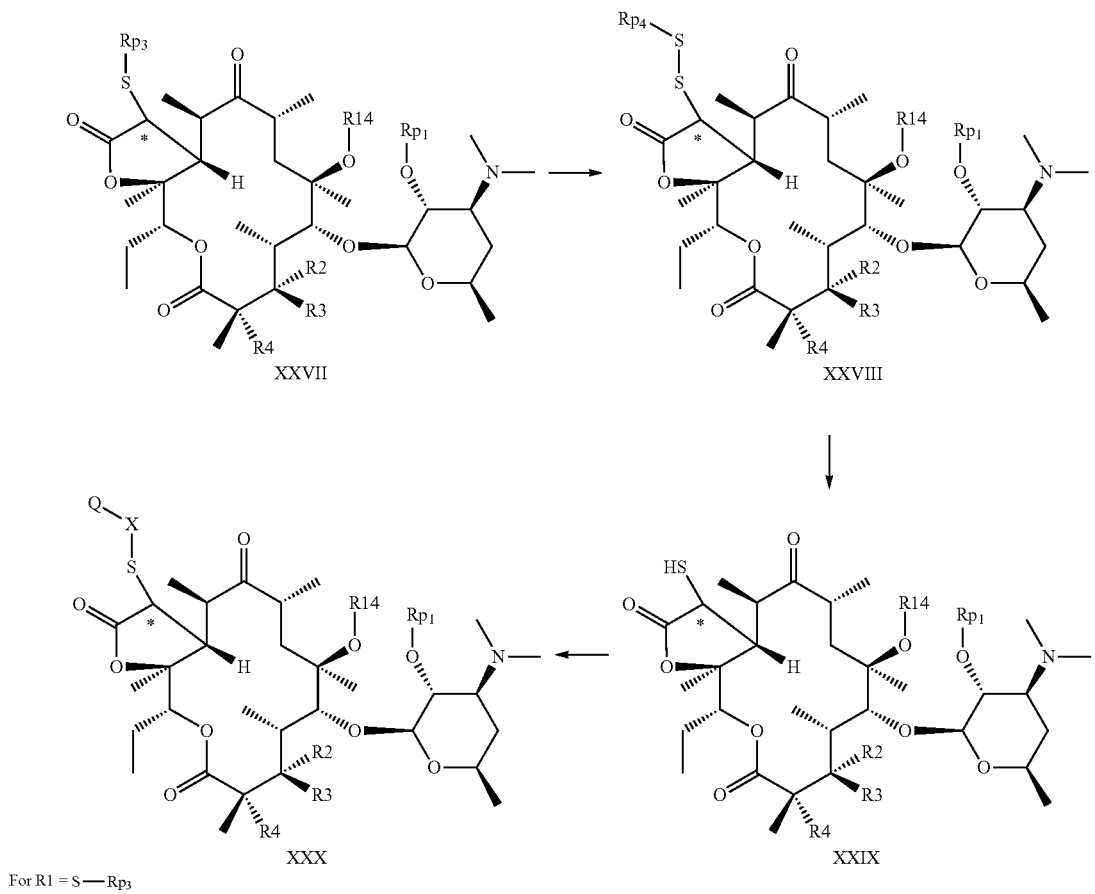

For R1 = S—Rp$_3$

Compounds of formula XXXI can e.g. be prepared by treatment of compounds of formula XXX (compound of formula I where Y=S) with 2 to 2.5 equivalent of 3-chloroperoxybenzoic acid (mCPBA) and 4 to 5 equivalent of NaHCO$_3$ in a solvent such as methylene chloride at temperatures ranging from 0° C. to room temperature preferably 0° C. during 1 hour to 3 hours. The N-oxide which is formed on the dimethylamino group of the sugar residue during the reaction is reduced at work-up by treating the organic phase with a aqueous solution of sodium pyrosulfite at room temperature during 5 minutes to 24 hours to give the desired compounds of formula XXXI. Alternatively, if appropriate, the N-oxide is reduced by catalytic hydrogenation according to standard procedures. Compounds of formula XXXI can be further oxidised as described above but at room temperature during 1 to 48 hours to give, after reduction of the N-oxide, compounds of formula Id. Compounds Ir can also be obtained in one step from compounds of formula XXII by using 3,5 to 10 equivalent of the oxidising agent and 7 to 20 equivalent of NaHCO$_3$ at temperatures ranging from 0° C. to room temperature during 5 to 48 hours followed by the workup procedure described above (Scheme 11).

In the case where Q is further substituted with oxidation sensitive substituents like amino groups, these substituents might need to be protected before submitting the sulfide Ia to oxidation. Suitable protecting groups commonly known in the art can be introduced according to standard procedures described in T. W. Green et al., Protective Groups in Organic Synthesis, John Wiley & Sons, 1999. After oxidation, the protecting group can be removed following standard procedures also described in T. W. Green et al.

Green et al., Protective Groups in Organic Synthesis, John Wiley & Sons, 1999. If compounds of formula I or of formula XXI carry protecting groups on R1 a deprotection step according to methods well known in the art as described e.g. in T. W. Green et al., Protective Groups in Organic Synthesis, John Wiley & Sons, 1999 will be necessary to give the final compound.

It is further understood that R1 in compounds of e.g. formula I or I-A, and of intermediates like those mentioned above can be further modified. For example an ester group can be hydrolyzed and the resulting acid can be coupled with an amine to form a amide according to methods well known in the art.

The following examples are given to further illustrate the invention and are not to be construed as in any way limiting the scope of the present invention.

A. EXAMPLES

General remarks: MS spectra are measured using (A) a Micromass Waters ZQ system with Masslynx software and (B) using a Q-T of-Ultima (Waters AG) equipped with the Waters Cap-LC. For accurate mass determination the nano lock mass ESI source is used. Accurate masses are given with four decimal digits. Analytical HPLC: System Aa: column:

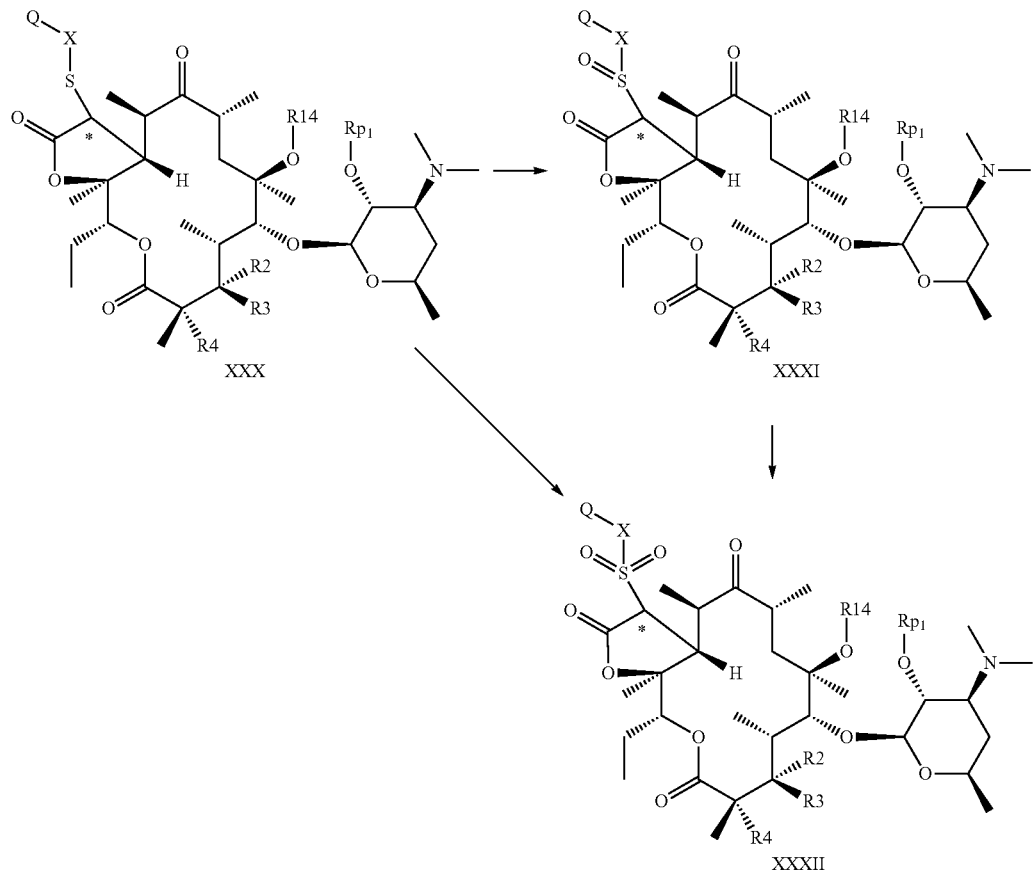

Scheme 11

In certain cases it may be necessary to protect functional groups on R1 and or R14 with protecting groups. Suitable protecting groups commonly known in the art can be introduced according to standard procedures described in T. W.

Inertsil ODS-3V, 5 μm, 250×4 mm; flow: 1.0 mL/min; detection: 254 nm; mobile phase A: water; mobile phase B: acetonitrile; gradient: 0-5 min constant 5% acetonitrile; 5-25 min linear from 5% to 95% acetonitrile. System Ba: Instrument:

Varian Prostar 210; column: Inertsil ODS-3V, 5 µm, 250×4 mm; flow: 1.0 mL/min; detection: 254 nm; column temp: 35° C.; mobile phase A: water+0.1% HCOOH; mobile phase B: acetonitrile+0.1% HCOOH; gradient: 0-5 min constant 5% B; 5-20 min linear from 5% to 95% B. System Ca: column: Agilent ZORBAX Eclipse plus C18, 5 µm, 250×4.6 mm; flow: 1.0 mL/min; detection: 220 nm; mobile phase A: water/acetonitrile/TFA 98.9/1/0.1 (v/v/v); mobile phase B: water/acetonitrile/TFA 1/98.9/0.1 (v/v/v); gradient: 0-5 min constant 0% B; 5-45 min linear from 0% to 100% B; 45-55 min 100% B. Preparative HPLC purification of final products is done using the following systems: System Ap: Column: YMC ODS-AQ, 120A, 5 µm, 50×20 mm; precolumn: YMC ODS-AQ, 120A, 5 µm, 10×20 mm; flow: 30 ml/min; injection: 500 µA; detection: ELSD; mobile phase A: water+0.1% HCOOH; mobile phase B: acetonitrile; gradient: linear form 10 to 95% acetonitrile in 4 min. System Bp: Column: Purospher STAR RP18e, 5 µm, 125×25 mm flow: 25 mL/min; detection: 254 nm; mobile phase A: water 25 mM ammonium formiate; mobile phase B: methanol; gradient: linear form 60% to 90% methanol in 10 min. System Cp: Column: Purospher STAR RP18e, 5 µm, 125×25 mm flow: 25 mL/min; detection: 254 nm; mobile phase A: water 25 mM ammonium formiate; mobile phase B: acetonitrile; gradient: linear form 20% to 50% acetonitirile in 10 min. Abbreviations: HPLC for high performance liquid chromatography; DMSO for dimethylsulphoxide; DBU for diazabicycloundecane; DCM for dichloromethane; DIPEA for diisopropylethylamine (Huenig's base); DMF for dimethylformamide; THF for tetrahydrofurane; DCC for dicyclohexylcarbodiimide; DMAP for 4-dimethylaminopyridine; EDC•HCl for N-(3-dimethylaminopropyl)-N'-ethylcarbodiimide hydrochloride; HOBt for 1-hydroxy-benzotriazol; HATU for 2-(1H-Azabenzotriazol-1-yl)-1,1,3,3-tetramethyluronium hexafluorophosphate; mCPBA for m-Chloroperbenzoic acid; KOtBu for potassium tent.-butylate; TBDMSCl for tert-butyl-dimethyl-silylchloride, TBAF for tetrabutylammoniumfluoride, MS for mass spectrometry; NMR for nuclear magnetic resonance; ESI for electrospray ionization.

| Example | |
|---|---|
| 1 | 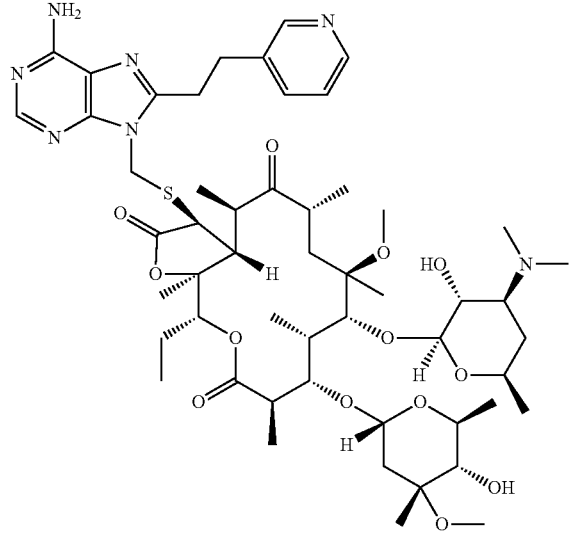 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCn3c(CCc4cccnc4)nc4c(N)ncnc43)C(=O)O[C@@]21C] |
| 2 | 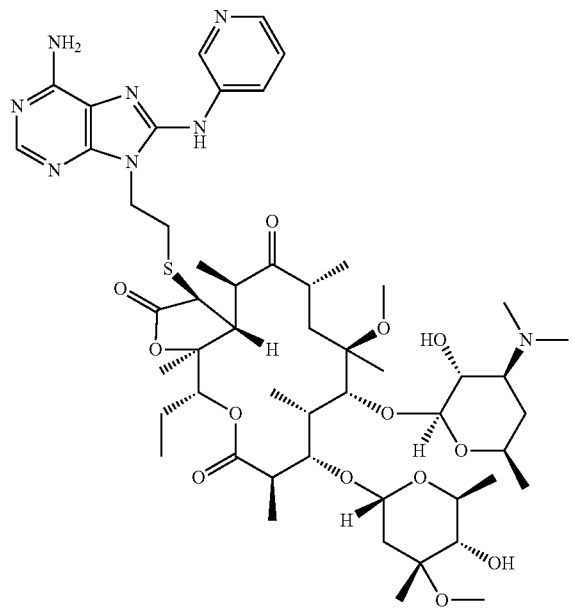 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCn3c(Nc4cccnc4)nc4c(N)ncnc43)C(=O)O[C@@]21C] |

| Example | |
|---|---|
| 3 | 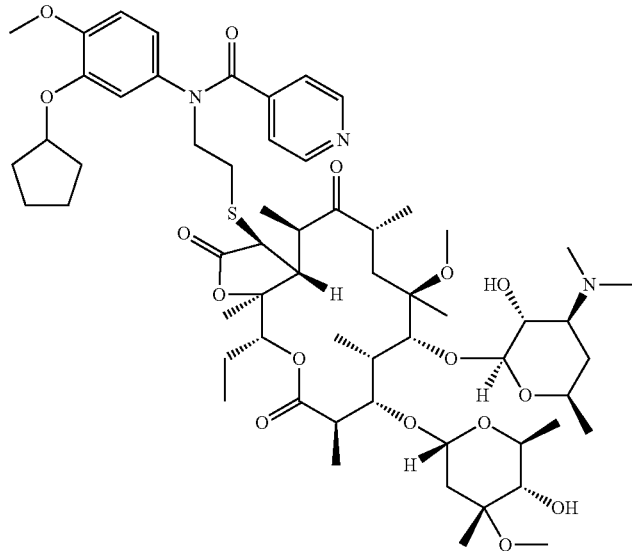 |
| 4 | 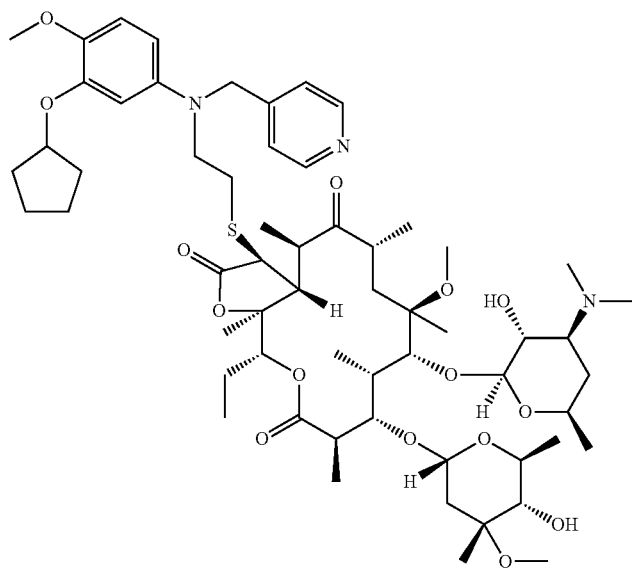 |

-continued
| Example | |
|---|---|
| 5 | 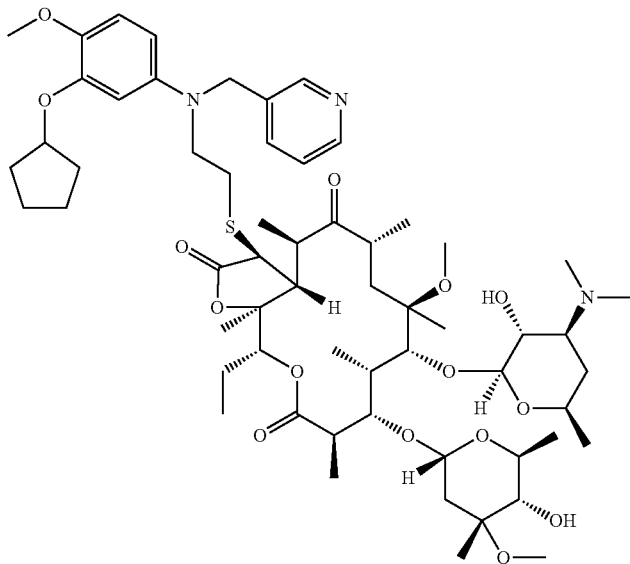 |
| 6 | 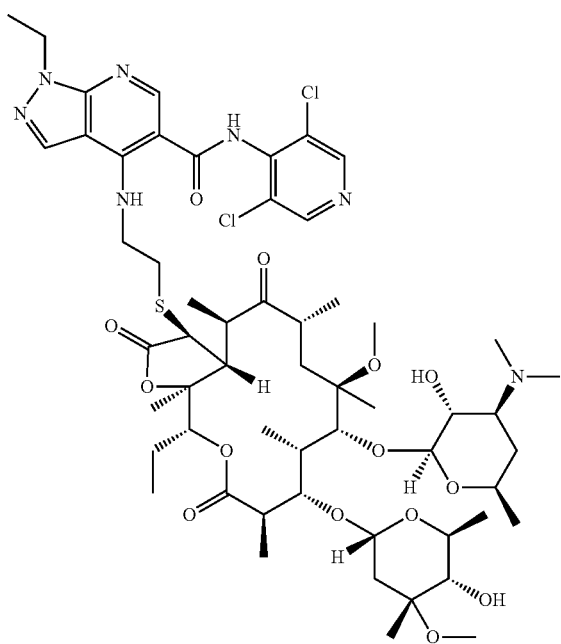 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCNc3c(C(=O)Nc4c(Cl)cncc4Cl)cnc4c3cnn4CC)C(=O)O[C@@]21C] |

| Example | |
|---|---|
| 7 | 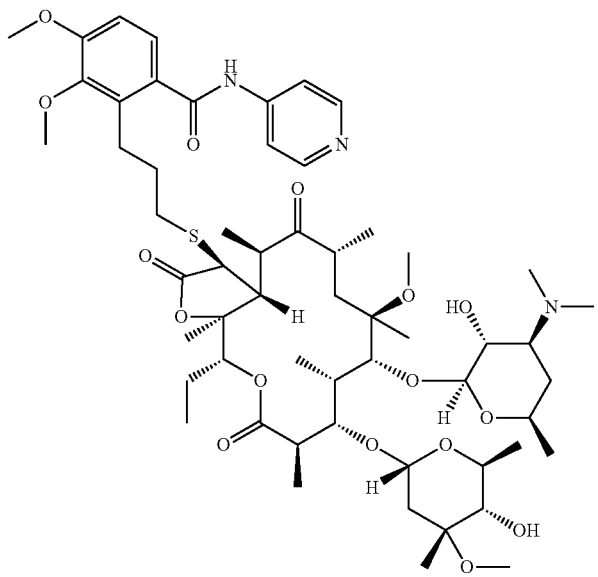 |
| 8 | 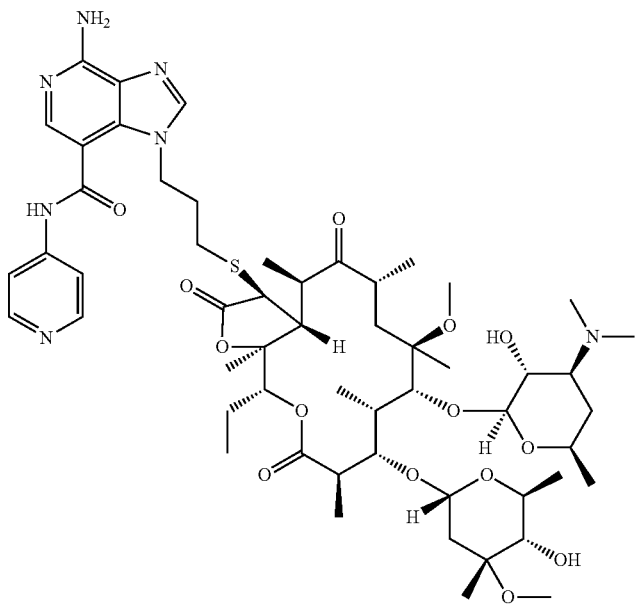 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCCn3cnc4c(N)ncc(C(=O)Nc5ccncc5)c43)C(=O)O[C@@]21C] |

| Example | |
|---|---|
| 9 | 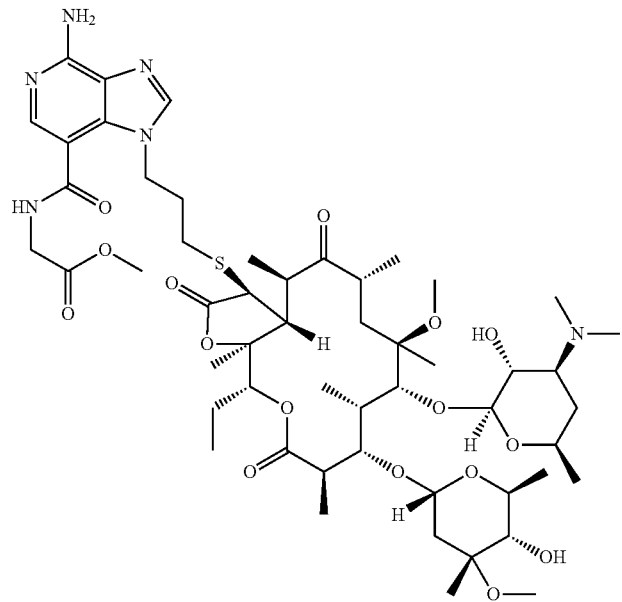 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCCn3cnc4c(N)ncc(C(=O)NCC(=O)OC)c43)C(=O)O[C@@]21C] |
| 10 | 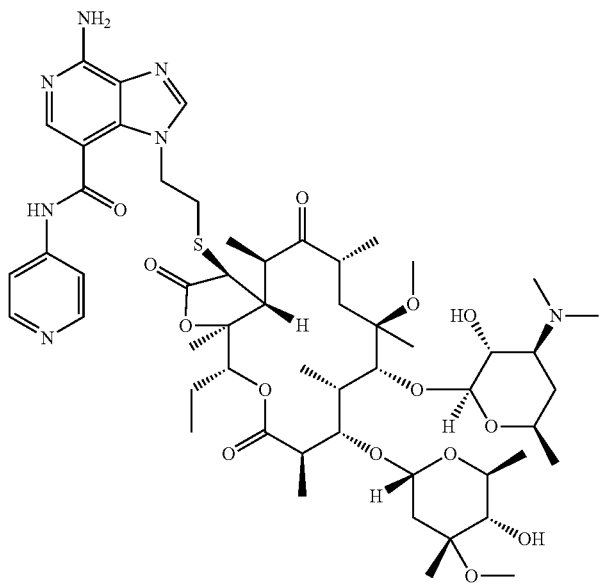 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCn3cnc4c(N)ncc(C(=O)Nc5ccncc5)c43)C(=O)O[C@@]21C] |

| Example | |
|---|---|
| 11 | 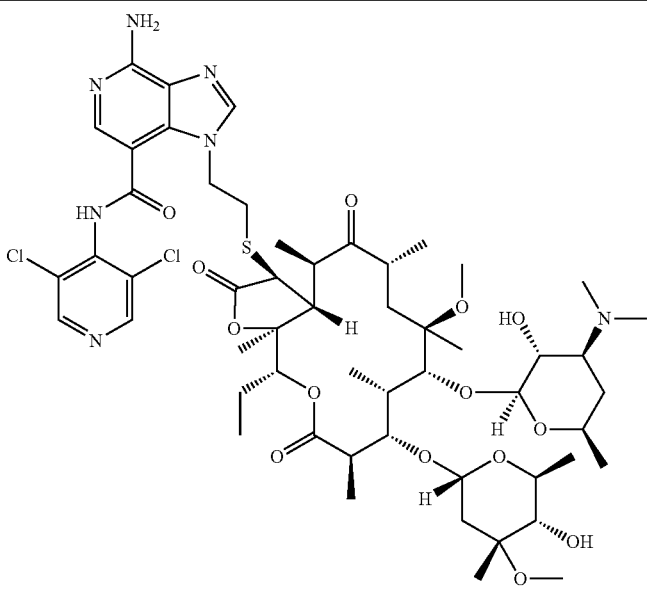 |
| 12 | 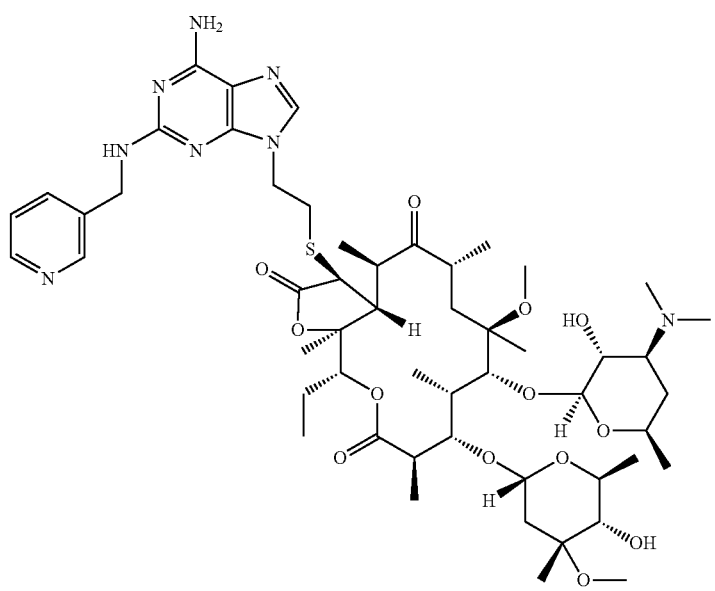 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCn3cnc4c(N)nc(NCc5cccnc5)nc43)C(=O)O[C@@]21C] |

| Example | |
|---|---|
| 13 | 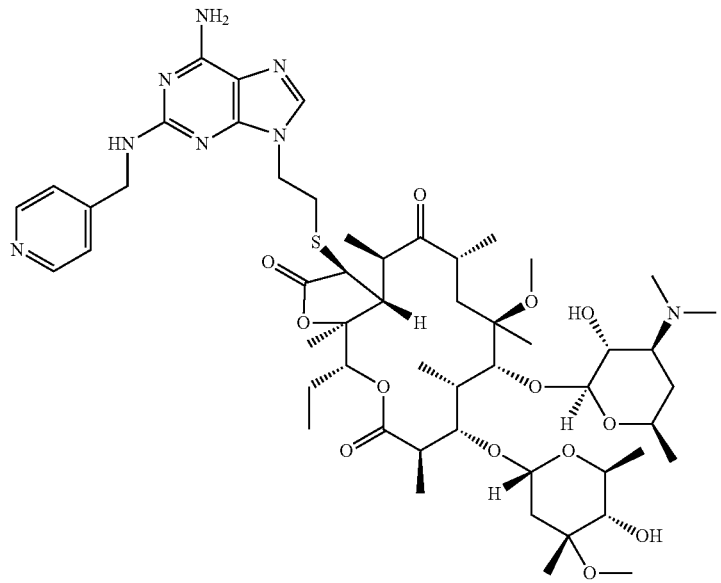 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCn3cnc4c(N)nc(NCc5ccncc5)nc43)C(=O)O[C@@]21C] |
| 14 | 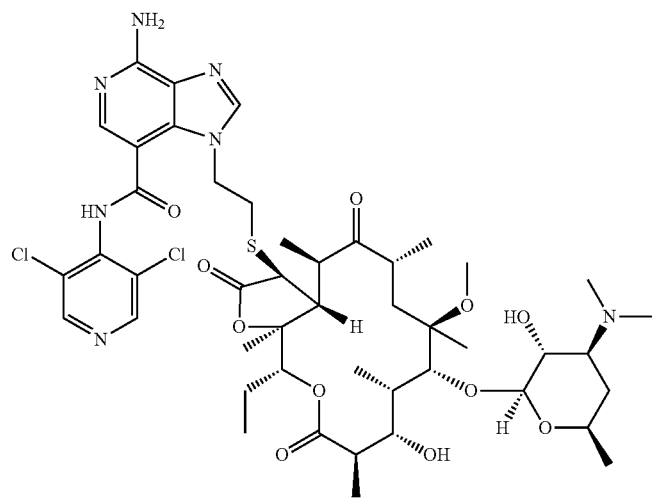 [SMILES: CC[C@H]1OC(=O)[C@H](C)[C@@H](O)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCn3cnc4c(N)ncc(C(=O)Nc5c(Cl)cncc5Cl)c43)C(=O)O[C@@]21C] |
| 15 | 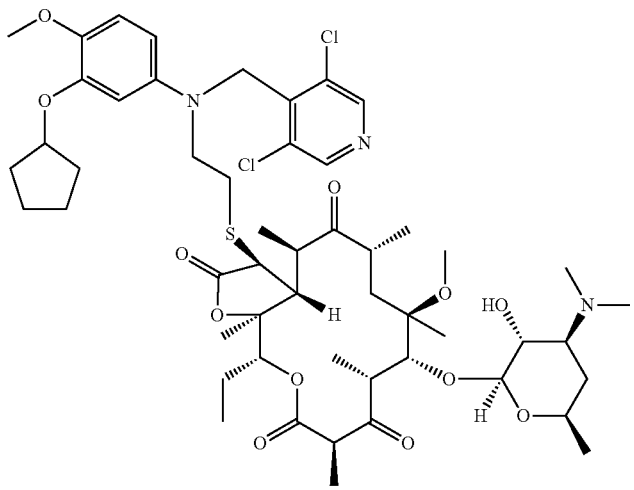 |

| Example | |
|---|---|
| 16 | 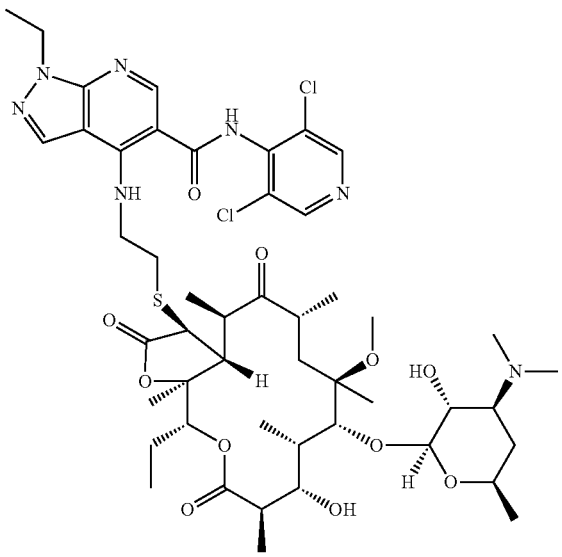 [SMILES: CC[C@H]1OC(=O)[C@H](C)[C@@H](O)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCNc3c(C(=O)Nc4c(Cl)cncc4Cl)cnc4c3cnn4CC)C(=O)O[C@@]21C] |
| 17 | 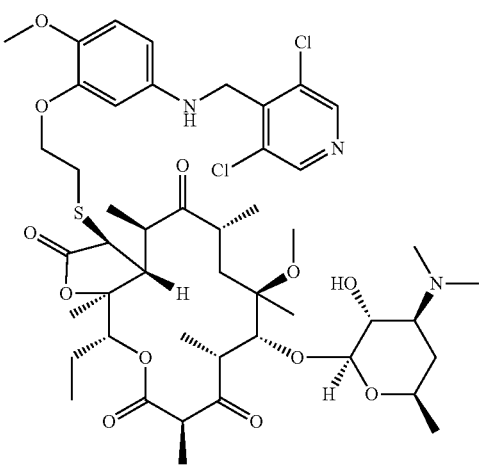 |
| 18 | 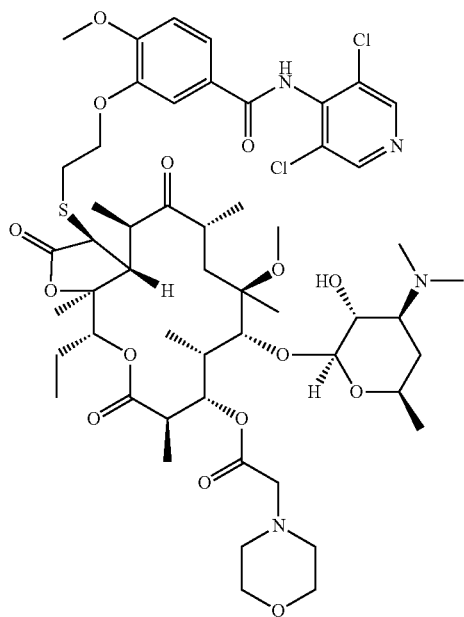 [SMILES: CC[C@H]1OC(=O)[C@H](C)[C@@H](OC(=O)CN2CCOCC2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCOc3cc(C(=O)Nc4c(Cl)cncc4Cl)ccc3OC)C(=O)O[C@@]21C] |

| Example | |
|---|---|
| 19 | 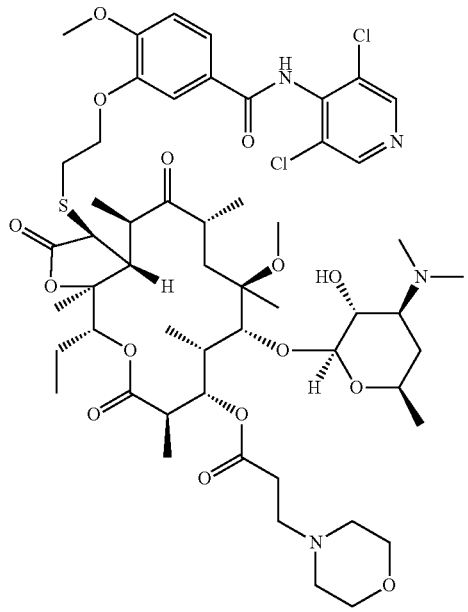 [SMILES: CC[C@H]1OC(=O)[C@H](C)[C@@H](OC(=O)CCN2CCOCC2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SCCOc3cc(C(=O)Nc4c(Cl)cncc4Cl)ccc3OC)C(=O)O[C@@]21C] |

Example 1

Preparation of I-1, compound of formula I-A where R1 is [2-[6-Amino-8-(2-pyridin-3-yl-ethyl)-purin-9-yl]ethyl]thio, R12 and R13 taken together form a C=O group and R14 is methyl.

A] Preparation of 2-(6-amino-8-bromo-purin-9-yl)ethanol

To a solution of 10 g 2-(6-amino-purin-9-yl)ethanol in 200 ml 0.5M AcONa/AcOH buffer pH 4 are added 4 ml of $Br_2$. The resulting mixture is stirred at room temperature for 8 hours. The precipitated product is isolated, washed with water and crystallized from ethanol to give 6.13 g (43%) of the desired compound.

B] Preparation of 2-(6-amino-8-(2-pyridin-3-yl-ethynyl)-purin-9-yl) ethanol

To a solution of 258 mg of 2-(6-amino-8-bromo-purin-9-yl)ethanol in a mixture of $Et_3N$ and DMF is added under an atmosphere of argon 35 mg of $Pd(PPh)_3Cl_2$, 19 mg CuI and 150 mg 3-ethynylpyridine. The mixture is stirred under argon at 60° C. for 3 hours and over night at room temperature. The precipitate is isolated, washed with water and hot ethanol and dried to give 150 mg (53%) of the desired product.

C] Preparation of 2-(6-amino-8-(2-pyridin-3-yl-ethyl)-purin-9-yl)ethanol

To a suspension of 1.1 g of 2-(6-amino-8-(2-pyridin-3-yl-ethynyl)-purin-9-yl)ethanol in 400 ml methanol are added 2.0 g of Raney-nickel and the mixture is hydrogenated (4 atm) at 80° C. during 6 hours. After completion of the reaction the catalyst is removed and the solvent is evaporated. The crude product is purified by column chromatography on silica gel ($CHCl_3$:MeOH 9:1) to give 0.45 g (41%) of the desired product.

D] Preparation of 6-amino-9-(2-chloroethyl)-8-(2-pyridin-3-yl-ethyl)-purine 0.45 g of 2-(6-amino-8-(2-pyridin-3-yl-ethyl)-purin-9-yl) ethanol are cooled to −20° C. and 6 ml of $SOCl_2$ are added. The temperature is gradually risen to 50° C. and the mixture is stirred at this temperature for 12 hours. The excess of $SOCl_2$ is evaporated and the residue is taken up in dichloromethane washed with saturated aqueous $NaHCO_3$ dried over $Na_2SO_4$ and evaporated in vacuo. The crude product is purified by flash chromatography on silica gel ($CHCl_3$: MeOH 50:1) to give 40 mg (8%) of the desired product.

$^1$H-NMR (DMSO-$d_6$): 8.65 (s, 1H); 8.4 (s, 1H); 8.1 (s, 1H); 7.75 (d, 1H); 7.30 (m, 1H); 6.95 (s, 2H, —$NH_2$); 4.45 (t, 2H); 4.0 (t, 2H).

E] Preparation of compound of formula II where $Rp_1$ and $Rp_2$ are acetyl and R14 is methyl (II-1)

To a solution of 25 g (33.4 mmol) clarithromycin and 1.63 g (13.4 mmol) DMAP in 50 ml DCM are added 11 ml (117 mmol) acetic anhydride in one portion and the mixture is stirred for 20 h at room temperature. The reaction mixture is poured into enough 0.2 N NaOH to get a pH value of 8-9 and then extracted. The combined organic layers are washed with water and brine, dried over $MgSO_4$ and evaporated under reduced pressure. The crude product is crystallised from hot ethyl acetate to give 24.3 g (87%) of colorless crystals. MS (ESI): 832.5 [MH]$^+$ F] Preparation of compound of formula III where $Rp_1$ and $Rp_2$ are acetyl and R14 is methyl (III-1)

24.3 g (29.2 mmol) of 2',4"-di-O-acetyl-6-O-methylerythromycin A (II-1) are dissolved in 500 ml THF at −45° C. under argon and treated dropwise with 29.2 ml of a 1 M solution of sodium bis(trimethylsilyl)amide in tetrahydrofurane (29.2 mmol) over 15 min. After 20 min. at −45° C. 16.24 g (100.1 mmol) carbonyldiimidazole are added in 3 portions over 5 min. The reaction mixture is stirred at −45° C. for 30 min, then warmed to 0° C. over a period of 15 min and kept at 0° C. for 2.5 hours.

The reaction mixture is treated with a saturated aqueous solution of $NaHCO_3$ and water (1:1) and extracted twice with ethyl acetate. The combined organic layers are washed twice with 10% aqueous ammonia solution, with brine, dried over sodium sulfate and evaporated under reduced pressure to afford 23.57 g (94%) of a colorless solid. MS (ESI): 858.6 [MH]$^+$.

G] Preparation of compound of formula IV where Rp$_1$ and Rp$_2$ are acetyl and R14 is methyl (IV-1)

23.5 g (27.47 mmol) of compound III-1 and 10.25 ml (68.7 mmol) DBU dissolved in 500 ml toluene are heated at reflux temperature for 1.5 h, cooled to room temperature and poured into 0.5 M aqueous NaH$_2$PO$_4$. The aqueous layer is extracted twice with ethyl acetate. The combined organic extracts are washed with 0.5 M NaH$_2$PO$_4$, brine, dried over Na$_2$SO$_4$ and concentrated to give 18.43 g (86%) of a colourless solid. MS (ESI): 814.5 [MH]$^+$.

H] Preparation of compound of formula V where Rp$_1$ and Rp$_2$ are acetyl and R14 is methyl (V-1)

To a solution of 64.0 g (78.6 mmol) of compound IV-1, 3.84 g (31.4 mmol) 4-dimethylaminopyridine and 12.5 g of pyridine in 600 ml dichloromethane is added dropwise a solution of 26.9 g of chloroacetic acid anhydride (157.3 mmol) in 250 ml dichloromethane over 2 hours under nitrogen. The solution is stirred at room temperature for 3.5 hours. The reaction mixture is poured into 0.2N NaOH to get to a pH value of 8-9 and extracted twice with dichloromethane. The combined organic layers are washed successively with water, twice with 0.5N NaH$_2$PO$_4$, with water and twice with brine, dried over Na$_2$SO$_4$ and evaporated to give crude product. Petroleum ether is added to the crude product, the mixture is stirred for 3 hours at room temperature and filtered to give the title compound (57.5 g, 82%) as a light brownish solid. MS (ESI): 890.3.

I] Preparation of compound of formula VI where R1 is [(4-methoxyphenyl)methyl]thio and Rp$_1$ and Rp$_2$ are acetyl and R14 is methyl (VI-1)

10.5 g of compound V-1 are dissolved under argon in 180 ml acetone and 2.42 g DBU, 20 mg sodium iodide and 2.20 g (4-methoxyphenyl)methanethiol are added in one portion. The reaction mixture is stirred under argon at room temperature for 2.5 hours. 250 ml of DCM are added to the reaction mixture. The organic layer is washed three times with 5% NaHCO$_3$, dried over Na$_2$SO$_4$ and evaporated in vacuo to give 11.7 g (98.4%) of a light brown foam. MS (ESI): 1008.4.

K] Preparation of compound of formula VII where R1 is [(4-methoxyphenyl)methyl]thio and Rp$_1$ and Rp$_2$ are acetyl and R14 is methyl (VII-1)

6.00 g of compound of VI-1 are dissolved under nitrogen in 60 ml DMF and cooled with an ice bath. 0.39 g sodium hydride oil dispersion (60%) are added and the mixture is stirred during 3 hours at 0-5° C. Now aqueous KH$_2$PO$_4$ 0.5N are added and the mixture is extracted with 100 ml diethylether. The organic layer is washed three times with 60 ml aqueous NaHCO$_3$ 3% and with 80 ml brine, dried over Na$_2$SO$_4$ and evaporated in vacuo to afford 4.65 g crude product. MS (ESI): 1008.4 [MH]$^+$.

L] Preparation of compound of formula I-A where R1 is [(4-methoxyphenyl)methyl]thio, R12 and R13 taken together form a C=O group and R14 is methyl 21.8 g (21.6 mmol) of crude compound VII-1 are dissolved in 290 ml methanol and 16.2 ml (108.3 mmol) DBU are added. The mixture is heated to reflux under argon for 5 hours. The solvent is evaporated under reduced pressure and the residue is taken up in 580 ml DCM. The organic layer is washed twice with water and with brine, dried over Na$_2$SO$_4$ and evaporated in vacuo. The crude product is washed with petroleum ether/diethylether 5/1. The residue is dissolved in 150 ml methanol and 55 ml of water are added. The mixture is stirred during 2 hours and the product is isolated by filtration to afford 11.1 g (41%) of the title compound as a solid. MS (ESI): 924.4.

M] Preparation of compound of formula VIIa where Rp$_1$ is (4-methoxyphenyl)methyl and Rp$_1$ is acetyl, Rp$_2$ is hydrogen and R14 is methyl (VIIa-1)

2.0 g (2.16 mmol) of the product of example 1 step L are dissolved in 50 ml DCM and 0.22 ml (2.4 mmol) acetic anhydride are added. The mixture is stirred at room temperature for 48 hours. The solution is washed with aqueous NaHCO$_3$ (5%) and brine, dried over Na$_2$SO$_4$, filtered and concentrated in vacuo to give 2.17 g of a light brown foam. The crude product is used without purification for the next step. MS (ESI): 967.3 [MH]$^+$.

N] Preparation of compound of formula IX where Rp$_4$ is methyl, Rp$_1$ is acetyl, Rp$_2$ is hydrogen and R14 is methyl (IX-1)

2.17 g (2.25 mmol) of VIIa-1 are dissolved in 50 ml DCM and molecular sieves is added. 880 mg (4.49 mmol) dimethyl (methylthio) sulfonium tetrafluoroborate are added to the mixture and the reaction is stirred for 5 hours at room temperature. The reaction mixture is filtered and washed twice with 20 ml aqueous NaHCO$_3$ (5%) and brine, dried over Na$_2$SO$_4$, filtered and concentrated in vacuo to give 1.62 g of a light brown foam. The crude product is used without purification for the next step. MS (ESI): 893.1 [MH]$^+$.

O] Preparation of compound of formula VII where R1 is [2-[6-amino-8-(2-pyridin-3-yl-ethyl)-purin-9-yl]ethyl]thio, Rp$_1$ is acetyl, Rp$_2$ is hydrogen and R14 is methyl (VII-1)

To a solution of 0.120 g (0.13 mmol) of the product of example 1 step N dissolved in 4 ml DMF and 1 drop of water, 66.4 μl (0.27 mmol) of tributylphosphine are added and the mixture is stirred for 30 min at room temperature. Then 44.8 mg (0.15 mmol) of 6-amino-9-(2-chloroethyl)-8-(2-pyridin-3-yl-ethyl)-purine and 40.2 μl DBU (0.27 mmol) are added to the solution. The reaction is stirred over night at room temperature and concentrated in vacuo and the residue is taken up in DCM. The organic layer is washed with aqueous NaHCO$_3$ (5%) and brine, dried over Na$_2$SO$_4$, filtered and concentrated in vacuo to give the crude product. The crude product is purified by flash chromatography on silica gel (DCM/MeOH/NH$_3$ 99:1:0.01→95:5:0.01) to give 57 mg (38%) of the desired product. MS (ESI): 1112.6 ([MH]$^+$), 577.0 ([MH$_2$]$^{++}$).

P] Preparation of compound of formula I where R1 is [2-[6-Amino-8-(2-pyridin-3-yl-ethyl)-purin-9-yl]ethyl]thio, R2 is Cladinosyl, R3 and R4 are hydrogen, R12 and R13 taken together form a C=O group and R14 is methyl (I-1)

The product of example 1 step O (54 mg) is dissolved in 2 ml methanol and stirred for 96 hours at room temperature. Then reaction mixture is concentrated in vacuo and the residue is purified by HPLC to afford the desired product as a white solid.

MS: accurate mass (ESI): 1069.5792 Da.

Example 2

Preparation of I-2, compound of formula I-A where R1 is [2-[6-Amino-8-(pyridin-3-ylamino)-purin-9-yl]ethyl]thio, R12 and R13 taken together form a C=O group and R14 is methyl.

A] Preparation of 6-amino-8-bromo-9-[2-(tert-butyl-dimethyl-silanyloxy)-ethyl]-purine To a solution of 3.0 g of 2-(6-amino-8-bromo-purin-9-yl) ethanol (example 1, step A) in 30 ml DMF are added 2.8 g TBDMSCl and 1.1 g imidazole and the mixture is stirred for 24 hours under argon at 20° C. The precipitate is filtered off, washed with water and dried to give 3.6 g (84%) of the desired product.

B] Preparation of 6-amino-8-(pyridin-3-ylamino)-9-[2-(tert-butyl-dimethyl-silanyloxy)ethyl]-purine To a solution of 0.372 g of the product of example 2, step A and 0.23 g 3-aminopyridine in 10 ml toluene are added 0.091 g $Pd_2(dba)_3$, 0.14 g t-BuONa and 0.087 g 9,9-dimethyl-4,5-bis(diphenylphosphino)xanthene (Xantphos). The mixture is stirred at 100° C. under an atmosphere of argon during 16 hours. After completion of the reaction the mixture is diluted with water and extracted with DCM. The organic layer is concentrated and the crude product is purified by flash chromatography on silica gel ($CHCl_3$:MeOH 20:1) to afford 0.1 g (26%) of the desired product.

C] Preparation of 2-(6-amino-8-(pyridin-3-ylamino)-purin-9-yl)ethanol

To a solution of 0.46 g of the product of example 2, step B in 10 ml THF are added 0.12 g of $TBAF*3H_2O$ and the mixture is stirred during 16 hours at 20° C. The reaction mixture is subsequently concentrated and the crude product is purified by flash chromatography on silica gel (ethyl acetate: methanol 20:1) to afford 0.19 g (59%) of the desired product.

D] Preparation of 6-amino-9-(2-chloroethyl)-8-(pyridin-3-ylamino)-purine 0.11 g of 2-(6-amino-8-(pyridin-3-ylamino)-purin-9-yl) ethanol are cooled to −20° C. and 2 ml of $SOCl_2$ are added. The temperature is gradually risen to 50° C. and the mixture is stirred at this temperature for 12 hours. The excess of $SOCl_2$ is evaporated and aqueous ammonia is added to the residue. The mixture is extracted with ethyl acetate. The organic layer is separated and evaporated. The crude product is purified by flash chromatography on silica gel (ethyl acetate:MeOH 20:1) to give 30 mg (27%) of the desired product. $^1$H-NMR (DMSO-$d_6$): 9.10 (s, 1H); 9.0 (s, 1H); 8.35 (d, 1H); 8.20 (d, 1H); 8.05 (s, 1H); 7.30 (m, 1H); 6.65 (s, 2H, —$NH_2$); 4.55 (t, 2H); 4.0 (t, 2H).

E] Preparation of compound of formula I where R1 is [2-[6-Amino-8-(pyridin-3-ylamino)-purin-9-yl]ethyl]thio, R12 and R13 taken together form a C=O group and R14 is methyl (I-2)

The title compound I-2 is prepared starting from 6-amino-9-(2-chloroethyl)-8-(pyridin-3-ylamino)-purine and IX-1 following the procedures described in example 1 steps O-P.

MS: accurate mass (ESI): 1056.5548 Da.

Example 3

Preparation of I-3, compound of formula I-A where R1 is [2-[(3cyclopentyloxy-4-methoxy-phenyl)-(pyridin-4-yl-carbonyl)-amino]ethyl]thio, R12 and R13 taken together form a C=O group and R14 is methyl.

A] Preparation of N-(3-cyclopentyloxy-4-methoxy-phenyl)-isonicotinamide 7.0 g (33.8 mmol) of 3-cyclopentyloxy-4-methoxy-phenylamine (Garcia et al., JOC, 2005, 70, p 1050) are dissolved in 150 ml of DCM. The solution is cooled to 0° C. and 5.74 g (40.5 mmol) isonicotinoyl chloride in 50 ml DCM are added to the solution. A precipitate is formed. The reaction mixture is subsequently stirred at room temperature during two hours. A solution of 2.7 g NaOH in 100 ml water is added to the reddish reaction mixture. The organic layer is separated, dried over $Na_2SO_4$ and evaporated. The crude product is purified by flash chromatography on silica gel (ethyl acetate/n-hexane 2:1) to afford 7.2 g (62%) of the desired product. MS (ESI): 313.1.

B] Preparation of N-(2-chloroethyl)-N-(3-cyclopentyloxy-4-methoxy-phenyl)-isonicotinamide 3.0 g (9.6 mmol) of the product of example 3 step A are dissolved in 50 ml 1-bromo-2-chloroethane and 5.33 g (95 mmol) of potassium hydroxide are added to the solution. The reaction mixture is stirred at room temperature over night and then heated to 60° C. for four hours. The reaction mixture is cooled to room temperature and 50 ml water are added. The mixture is extracted with 50 of DCM. The organic layer is washed with water and brine, dried over $Na_2SO_4$ and evaporated. The crude product is purified by flash chromatography on silica gel (ethyl acetate/n-hexane 1:1) to afford 1.3 g (43%) of the desired product as a yellow oil. $^1$H-NMR (DMSO-$d_6$): 8.45 (d, 2H); 7.21 (d, 2H); 6.8 (m, 3H); 4.63 (m, 1H); 4.13 (t, 2H); 3.76 (t, 2H); 3.66 (s, 3H); 1.4-1.8 (m, 8H).

C] Preparation of compound of formula I-A where R1 is [2-[(3cyclopentyloxy-4-methoxy-phenyl)-(pyridin-4-yl-carbonyl)-amino]ethyl]thio, R12 and R13 taken together form a C=O group and R14 is methyl (I-3)

The title compound I-3 is prepared starting from N-(2-chloroethyl)-N-(3-cyclopentyloxy-4-methoxy-phenyl)-isonicotinamide and IX-1 following the procedures described in example 1 steps O-P.

MS: accurate mass (ESI): 1141.6073 Da.

Example 4

Preparation of I-4, compound of formula I-A where R1 is [2-[(3-cyclopentyloxy-4-methoxy-phenyl)-(pyridin-4-ylm-ethyl)-amino]-ethyl]thio, R12 and R13 taken together form a C=O group and R14 is methyl.

A] Preparation of (3-cyclopentyloxy-4-methoxy-phenyl)-(pyridin-4-ylmethyl)-amine 0.5 g (1.6 mmol) of the product of example 3 step A is dissolved under nitrogen in 20 ml dry THF and 0.24 g (6.4 mmol) lithium aluminium hydride are added at room temperature. The reaction mixture is stirred for two hours at room temperature and then cooled to 0° C. and 2 ml of water are added. The mixture is extracted with 3×20 ml of ethyl acetate. The combined organic layers are washed with water and brine, dried over $Na_2SO_4$ and evaporated in vacuo to give the crude product as an oil. The crude product is purified by flash chromatography on silica gel (ethyl acetate/n-hexane 1:1) to afford 0.4 g (84%) of the desired product as an oil. MS (ESI): 299.2 ([MH]$^+$).

B] Preparation of (2-chloro-ethyl)-(3-cyclopentyloxy-4-methoxy-phenyl)-(pyridin-4-ylmethyl)-amine 3.85 g (12.9 mmol) of the product of example 4 step A are dissolved in 50 ml methanol at 25° C. and 5.1 ml of a solution of chloroacetaldehyde (40% in water; 77.4 mmol, 6 eq), 4.86 g (77.4 mmol, 6. eq) of sodium cyano borohydride and 0.74 ml (12.9 mmol) of acetic acid are added. The mixture is stirred at 25° C. for 16 hours. Then the solvent is removed under reduced pressure and the residue is taken up in 100 ml dichloromethane. The mixture is washed with 3×50 ml brine, dried over $Na_2SO_4$ and evaporated in vacuo. The crude product is purified by flash chromatography on silica gel (ethyl acetate/n-hexane 1:4) to afford 1.66 g (35%) of the desired product as an oil.

MS (ESI): 361.2, 363.1 ([MH]$^+$).

$^1$H-NMR (CDCl$_3$): 8.52 (d, 2H); 7.17 (d, 2H); 6.75 (d, 1H); 6.18-6.24 (m, 2H); 4.6 (m, 1H); 4.52 (s, 2H); 3.75 (s, 3H); 3.64-3.73 (m, 4H); 1.5-1.9 (m, br, 8H).

C] Preparation of compound of formula IX where $Rp_4$ is methyl, $Rp_1$ and $Rp_t$ are hydrogen and R14 is methyl (IX-4)

3.1 g (3.35 mmol) of the product of example 1 step L are dissolved in 80 ml DCM and molecular sieves is added. 1.0 g (4.94 mmol) dimethyl(methylthio) sulfonium tetrafluoroborate are added to the mixture and the reaction is stirred for 20 hours at room temperature. The reaction mixture is filtered and the filtrate is washed twice with 80 ml aqueous NaHCO$_3$ (5%), 80 ml water and 80 ml brine, dried over Na$_2$SO$_4$, filtered and concentrated in vacuo to give 3.04 g of a light brown foam. The crude product is used without purification for the next step.

MS (ESI): 850.2 [MH]$^+$.

D] Preparation of compound of formula I-A where R1 is [2-[(3-cyclopentyloxy-4-methoxy-phenyl)-(pyridin-4-ylmethyl)-amino]-ethyl]thio, R12 and R13 taken together form a C=O group and R14 is methyl. (I-4)

To a solution of 0.136 g (0.16 mmol) of the product of example 4 step C dissolved in 7.5 ml DMF and 35 µl of water, 80 µl (0.32 mmol) of tributylphosphine are added and the mixture is stirred at room temperature until no starting material remained (3 hours). Then 45 mg (0.24 mmol) of the product of example 4 step B and 36 µl DBU (0.24 mmol) are added to the solution. The reaction is stirred for 13 hours at room temperature and then 15 ml of water are added and the mixture is extracted with 3×20 ml ethyl acetate. The combined organic layers are concentrated, dried over Na$_2$SO$_4$, filtered and concentrated in vacuo to give the crude product as yellow oil. An initial purification of the product is done by flash chromatography on silica gel (ethyl acetate/hexane 5/1). The compound is further purified by preparative HPLC (column: Xterra C18(5 µm) 100 mm×10 mm; mobile phase A: water+0.02% NH$_4$OH, mobile phase B: MeOH; flow rate: 10 ml/min; detection: 254 nm; gradient: 0 min/90% A/10% B, 10 min/40% A/60% B, 10.1 min/0% A/100% B).

MS: accurate mass (ESI): 1128.6423 Da.

Ret. Time: 10.8 min. (column: Prontosil 120-3-C18 SH 3 µm, 75×4.6 mm; flow: 1.0 mL/min; detection: 254 nm; column temp: rt; mobile phase A: water+0.1% TFA; mobile phase B: methanol; gradient: 0-5 min constant 30% B; 5-25 min linear from 30% to 95% B).

Example 5

Preparation of I-5, compound of formula I-A where R1 is [2-[(3-cyclopentyloxy-4-methoxy-phenyl)-(pyridin-3-ylmethyl)-amino]-ethyl]thio, R12 and R13 taken together form a C=O group and R14 is methyl.

A] Preparation of N-(3-cyclopentyloxy-4-methoxy-phenyl)-nicotinamide 3.2 g (14.3 mmol) of 3-cyclopentyloxy-4-methoxy-phenylamine (Garcia et al., JOC, 2005, 70, p 1050) are dissolved in 120 ml of DCM. The solution is cooled to 0° C. and 15 ml (107.6 mmol, 7.5 eq.) triethylamine and 3.7 g (26.1 mmol; 1.8 eq) nicotinoyl chloride in 50 ml DCM are added to the reaction mixture. The reaction mixture is stirred for 2 h and then a solution of 1.3 g NaOH in 50 ml water is added to the mixture. The organic phase is separated and washed with water and brine, dried over Na$_2$SO$_4$ and evaporated in vacuo. The crude product is purified by flash chromatography on silica gel (ethyl acetate/n-hexane 1:1) to afford 4 g (85%) of the desired product as a white solid.

MS (ESI): 313.0 ([MH]$^+$).

$^1$H-NMR (DMSO-d$_6$): 10.24 (s, 1H); 9.07 (s, 1H); 8.73 (d, 1H); 8.25 (d, 1H); 7.54 (dd, 1H); 7.42 (s, 1H); 7.29 (d, 1H); 6.91 (d, 1H); 4.70 (m, 1H); 3.71 (s, 3H); 1.56-1.90 (m, 8H).

B] Preparation of (3-cyclopentyloxy-4-methoxy-phenyl)-(pyridin-3-ylmethyl)-amine 0.5 g (1.6 mmol) of the product of example 5 step A is dissolved under nitrogen in 20 ml dry THF and 0.24 g (6.4 mmol) lithium aluminium hydride are added at 0° C. The reaction mixture is stirred for two hours at 15° C. and then cooled to 0° C. and 2 ml of water are added. The mixture is extracted with 3×20 ml of ethyl acetate. The combined organic layers are washed with water and brine, dried over Na$_2$SO$_4$ and evaporated in vacuo to give the crude product as an oil. The crude product is purified by flash chromatography on silica gel (ethyl acetate/n-hexane 1:1) to afford 180 mg (38%) of the desired product as a light yellow oil. MS (ESI): 299.1 ([MH]$^+$).

$^1$H-NMR (DMSO-d$_6$): 8.54 (s, 1H); 8.41 (d, 1H); 7.72 (d, 1H); 7.32 (dd, 1H); 6.64 (d, 1H); 6.22 (d, 1H); 6.02 (dd, 1H); 4.60 (m, 1H); 4.21 (s, 2H); 3.56 (s, 3H); 1.50-1.76 (m, 8H).

C] Preparation of (2-chloro-ethyl)-(3-cyclopentyloxy-4-methoxy-phenyl)-(pyridin-3-ylmethyl)-amine 150 mg (0.51 mmol) of the product of example 5 step B are dissolved in 10 ml methanol at 25° C. and 0.5 ml of a solution of chloroacetaldehyde (40% in water; 7.74 mmol, 15 eq), 0.25 g (3.98 mmol, 7.8 eq) of sodium cyano borohydride and 0.05 ml (0.87 mmol) of acetic acid are added. The mixture is stirred at 15° C. for 4 hours. Then the solvent is removed under reduced pressure and the residue is taken up in 100 ml dichloromethane. The mixture is washed with 3×50 ml brine, dried over Na$_2$SO$_4$ and evaporated in vacuo. The crude product is purified by flash chromatography silica gel (ethyl acetate/n-hexane 1:4) to afford 140 mg (35%) of the desired product as a light yellow oil. MS (ESI): 361.2, 363.1 ([MH]$^+$).

$^1$H-NMR (DMSO-d$_6$): 8.45 (s, 1H); 8.39 (d, 1H); 7.58 (d, 1H); 7.29 (dd, 1H); 6.72 (d, 1H); 6.25 (s, 1H); 6.20 (d, 1H); 4.62 (m, 1H); 4.60 (s, 2H); 3.74 (t, 2H); 3.71 (t, 2H); 3.58 (s, 3H); 1.46-1.67 (m, 8H).

D] Preparation of compound of formula I-A where R1 is [2-[(3-cyclopentyloxy-4-methoxy-phenyl)-(pyridin-3-ylmethyl)-amino]-ethyl]thio, R12 and R13 taken together form a C=O group and R14 is methyl (I-5)

The title compound I-5 is prepared starting from (2-chloro-ethyl)-(3-cyclopentyloxy-4-methoxy-phenyl)-pyridin-3-ylmethyl-amine (example 5 step C) and IX-4 following the procedure described in example 4 step D.

The product is first purified by preparative HPLC with system Bp. The isolated product is dissolved in DCM and washed with diluted aqueous NaOH. The organic layer is dried and evaporated. This product is further purified by HPLC (system Ap).

MS: accurate mass (ESI): 1128.6434 Da.

Ret. Time (system Aa): 16.7 min.

Example 6

Preparation of I-6, compound of formula I-A where R1 is [2-[(5-(3,5-dichloro-pyridin-4-yl-amino-carbonyl)-1-ethyl-1H-pyrazolo[3,4-b]pyridin-4-ylamino]-ethyl]thio, R12 and R13 taken together form a C=O group and R14 is methyl.

A] Preparation of 4-(2-chloro-ethylamino)-1-ethyl-1H-pyrazolo[3,4-b]pyridine-5-carboxylic acid ethyl ester 2.54 g (10 mmol) of 4-chloro-1-ethyl-1H-pyrazolo[3,4-b]pyridine-5-carboxylic acid ethyl ester (*J. Med. Chem.* 2001, 44, 1025) and 1.28 g (11 mmol) 2-chloroethylamine hydrochloride are added to 40 ml of anhydrous ethanol. Then 7 ml (50 mmol) of triethylamine are added. The mixture is heated at reflux until the reaction is completed (4 hours). The reaction mixture is concentrated under reduced pressure and 20 ml of saturated aqueous sodium carbonate solution is added. The mixture is extracted with 3×20 ml ethyl acetate. The combined organic layers are washed with 15 ml of water and 15 ml of brine, dried over Na$_2$SO$_4$ and evaporated in vacuo. The crude product (2.88 g) is first purified by flash chromatography on silica gel (petrol ether/ethyl acetate 5:1) and then crystallized from 20 ml of hexane/ethyl acetate=1/1 to afford 1.24 g (42%) of the desired product as a white crystalline solid.

MS (ESI): 297.1 ([M+H]$^+$).

$^1$H-NMR (CDCl$_3$): 9.70 (broad, 1H), 8.90 (s, 1H), 8.04 (s, 1H), 4.54 (q, 2H), 4.36 (q, 2H), 4.03 (t, 2H), 3.87 (t, 2H), 1.50 (t, 3H), 1.40 (t, 3H).

B] Preparation of 4-(2-chloro-ethylamino)-1-ethyl-1H-pyrazolo [3,4-b]pyridine-5-carboxylic acid A solution of 1.17 g (4.0 mmol) of the product of example 6 step A in 15 ml ethanol is added to a solution of 0.64 g (16.0 mmol) of NaOH in 2 ml water. The resulting mixture is heated at reflux for 3 hours. Ethanol is removed under reduced pressure and 10 ml of water is added to the residue. The solution is acidified to pH 5 with HCl 2N leading to precipitation of the product. The precipitate is isolated by filtration and dried to afford 0.5 g (44%) of the desired product as a white solid.

MS (ESI): 269.1 ([M+H]$^+$).

$^1$H-NMR (CDCl$_3$): 12.75 (b, 1H), 9.54 (s, 1H), 8.68 (s, 1H), 8.19 (s, 1H), 4.36 (q, 2H), 4.05 (t, 2H), 3.93 (t, 2H), 1.34 (t, 3H).

C] Preparation of 4-(2-chloro-ethylamino)-1-ethyl-1H-pyrazolo[3,4-b]pyridine-5-carboxylic acid (3,5-dichloro-pyridin-4-yl)-amide 0.8 g (3.0 mmol) of the product of example 6 step B, 0.8 g (6 mmol) HOBt and 1.14 g (6 mmol) EDC•HCl are suspended in 25 ml THF and 2.1 g (21 mmol) triethylamine are added. The mixture is stirred at 15° C. until all starting material disappeared (24 hours). The solvent is removed under reduced pressure and the crude product is purified by column chromatography (petrol ether/ethyl acetate 4:1) to afford 0.64 g of a white solid. 131 mg NaH (60%, 5.7 mmol) is suspended in 15 ml THF and a solution of 3,5-dichloro-4-aminopyridine in 5 ml THF is added dropwise at 15° C. to this suspension. After 1 hour a solution of 570 mg (1.42 mmol) of the above-mentioned white solid in 5 ml THF is slowly added to this mixture and stirred for another 30 minutes. 0.1 ml of water is added to the reaction mixture and the solvent is evaporated. The residue is purified by flash chromatography on silica gel (petrol ether/ethyl acetate 4:1) to give 92 mg of the desired product. This product is recrystallised from acetone/hexane 1/2 to give 68 mg (11.6%) of the desired product as pale yellow solid.

MS (ESI): 413.0 ([M+H]$^+$).

$^1$H-NMR (CDCl$_3$): 9.68 (s, 1H), 8.77 (s, 1H), 8.56 (s, 2H), 8.06 (s, 1H), 7.91 (s, 1H), 4.53 (q, 2H), 4.03 (t, 2H), 3.82 (t, 2H), 1.52 (t, 3H).

D] Preparation of compound of formula I-A where R1 is [2-[(5-(3,5-dichloro-pyridin-4-yl-amino-carbonyl)-1-ethyl-1H-pyrazolo [3,4-b]pyridin-4-ylamino]-ethyl]thio, R12 and R13 taken together form a C=O group and R14 is methyl (I-6)

The title compound I-6 is prepared starting from 4-(2-chloro-ethylamino)-1-ethyl-1H-pyrazolo[3,4-b]pyridine-5-carboxylic acid (3,5-dichloro-pyridin-4-yl)-amide (product of example 6 step C) and IX-1 following the procedures described in example 1 steps O-P. the product is purified by HPLC (System Ap)

MS: accurate mass (ESI): 1180.5134 Da.

Example 7

Preparation of I-7, compound of formula I-A where R1 is [3-[2,3-dimethoxy-6-(pyridin-4-yl-amino-carbonyl)phenyl]-propyl]thio, R12 and R13 taken together form a C=O group and R14 is methyl.

A] Preparation of 1-(3-benzyloxy-propyl)-2,3-dimethoxy-benzene 2.50 g (62.5 mmol) NaH (60% in oil) are suspended under nitrogen in 70 ml dry THF and a solution of 7.1 g (36.2 mmol) 3-(2,3-dimethoxy-phenyl)-propan-1-ol (*J. Org. Chem.*, 1987, 52, 1072) in 50 ml THF is added dropwise at 18° C. The resulting mixture is stirred for 30 minutes and then a solution of 6.81 g (39.8 mmol) benzylbromide in 30 ml THF is added dropwise and the mixture is stirred over night at 18° C. The reaction is quenched with 10 ml water and the organic solvent is evaporated under reduced pressure. The residue is dissolved in 200 ml of ethyl acetate and the organic layer is washed with water and brine, dried over Na$_2$SO$_4$ and evaporated in vacuo. The crude product is purified by column chromatography on silica gel (ethyl acetate/n-hexane 1:40) to afford 8 g (77%) of the desired product as a colorless oil.

$^1$H-NMR (CDCl$_3$): 7.36-7.27 (m, 5H); 6.99-6.95 (m, 1H); 6.78-6.76 (m, 2H); 4.52 (s, 2H); 3.86 (s, 3H,); 3.81 (s, 3H); 3.52 (t, 2H); 2.73 (t, 2H); 1.93 (m, 2H).

B] Preparation of 1-(3-benzyloxy-propyl)-6-bromo-2,3-dimethoxy-benzene 8.0 g (27.9 mmol) of the product of example 7 step A are dissolved under nitrogen in 120 ml of DCM and 5.47 g (30.7 mmol) N-bromosuccinimide and 0.48 g (2.8 mmol) are added. The mixture is stirred over night at 18° C. The reaction mixture is concentrated in vacuo and the crude product is purified by column chromatography on silica gel (ethyl acetate/n-hexane 1:40) to give 9.7 g (95%) of the desired product as a colorless oil. $^1$H-NMR (CDCl$_3$): 7.38-7.27 (m, 5H); 7.24 (d, 1H); 6.67 (d, 1H); 4.54 (s, 2H); 3.84 (s, 3H); 3.81 (s, 3H); 3.58 (t, 2H); 2.86 (t, 2H); 1.875 (m, 2H).

C] Preparation of 2-(3-benzyloxy-propyl)-3,4-dimethoxy-benzoic acid 9.7 g (26.7 mmol) of the product of example 7 step B are dissolved under nitrogen in 40 ml of dry THF. The solution is cooled to −78° C. and 18 ml of a solution of butyl-lithium (2.2M in n-hexane) are added. After 30 minutes 400 g of solid CO$_2$ are added and the reaction mixture is slowly warmed to room temperature. The reaction mixture is poured into water and the mixture is extracted with hexane. 20 ml of aqueous HCl 3M are added to the aqueous layer and extracted with 2×100 ml of ethyl acetate. The combined organic layer is washed with brine, dried over Na$_2$SO$_4$ and evaporated in vacuo to give 9 g of the crude product as white solid.

$^1$H-NMR (CDCl$_3$): 7.86 (d, 1H); 7.37-7.24 (m, 5H); 6.82 (d, 1H); 4.53 (s, 2H); 3.92 (s, 3H); 3.82 (s, 3H); 3.59 (t, 2H); 3.13 (t, 2H); 1.92 (m, 2H).

D] Preparation of 2-(3-benzyloxy-propyl)-N-(3,5-dichloro-pyridin-4-yl)-3,4-dimethoxy-benzamide 10.8 g (52.4 mmol) DCC and 5.0 g (37 mmol) HOBt are added to a solution of 8.7 g (26.3 mmol) of the product of example 7 step C in 150 ml DCM under an atmosphere of nitrogen and the mixture is stirred at 40° C. for 2 hours. The suspension is filtered and the filtrate is concentrated in vacuo. The resulting product is purified by column chromatography on silica gel (hexane/ethyl acetate 8/1) to give 8.5 g of a white solid. A solution of 4 g (8.9 mmol) of this white solid in 40 ml dry THF is added dropwise to a suspension of 1.6 g (9.8 mmol) 4-amino-3,5-dichloro-pyridine and 822 mg (35.8 mmol) NaH (60% in oil) in THF, which has been stirred at room temperature for 1.5 hours. The resulting mixture is stirred at 30° C. for 2 hours and then quenched with water. The mixture is extracted with 2×100 ml of ethyl acetate. The combined organic layers are washed with water and brine, dried over Na$_2$SO$_4$ and evaporated in vacuo. The crude product is purified by column chromatography on silica gel to give 4.1 g (96%) of the desired product as white solid.

¹H-NMR (DMSO-d₆): 8.47 (s, 2H); 8.39 (s, 1H); 7.43 (d, 1H); 7.26-7.17 (m, 5H); 6.88 (d, 1H,); 4.38 (s, 2H); 3.92 (s, 3H); 3.84 (s, 3H); 3.54 (t, 2H); 3.08 (t, 2H); 2.09 (q, 2H).

E] Preparation of 2-(3-hydroxy-propyl)-3,4-dimethoxy-N-pyridin-4-yl-benzamide 1.0 g (2.1 mmol) of the product of example 7 step D is dissolved in 200 ml of ethanol and 230 mg Pd/C (10%) are added. The mixture is stirred for 36 hours at room temperature under an atmosphere of hydrogen gas (40 psi). The catalyst is removed by filtration and the filtrate is concentrated under reduced pressure. The crude product is purified by column chromatography on silica gel to give 280 mg of the desired product as white solid.

MS (ESI): 317.1 ([MH]⁺).

¹H-NMR (DMSO-d₆): 11.58 (s, 1H); 8.71 (d, 2H); 8.18 (d, 2H); 7.37 (d, 1H); 7.04 (d, 1H); 3.86 (s, 3H); 3.74 (s, 3H); 3.36 (t, 2H); 2.75 (t, 2H); 1.61 (q, 2H).

F] Preparation of 2-(3-chloro-propyl)-3,4-dimethoxy-N-pyridin-4-yl-benzamide 200 mg (0.63 mmol) of the product of example 7 step E and 163 mg (0.76 mmol) of PCl5 are dissolved in 4 ml DCM and the resulting mixture is stirred at 20° C. for 30 minutes. The mixture is concentrated and the crude product is purified by column chromatography on silica gel (DCM/MeOH 10:1) to afford 160 mg (75%) of the desired product as a white solid.

MS (ESI): 335.1 ([MH]⁺).

¹H-NMR (DMSO-d₆): 11.54 (s, 1H); 8.69 (d, 2H); 8.15 (d, 2H); 7.391 (d, 1H); 7.09 (d, 1H); 3.87 (s, 3H); 3.76 (s, 3H); 3.61 (t, 2H); 2.84 (t, 2H); 1.934 (q, 2H).

G] Preparation of compound of formula I-A where R1 is [3-[2,3-dimethoxy-6-(pyridin-4-yl-amino-carbonyl)phenyl]-propyl]thio, R12 and R13 taken together form a C=O group and R14 is methyl (I-7)

The title compound I-7 is prepared starting from 2-(3-chloro-propyl)-3,4-dimethoxy-N-pyridin-4-yl-benzamide (example 7 step F) and IX-4 following the procedure described in example 4 step D. This product is purified by preparative HPLC (system Ap) to give a white solid.

MS: accurate mass (ESI): 1102.5927 Da.

Example 8

Preparation of I-8, compound of formula I-A where R1 is [3-[4-Amino-7-(pyridin-4-yl-amino-carbonyl)-imidazo[4,5-c]pyridin-1-yl]-propyl]thio, R12 and R13 taken together form a C=O group and R14 is methyl.

A] Preparation of 4,6-dihydroxy-nicotinic acid ethyl ester

A mixture of 5.0 g (24.73 mmol) diethyl 1,3-acetonedicarboxylate, 5.05 g (49.45 mmol) acetic anhydride and 3.7 g (24.73 mmol) ethyl orthoformate is heated to 120° C. for 2 hours. Volatile components are removed under reduced pressure and the remaining mixture is treated with 10 ml of aqueous ammonia (25%). The mixture is stirred for 30 minutes at room temperature. Subsequently the pH of the mixture is adjust to pH 2 with aqueous HCl (2N). The solid is filtered off, washed with cold water and dried. 8 ml of toluene are added to the crude product, the mixture is stirred at 0° C. for 30 minutes and then filtered and dried to give 2.26 g (50%) of a red solid.

¹H-NMR (DMSO-d₆): 11.77 (s, br, 1H); 10.74 (s, br, 1H); 8.01 (s, 1H); 5.60 (s, 1H); 4.26 (q, 2H); 1.28 (t, 3H).

B] Preparation of 4,6-dihydroxy-5-nitro-nicotinic acid ethyl ester

To a solution of 2.34 g (12.78 mmol) of the product of example 8 step A in 9 ml of acetic acid is added dropwise at 60° C. 1.24 g nitric acid (65%; 12.78 mmol). The mixture is stirred at 90° C. for 20 hours. The reaction mixture is cooled to 0° C., filtered and the filter cake is washed with cold water. The solid is dried to give 2.2 g (75%) of the desired product as light yellow crystals.

MS (ESI): 229.0 ([MH]⁺).

C] Preparation of 4,6-dichloro-5-nitro-nicotinic acid ethyl ester 2.0 g (8.77 mmol) of the product of example 8 step B in 8.0 ml (86 mmol) phosphorus oxychloride are stirred at 80° C. for 74 hours. About half of the phosphorus oxychloride is then removed in vacuo and the remaining mixture is poured onto ice. The mixture is extracted with 3×30 ml of ethyl acetate. The combined organic phases are washed with 30 ml of aqueous sodium carbonate (10%), 2×30 ml water and 30 ml of brine, dried over Na₂SO₄ and evaporated in vacuo to give the crude product as a brown oil which is purified by column chromatography on silica gel (ethyl acetate/hexane 1:20) to give 1.67 g (72%) of the desired product as light yellow solid.

¹H-NMR (DMSO-d₆): 9.08 (s, 1H); 4.40 (q, 2H); 1.35 (t, 3H).

D] Preparation of 3-(tent-butyl-dimethyl-silanyloxy)-propylamine

A solution of 7.4 g (98 mmol) 3-aminopropanol in 10 ml THF is added at room temperature to a suspension of 4.12 sodium hydride (60%; 103.2 mmol) in 140 ml THF. The mixture is stirred for 1 hour and then 16.28 g (108 mmol) tert-butyl-dimethylsilylchloride is added and vigorous stirring is continued for 1 hour. The mixture is diluted with 300 ml diethylether and washed successively with 100 ml of aqueous K₂CO₃ (10%), 100 ml of water and 100 ml of brine, dried over MgSO₄ and evaporated to give 17 g of light yellow crude product. This product is dissolved in ethyl acetate/hexane 1/10 and filtered through a pad of silica gel. The filtrate is concentrated in vacuo to give 13 g (70%) of the desired product as a colorless oil.

¹H-NMR (CDCl₃): 3.67 (t, 2H); 2.78 (t, 2H); 1.83 (s, br, 2H); 1.64 (m, 2H); 0.87 (s, 9H); 0.33 (s, 6H).

E] Preparation of 4-[3-(tert-butyl-dimethyl-silanyloxy)-propylamino]-6-chloro-5-nitro-nicotinic acid ethyl ester A solution of 6.0 g (22.6 mmol) of the product of example 8 step C and 2.3 g (22.6 mmol) triethylamine in 75 ml of ethanol is heated to reflux. 4.0 g (22.6 mmol) of the product of example 8 step D is added to this solution and the mixture is stirred at reflux for an additional hour. The solvent is removed under reduced pressure and the resulting residue is purified by column chromatography on silica gel (hexane/ethyl acetate 80:1) to afford 9 g (95%) of the desired product as yellow oil.

¹H-NMR (DMSO-d₆): 8.96 (t, 1H); 8.70 (s, 1H); 4.36 (q, 2H); 3.70 (t, 2H); 3.22 (td, 2H); 1.84 (m, 2H); 1.39 (t, 3H); 0.88 (s, 9H); 0.02 (s, 6H).

F] Preparation of 5-amino-4-[3-(tert-butyl-dimethyl-silanyloxy)-propylamino]-6-chloro-nicotinic acid ethyl ester 8.5 g (26.5 mmol) of the product of example 8 step E are dissolved in 100 ml of ethanol and 2.5 g of Raney-nickel are added. The reaction mixture is stirred for 16 hours under an atmosphere of hydrogen gas (1 atm) at room temperature. The catalyst is removed by filtration through a pad of silica gel and the filtrate is concentrated under reduced pressure. The crude product is purified by column chromatography on silica gel (hexane/ethyl acetate 20:1) to afford 5.6 g (58%) of the desired product as brown oil.

MS (ESI): 388.1; 390.1 ([MH]⁺).

G] Preparation of 1-[3-(tert-butyl-dimethyl-silanyloxy)-propyl]-4-chloro-1H-imidazo[4,5-c]pyridine-7-carboxylic acid ethyl ester 5.6 g (15.5 mmol) of the product of example 8 step F are dissolved in 45 ml triethylorthoformate and the mixture is heated to reflux during 44 hours. The mixture is concentrated under reduced pressure and another 45 ml triethylorthoformate are added and the mixture is heated to reflux for additional 24 hours. The mixture is concentrated under reduced pressure and the residue is purified by column chromatography on silica gel eluting with hexane/ethyl acetate (20/1→5/1) to afford 2.7 g (40%; purity ~62%) of the desired compound as light yellow solid. $^1$H-NMR (CDCl$_3$): 8.27 (t, 1H); 7.90 (s, 1H); 4.25 (q, 2H); 3.60 (t, 2H); 3.40 (td, 2H); 1.65 (m, 2H); 1.30 (t, 3H); 0.80 (s, 9H); 0.01 (s, 6H).

H] Preparation of 4-amino-1-[3-(tert-butyl-dimethyl-silanyloxy)-propyl]-1H-imidazo[4,5-c]pyridine-7-carboxylic acid ethyl ester Approximately 20 g of ammonia gas is dissolve in 40 ml of ethanol in a 100 ml autoclave and 2.7 g (6.28 mmol; purity ~62%) of the product of example 8 step G are added. The mixture is stirred at 100° C. for 20 hours. The reaction is cooled down and the solvent is evaporated under reduced pressure. The residue is purified by column chromatography on silica gel (DCM/MeOH 100:1 then 50:1) to afford 1.5 g (83%) of a dark brown solid.

I] Preparation of 4-amino-1-[3-hydroxy-propyl]-1H-imidazo[4,5-c]pyridine-7-carboxylic acid ethyl ester 1.5 g (3.4 mmol) of the product of example 8 step H is dissolved in 30 ml dry THF and 1.17 g (~4.5 mmol) tetrabutylammonium fluoride. H$_2$O is added. The mixture is stirred at room temperature for 1 hour. The solvent is removed under reduced pressure and the residue is purified by column chromatography on silica gel (ethyl acetate, then ethyl acetate/MeOH 50:1 then ethyl acetate/MeOH 20:1) to give 750 mg (69%) of the desired product as a white solid. $^1$H-NMR (DMSO-d$_6$): 8.31 (s, 1H); 8.08 (s, 1H); 7.00 (s, 2H); 4.59 (t, 2H); 4.26 (q, 2H); 3.22 (t, 2H); 1.72 (m, 2H); 1.29 (t, 3H).

K] Preparation of 4-amino-1-[3-chloro-propyl]-1H-imidazo[4,5-c]pyridine-7-carboxylic acid ethyl ester A suspension of 750 mg (2.36 mmol) of the product of example 8 step I in 22 ml thionyl chloride is stirred at 50° C. for 0.5 hours. 0.275 ml of triethylamine are added and stirring is continued for 11 hours at 50° C. After completion of the reaction 30 ml of diethyl ether is added to the cooled reaction mixture leading to the formation of a precipitate. The solid is isolated by filtration to give 640 mg (91%) of the desired product as a light yellow powder.

MS (ESI): 283.0 ([MH]$^+$).
$^1$H-NMR (DMSO-d$_6$): 9.00 (s, br, 2H); 8.52 (s, 1H); 8.30 (s, 1H); 4.68 (t, 2H); 4.35 (q, 2H); 3.40 (t, 2H); 2.15 (m, 2H); 1.32 (t, 3H).

L] Preparation of 4-amino-1-[3-chloro-propyl]-1H-imidazo[4,5-c]pyridine-7-carboxylic acid To a mixture of 100 mg (0.35 mmol) of the product of example 8 step K and 0.7 ml of a 2M aqueous solution of LiOH are added 2 ml of THF and 4 ml of MeOH. The mixture is stirred over night at room temperature and then additional 0.7 ml of a 2M aqueous solution of LiOH are added and the mixture is stirred at 45° C. over night. The pH of the mixture is adjusted to pH=7 with 2N aqueous HCl and the solvent is evaporated under reduced pressure. The residue is purified by preparative HPLC (Column: Purospher STAR RP18e, 5 μm, 125×25 mm flow: 25 mL/min; detection: 254 nm; mobile phase A: water+0.1% formic acid; mobile phase B: acetonitrile; gradient: linear form 20% to 60% acetonirile in 10 min) to give 30 mg (33%) of the desired product as white solid.

M] Preparation of 4-amino-1-[3-chloro-propyl]-1H-imidazo[4,5-c]pyridine-7-carboxylic acid pyridin-4-yl amide A suspension of 60 mg (0.24 mmol) of the product of example 8 step L, 108 mg (0.28 mmol) HATU, 72 mg (0.77 mmol) 4-amino-pyridine and 0.048 ml (0.28 mmol) DIPEA in 4.5 ml DMF is stirred for 3 hours at 30° C. The reaction mixture became clear. Additional 90 mg (0.24 mmol) HATU, 22 mg (0.24 mmol) 4-amino-pyridine and 0.040 ml (0.24 mmol) DIPEA are added to reaction mixture and stirring is continued for another 21 hours. The mixture is concentrated and the crude product is purified by preparative HPLC to give the desired product (containing some formiate) as a white solid.

MS (ESI): 331.1; 333.1 ([MH]$^+$).
$^1$H-NMR (DMSO-d$_6$): 10.76 (s, 1H); 8.44 (d, 2H); 8.15 (s, 1H); 8.13 (s, 1H); 7.21 (d, 2H); 6.93 (s, 2H); 4.51 (t, 2H); 3.42 (t, 2H); 2.03 (m, 2H).

N] Preparation of compound of formula I-A where R1 is [3-[4-Amino-7-(pyridin-4-yl-amino-carbonyl)-imidazo[4,5-c]pyridin-1-yl]-propyl]thio, R12 and R13 taken together form a C=O group and R14 is methyl. (I-8)

The title compound I-8 is prepared starting from 4-amino-1-[3-chloro-propyl]-1H-imidazo[4,5-c]pyridine-7-carboxylic acid pyridin-4-yl amide (product of example 8 step M) and IX-1 following the procedures described in example 1 steps O-P. The product 1-8 is purified by HPLC (System Ap)

$^1$H-NMR (CDCl$_3$): (diagnostic signals only) 8.97 (s, br, 1H); 8.56 (d, 2H); 8.27 (s, 1H); 8.15 (s, 1H); 7.72 (d, br, 2H); 5.82 (s, br, 2H); 5.40 (dd, 1H); 4.91 (d, 1H); 4.60-4.77 (m, 2H); 4.51 (d, 1H); 4.18 (s, 1H); 3.98-4.05 (m, 1H); 3.79 (d, 1H); 3.69 (d, 1H); 3.5-3.6 (m, 1H); 3.35 (s, 3H); 3.08 (s, 3H); 1.42 (s, 3H); 1.37 (s, 3H); 1.15 (d, 3H); 1.08 (d, 3H); 1.01 (d, 3H); 0.85 (t, 3H).

Example 9

Preparation of I-9, compound of formula I-A where R1 is [3-[4-amino-7-[([methoxycarbonylmethyl]-amino-carbonyl)-imidazo[4,5-c]pyridin-1-yl]-propyl]thio, R12 and R13 taken together form a C=O group and R14 is methyl.

A] Preparation of {[4-amino-1-(3-chloro-propyl)-1H-imidazo[4,5-c]pyridine-7-carbonyl]-amino}-acetic acid methyl ester A mixture of 60 mg (0.24 mmol) of the product of example 8 step L, 54 mg (0.28 mmol) EDC, 38 mg (0.28 mmol) HOBt and 89 mg (0.71 mmol) glycine methyl ester HCl salt in 6 ml DMF is stirred for 2 hours at room temperature. The mixture is concentrated and the crude product is purified by preparative HPLC to give 72 mg of the desired product as a white solid.

$^1$H-NMR (DMSO-d$_6$): 9.32 (m, 1H); 8.66 (s, br, 2H); 8.47 (s, 1H); 7.89 (s, 1H); 4.52 (t, 2H); 4.04 (d, 2H); 3.67 (s, 3H); 3.52 (t, 2H); 2.11 (m, 2H).

B] Preparation of compound of formula I-A where R1 is [3-[4-amino-7-[([methoxycarbonylmethyl]-amino-carbonyl)-imidazo[4,5-c]pyridin-1-yl]-propyl]thio, R12 and R13 taken together form a C=O group and R14 is methyl (I-9)

The title compound I-9 is prepared starting from {[4-amino-1-(3-chloro-propyl)-1H-imidazo[4,5-c]pyridine-7-carbonyl]-amino}-acetic acid methyl ester (product of example 9 step A) and IX-1 following the procedures described in example 1 steps O-P. The product I-8 is purified by HPLC (System Ap) to give the desired product as a white solid.

MS: accurate mass (ESI): 1093.5698 Da.

Example 10

Preparation of I-10, compound of formula I-A where R1 is [2-[4-amino-7-(pyridin-4-yl-amino-carbonyl)-imidazo[4,5-c]pyridin-1-yl]-ethyl]thio, R12 and R13 taken together form a C=O group and R14 is methyl.

A] Preparation of 4-[2-(tert-butyl-dimethyl-silanyloxy)-ethylamino]-6-chloro-5-nitro-nicotinic acid ethyl ester A solution of 362 mg (1.37 mmol) of the product of example 8 step C and 138 mg (1.37 mmol) triethylamine in 4 ml of ethanol is heated to reflux. 240 mg (1.37 mmol) of 2-(tert-butyl-dimethyl-silanyloxy)-ethylamine is added dropwise to this solution and the mixture is stirred at reflux for an additional hour. The solvent is removed under reduced pressure and the resulting residue is purified by column chromatography on silica gel (hexane/ethyl acetate 80:1) to afford 430 mg (79%) of the desired product as yellow oil.

$^1$H-NMR (DMSO-$d_6$): 9.05 (m, 1H); 8.66 (s, 1H); 4.33 (q, 2H); 3.75 (t, 2H); 3.11 (t, 2H); 1.32 (t, 3H); 0.84 (s, 9H); 0.04 (s, 6H).

B] Preparation of 4-amino-1-[2-chloro-ethyl]-1H-imidazo[4,5-c]pyridine-7-carboxylic acid ethyl ester 4-amino-1-[2-chloro-ethyl]-1H-imidazo[4,5-c]pyridine-7-carboxylic acid ethyl ester is prepared starting from the product of example 10 step A following the procedures described in example 8 steps F to K. The desired product is isolated as light yellow powder.

$^1$H-NMR (DMSO-$d_6$): 9.00 (s, br, 2H); 8.53 (s, 1H); 8.31 (s, 1H); 4.96 (t, 2H); 4.33 (q, 2H); 4.00 (t, 2H); 1.32 (t, 3H).

C] Preparation of 4-amino-1-[2-chloro-ethyl]-1H-imidazo[4,5-c]pyridine-7-carboxylic acid To a mixture of 50 mg (0.19 mmol) of 4-amino-1-[2-chloro-ethyl]-1H-imidazo[4,5-c]pyridine-7-carboxylic acid ethyl ester (example 10 step B) and 1.1 ml of a 2M aqueous solution of NaOH are added 0.3 ml of THF and 0.8 ml of MeOH. The mixture is stirred for 2.5 hours at room temperature. MeOH and THF are evaporated under reduced pressure and the pH of the remaining mixture is adjusted to pH=2 with 2N aqueous HCl. The product precipitated and is isolated by filtration. Toluene is added to the product and the solvent is evaporated. This process is repeated three times. Finally 24 mg (53%) of the desired product are isolated as a light grey solid.

MS (ESI): 241.0 ([MH]$^+$).

$^1$H-NMR (DMSO-$d_6$): 8.35 (s, 1H); 8.14 (s, 1H); 7.06 (s, br, 2H); 4.93 (m, 2H); 3.89 (m, 1H).

D] Preparation of 4-amino-1-[2-chloro-ethyl]-1H-imidazo[4,5-c]pyridine-7-carboxylic acid pyridin-4-yl amide A mixture of 48 mg (0.20 mmol) of the product of example 10 step C, 114 mg (0.30 mmol) HATU, 61 mg (0.65 mmol) 4-amino-pyridine and 0.051 ml (0.30 mmol) DIPEA in 15 ml DMF is stirred overnight at 30° C. The product is directly purified by preparative HPLC to give 47 mg (74%) of the desired product as a white solid.

$^1$H-NMR (DMSO-$d_6$): 10.79 (s, 1H); 8.43 (d, 2H); 8.29 (s, 1H); 8.17 (s, 1H); 7.69 (d, 2H); 6.94 (s, 2H); 4.77 (t, 2H); 3.86 (t, 2H).

E] Preparation of compound of formula I-A where R1 is [2-[4-amino-7-(pyridin-4-yl-amino-carbonyl)-imidazo[4,5-c]pyridin-1-yl]-ethyl]thio, R12 and R13 taken together form a C=O group and R14 is methyl (I-10)

The title compound I-10 is prepared starting from 4-amino-1-[2-chloro-ethyl]-1H-imidazo[4,5-c]pyridine-7-carboxylic acid pyridin-4-yl amide (example 10 step D) and IX-4 following the procedure described in example 4 step D. This product is purified by preparative HPLC (system Cp) to give a white solid.

MS: accurate mass (ESI): 1084.5637 Da.

Example 11

Preparation of I-11, compound of formula I where R1 is [2-[4-amino-7-(3,5-dichloro-pyridin-4-yl-amino-carbonyl)-imidazo[4,5-c]pyridin-1-yl]-ethyl]thio, R12 and R13 taken together form a C=O group and R14 is methyl.

A] Preparation of compound of formula I-A where R1 is [2-[4-amino-7-ethoxycarbonyl-imidazo[4,5-c]pyridin-1-yl]-ethyl]thio, R12 and R13 taken together form a C=O group and R14 is methyl To a solution of 1.6 g (1.9 mmol) of the product of example 4 step C (IX-4) and 0.5 ml water in 40 ml DMF are added 765 mg (3.8 mmol) tributylphosphine and the mixture is stirred at room temperature for 3 hours. 400 mg (1.39 mmol) of the product of example 10 step B and 290 mg (1.9 mmol) of DBU are added and the mixture is stirred for 20 hours at 20° C. Then 60 ml of water are added to the reaction and the mixture is extracted with 3×80 ml of ethyl acetate. The combined organic layers are washed with water, dried over Na$_2$SO$_4$ and the solvent is evaporated in vacuo. The crude product is purified by column chromatography on silica gel (DCM/MeOH 40/1, 20/1, 10/1) to give 895 mg (46%) of the desired product as light yellow powder.

MS (ESI): 518.8 ([M+2H]$^{++}$/2)

B] Preparation of compound of formula I-A where R1 is [2-[4-amino-7-carboxyl-imidazo[4,5-c]pyridin-1-yl]-ethyl]thio, R12 and R13 taken together form a C=O group and R14 is methyl A mixture of 300 mg (0.3 mmol) of the product of example 11 step A, 3 ml of aqueous LiOH (2N), 8 ml of THF and 6 ml of MeOH is stirred at 18° C. for 20 hours. The reaction mixture is concentrated under reduced pressure and the residue is extracted with 3×50 ml DCM. The combined organic layers are washed with brine, dried over Na$_2$SO$_4$ and the solvent is evaporated in vacuo to give 0.172 g of the crude product. The crude product is purified by preparative HPLC (Column: Purospher Star RP-18e, 5 μm, 125×25 mm flow: 25 mL/min; detection: 254 nm; mobile phase A: water+0.1% formic acid; mobile phase B: acetonitrile; gradient: linear from 10% to 40% acetonitrile in 8 min; then 100% acetonitrile) to give a white solid.

MS (ESI): 504.8 ([M+2H]$^{++}$/2)

Ret. Time (system Ba): 12.9 min.

C] Preparation of compound of formula I-A where R1 is [2-[4-amino-7-(3,5-dichloro-pyridin-4-yl-amino-carbonyl)-imidazo[4,5-c]pyridin-1-yl]-ethyl]thio, R12 and R13 taken together form a C=O group and R14 is methyl (I-11)

153 mg (4.46 mmol) of NaH (60% in oil) are suspended in 1 ml of DMF and a solution of 873 mg (5.3 mmol) 4-amino-3,5-dichloropyridine in 2 ml DMF are added. The suspension is stirred at 25° C. for 3 hours. In parallel, a solution of 260 mg (0.26 mmol) of the product of example 11, step B, 153 mg (0.8 mmol) EDC and 78 mg (0.58 mmol) HOBt in 5 ml DMF is stirred for 1 hour at 25° C. This solution is then added at −5 to 0° C. to the solution of 4-amino-3,5-dichloropyridine prepared above. The mixture is stirred at this temperature for 10 minutes and the reaction is quenched with 1 ml of water and the pH of the mixture is adjusted to pH 7-8 with aqueous HCl 2N. The mixture is concentrated and the residue is purified by preparative HPLC (Column: Purospher Star RP-18e, 5 μm, 125×25 mm flow: 25 mL/min; detection: 254 nm; mobile phase A: water+0.01% formic acid; mobile phase B: acetonitrile; gradient: linear from 20% to 60% acetonitrile in 10 min; 5 min with 60% acetonitrile) to give 210 mg (70%) of the desired product as a white solid.

$^1$H-NMR (DMSO-$d_6$): 10.68 (s, 1H); 8.70 (t, 2H); 8.31 (s, 1H); 8.24 (s, 1H); 6.97 (t, 2H); 5.15 (m, 1H); 4.85 (m, 1H); 4.72 (m, 1H); 4.62 (m, 1H); 4.40 (m, 3H); 4.00 (m, 1H); 3.66 (m, 1H); 3.58 (t, 2H); 2.40 (s, 6H); 1.80 (m, 2H); 1.65 (m, 2H); 1.51 (m, 3H); 1.40 (s, 3H); 1.29 (s, 3H); 1.05-1.20 (m, 16H); 1.00 (d, 3H); 0.93 (d, 3H); 0.73 (t, 3H).

MS: accurate mass (ESI): 1152.4906 Da.

Example 12

Preparation of I-12, compound of formula I-A where R1 is [2-[6-amino-2-[[(3-pyridyl)methyl]amino]-purin-9-yl]ethyl]thio, R12 and R13 taken together form a C=O group and R14 is methyl.

A] Preparation of 9-(2-chloroethyl)-2,6-diamino-purine 10 g (66.6 mmol) 2,6-diaminopurine are suspended under argon in 300 ml DMF and 21.6 g (156.5 mmol) potassium carbonate and 24 ml 1-bromo-2-chloroethane are added. The mixture is stirred for 64 hours at room temperature. The light yellow suspension is filtered and the solids are washed with 30 ml DMF and subsequently triturated with 100 ml water for 30 minutes. The mixture is filtered and the solids are washed with 50 ml water and dried in vacuo to give 10.15 g (72%) of the desired product as a white solid.

$^1$H-NMR (DMSO-$d_6$): 7.72 (s, 1H); 6.67 (s, br, 2H); 5.81 (s, br, 2H); 4.30 (t, 2H); 3.99 (t, 2H).

B] Preparation of 6-amino-9-(2-chloroethyl)-2-[(3-pyridylmethyl)amino]-purine 100 mg (0.47 mmol) of 9-(2-chloroethyl)-2,6-diamino-purine (example 12, step A) are dissolved in 10 ml MeOH and 3 g molecular sieves (4 Å), 0.044 ml (0.47 mmol) 3-pyridinecarboxaldehyde and 0.135 ml (2.35 mmol) acetic acid are added. The mixture is stirred for 2 hours at room temperature. 23.6 mg (0.38 mmol) sodium cyano-borohydride are added and stirring is continued for 4 hours. Additional 0.044 ml (0.47 mmol) 3-pyridinecarboxaldehyde are added and 72 mg sodium cyano-borohydride are added in three portions over three days at room temperature. The solvent is evaporated and the residue is taken up in 50 ml ethyl acetate. The organic layer is washed with sat. aqueous sodium carbonate and brine, dried over Na$_2$SO$_4$ and the solvent is evaporated in vacuo to give 0.254 g of the crude product as yellow oil. The crude product is purified by flash chromatography on silica gel (DCM/MeOH 99.5/0.5→80:20) to give 88 mg of the desired product as white solid.

$^1$H-NMR (DMSO-$d_6$): 8.57 (s, 1H); 8.40 (m, 1H); 7.74 (s, br, 1H); 7.73 (s, 1H); 7.30 (m, 1H); 6.99 (m, 1H); 6.75 (s, br, 2H); 4.45 (d, 2H); 4.30 (t, 2H); 3.95 (t, 2H).

C] Preparation of, compound of formula I-A where R1 is [2-[6-amino-2-[[(3-pyridyl)methyl]amino]-purin-9-yl]ethyl]thio, R12 and R13 taken together form a C=O group and R14 is methyl (I-12)

The title compound I-12 is prepared starting from 6-amino-9-(2-chloroethyl)-2-[(3-pyridylmethyl)amino]-purine (product of example 12 step B) and IX-1 following the procedures described in example 1 steps O-P. The crude product is purified by HPLC (System Ap) to give the desired product as a white solid.

MS: accurate mass (ESI): 1071.5826 Da.

Example 13

Preparation of I-13, compound of formula I-A where R1 is [2-[6-amino-2-[[(4-pyridyl)methyl]amino]-purin-9-yl]ethyl]thio, R12 and R13 taken together form a C=O group and R4 is methyl.

A] Preparation of 6-amino-9-(2-chloroethyl)-2-[(4-pyridylmethyl)amino]-purine 6-amino-9-(2-chloroethyl)-2-[(4-pyridylmethyl)amino]-purine is prepared from 4-pyridinecarboxaldehyde and 9-(2-chloroethyl)-2,6-diamino-purine according to the procedure described in example 12 step B. The crude product is purified by flash chromatography (DCM/MeOH 99.5/0.5→80:20) to give the desired product as white solid.

$^1$H-NMR (DMSO-$d_6$): 8.44 (d, 2H); 7.73 (s, 1H); 7.31 (d, 2H); 7.01 (t, 1H); 6.75 (s, br, 2H); 4.46 (d, 2H); 4.27 (t, 2H); 3.91 (t, 2H).

B] Preparation of, compound of formula I-A where R1 is [2-[6-amino-2-[[(4-pyridyl)methyl]amino]-purin-9-yl]ethyl]thio, R12 and R13 taken together form a C=O group and R14 is methyl (I-13)

The title compound I-12 is prepared starting from 6-amino-9-(2-chloroethyl)-2-[(4-pyridylmethyl)amino]-purine (product of example 13 step A) and IX-1 following the procedures described in example 1 steps O-P. The crude product is purified by HPLC (System Ap) to give the desired product as a white solid.

MS: accurate mass (ESI): 1071.5826 Da.

Example 14

Preparation of I-14, compound of formula I where R1 is [2-[4-amino-7-(3,5-dichloro-pyridin-4-yl-amino-carbonyl)-imidazo[4,5-c]pyridin-1-yl]-ethyl]thio, R2 is hydroxyl, R3 and R4 are hydrogen, R12 and R13 taken together form a C=O group and R14 is methyl.

60 mg of compound I-11 is dissolved in 5 ml aqueous HCl (1N) under nitrogen atmosphere and the solution is stirred at 28° C. for 5 hours. The reaction mixture is cooled to 0° C. and treated with aqueous Na$_2$CO$_3$ (10%) to adjust the solution to pH 7-8. The mixture is extracted with three times 30 ml DCM. The combined organic layers are washed with brine, dried over Na$_2$SO$_4$ and the solvent is evaporated in vacuo to give the crude product. The crude product is purified by chromatography on silica gel (DCM/MeOH 10:1) to give 20 mg (38%) of the desired product as an off-white solid.

$^1$H-NMR (DMSO-$d_6$) (diagnostic signals only): 10.64 (s, 1H); 8.70 (t, 2H); 8.31 (s, 1H); 8.15 (s, 1H); 6.93 (s, 2H); 5.18-5.28 (m, 2H); 4.83 (m, 1H); 4.63 (m, 1H); 4.52 (d, 1H); 4.44 (s, 1H); 3.66 (s, 1H); 1.79-1.91 (m, 2H); 1.61-1.72 (m, 2H); 1.40 (s, 3H); 1.18 (s, 3H); 0.95 (d, 3H); 0.93 (d, 3H); 0.71 (t, 3H).

Example 15

Preparation of I-15, compound of formula I where R1 is [2-[(3-cyclopentyloxy-4-methoxy-phenyl)-(3,5-dichloropyridin-4-yl-methyl)-amino]ethyl]thio, R2 and R3 taken together form a C=O group, R4 is hydrogen, R12 and R13 taken together form a C=O group and R14 is methyl.

A] Preparation of (3-cyclopentyloxy-4-methoxy-phenyl)-(3,5-dichloropyridin-4-yl-methyl)-amine 1.408 g (6.48 mmol) of 3-cyclopentyloxy-4-methoxy-phenylamine (Garcia et al., JOC, 2005, 70, p 1050) is dissolved in 20 ml toluene and 1.197 g (6.6 mmol) 3,5-dichloro-4-pyridinecarboxaldehyde, 3.6 ml (25.9 mmol) triethylamine and 1.85 ml (32.4 mmol) acetic acid are added. The mixture is stirred at 25° C. for 2 hours and then 1.629 g (25.9 mmol) NaBH$_3$CN are added and the mixture is stirred for at 25° C. for one hour. The solvent is evaporated and the crude product is purified by flash chromatography on silica gel (petroleum ether/ethyl acetate 15:1) to give 1.98 g (82%) of the desired product as a light yellow solid.

$^1$H NMR (DMSO-d6): 8.61 (s, 2H); 6.70 (d, 1H); 6.30 (d, 1H); 6.15 (dd, 1H); 5.55 (t, 1H); 4.65 (m, 1H); 4.36 (d, 2H); 3.59 (s, 3H); 1.77-1.81 (m, 2H); 1.64-1.67 (m, 4H); 1.53-1.56 (m, 2H).

B] Preparation of (2-chloroethyl)-(3-cyclopentyloxy-4-methoxy-phenyl)-(3,5-dichloropyridin-4-yl-methyl)-amine 1.9 g (4.96 mmol) of the compound of step A are dissolved in 20 ml methanol and 5.8 g of a solution of chloroacetaldehyde (40% in water; 29.7 mmol, 6 eq), 1.87 g (77.4 mmol, 6. eq) of NaBH$_3$CN and 0.44 ml (7.69 mmol) of acetic acid are added. The mixture is stirred at 28° C. for 5 hours. Then the solvent is removed under reduced pressure and the residue is dissolved in 20 ml water and 40 ml dichloromethane. The mixture separated and the aqueous phase is extracted with 30 ml DCM. The combined organic layers are washed with 30 ml water and with 30 ml brine, dried over Na$_2$SO$_4$ and evaporated in vacuo. The crude product is purified by flash chromatography on silica gel (petroleum ether/ethyl acetate 15:1 and 10:1) to afford 1.6 g (72%) of the desired product as a light yellow solid.

$^1$H NMR (DMSO-d6): 8.59 (s, 2H); 6.77 (d, 1H); 6.40 (s, 1H); 6.38 (d, 1H); 4.66 (m, 1H); 4.65 (s, 2H); 3.62 (s, 3H); 3.60 (t, 2H); 3.55 (t, 2H); 1.51-1.65 (m, 8H).

C] Preparation of a compound of formula XX where R1 is [2-[(3-cyclopentyloxy-4-methoxy-phenyl)-(3,5-dichloropyridin-4-yl-methyl)-amino]ethyl]thio, R2 and R3 taken together form a C=O group, R12 and R13 taken together form a C=O group and R14 is methyl and Rp$_1$ is acetyl.

89 mg (0.12 mmol) of a compound of formula XVIII where R2 and R3 taken together form a C=O bond, R4 is hydrogen R14 is methyl Rp1 is acetyl and Rp4 is methyl (synthesized according to methods described in WO03/072588) is dissolved under nitrogen atmosphere in 5 ml DMF and 1 drop of water and 0.06 ml (0.24 mmol) of tributylphosphine are added and the mixture is stirred at room temperature until no starting material remained (2 h). Then 57.5 mg (0.13 mmol) of (2-chloroethyl)-(3-cyclopentyloxy-4-methoxy-phenyl)-(3,5-dichloropyridin-4-yl-methyl)-amine and 0.018 ml DBU are added to the solution. The reaction is stirred for 20 hours at room temperature and concentrated in vacuo and the residue is taken up in 5 ml DCM. The organic layer is washed twice with 2 ml aqueous NaHCO$_3$ (5%) and with 2 ml brine, dried over Na$_2$SO$_4$, filtered and concentrated in vacuo to give the crude product as a yellow oil. The crude product is purified by flash chromatography on silica gel (DCM/MeOH/NH3 99.5:0.5:0.01→97:3:0.01) to give 44 mg of the desired product as a yellow oil.

MS (ESI): 1079.6 ([MH]$^+$). 550.9 ([M+2H]$^{++}$/2)

D] Preparation of a compound of formula I where R1 is [2-[(3-cyclopentyloxy-4-methoxy-phenyl)-(3,5-dichloropyridin-4-yl-methyl)-amino]ethyl]thio, R2 and R3 taken together form a C=O group, R12 and R13 taken together form a C=O group and R14 is methyl The product of Example 15 step C (42 mg) is dissolved in 2 ml methanol and stirred overnight at room temperature. Then reaction mixture is concentrated in vacuo and the residue is purified by flash chromatography on silica gel (DCM/MeOH/NH3 99.5:0.5→95:5) to give 0.013 mg of the desired product as an off-white solid.

MS (ESI): 1036.6 ([MH]$^+$). 518.9 ([M+2H]$^{++}$/2)

Example 16

Preparation of I-16, compound of formula I where R1 is [2-[(5-(3,5-dichloro-pyridin-4-yl-amino-carbonyl)-1-ethyl-1H-pyrazolo[3,4-b]pyridin-4-ylamino]-ethyl]thio, R2 is —OH, R3 and R4 are hydrogen, R12 and R13 taken together form a C=O group and R14 is methyl.

27 mg of compound I-6 (example 6) are suspended in 1 ml ethanol and 2 ml water and 0.15 ml of 3N HCl is added dropwise to the mixture. The mixture is stirred at room temperature for 20 hours. The mixture is neutralized with 2N NaOH and the mixture is extracted twice with 5 ml ethyl acetate. The combined organic layers are washed with aqueous NaHCO$_3$ (5%) and with brine, dried over Na$_2$SO$_4$, filtered and concentrated in vacuo to give the crude product as a off-white solid. The crude product is purified by flash chromatography on silica gel (DCM/MeOH/NH$_3$ 99:1:0.01→85:15:0.01) to give 20 mg of the desired product as a white solid.

MS (ESI): 1022.7, 1024.6 ([MH]$^+$), 512.9 ([M+2H]$^{++}$)

Example 17

Preparation of I-17, compound of formula I where R1 is [2-[5-[(3,5-dichloro-pyridin-4-ylmethyl)-amino]-2-methoxy-phenoxy]ethyl]thio, R2 and R3 taken together form a C=O group, R4 is hydrogen, R12 and R13 taken together form a C=O group and R14 is methyl.

A] Preparation of 2-(2-chloro-ethoxy)-1-methoxy-4-nitrobenzene

A mixture of 40 g (0.236 mol) 2-methoxy-5-nitrophenol, 135 g (0.946 mol) 1-bromo-2-chloroethane and 130.7 g (0.946 mol) potassium carbonate in 500 ml acetone is heated to reflux until no starting material remained (8 h). The mixture is filtered and the filtrate is evaporated. The residue is taken up in ethyl acetate and filtered through dicalite. The filtrate is evaporated under reduced pressure and the residue is crystallized from ethyl acetate to give 39.6 g of the desired product as a yellow solid.

$^1$H NMR (DMSO-d6): 7.95 (m, 1H); 7.79 (d, 1H); 7.21 (d, 1H); 4.39 (t, 3H); 3.98 (t, 3H); 3.93 (s, 3H).

B] Preparation of 3-(2-chloro-ethoxy)-4-methoxy-phenylamine 25.9 g (0.112 mol) of 2-(2-chloro-ethoxy)-1-methoxy-4-nitrobenzene (example 17, step A) are dissolved 250 ml tetrahydrofurane and the solution is degassed. Then 2.16 g of palladium on charcoal (10%) is added and the mixture is stirred under hydrogen gas (1 atm) until no starting material remained. The mixture is filtered through dicalite and the filtrate is evaporated. The compound is used without further purification for the next step.

C] Preparation of [3-(2-chloro-ethoxy)-4-methoxy-phenyl]-(3,5-dichloro-pyridin-4-ylmethyl)-amine 20 g (99 mmol) of 3-(2-chloro-ethoxy)-4-methoxy-phenylamine (example 17, step B) are dissolved in 200 ml of methanol and 17.8 g (101 mol) 3,5-dichloro-4-pyridinecarboxaldehyde and 26.5 ml (436 mmol) acetic acid are added. A precipitate formed. The mixture was stirred at room temperature for 30 minutes and then 23.3 g (370 mmol) sodium cyanoborohydride are added. The precipitate disappears and the mixture was stirred at room temperature until no starting material remained (~30 min). The solvent is evaporated under reduced pressure and the residue is taken up in ethyl acetate. The organic layer is washed with brine dried over Na$_2$SO$_4$, filtered and concentrated in vacuo to give the crude product as a solid. The crude product is crystallized from ethyl acetate/n-hexane to give 17.4 g of an off-white solid.

$^1$H NMR (DMSO-d6): 8.63 (s, 2H); 6.76 (d, 1H), 6.39 (d, 1H); 6.23 (dd, 1H); 5.60 (t, 1H); 4.37 (d, 2H); 4.15 (t, 2H); 3.90 (t, 2H); 3.65 (s, 3H).

D] Preparation of compound of formula I where R1 is [2-[5-[(3,5-dichloro-pyridin-4-ylmethyl)-amino]-2-methoxy-phenoxy]ethyl]thio, R2 and R3 taken together form a C=O group, R4 is hydrogen, R12 and R13 taken together form a C=O group and R14 is methyl (I-17).

The title compound is prepared from [3-(2-chloro-ethoxy)-4-methoxy-phenyl]-(3,5-dichloro-pyridin-4-ylmethyl)-amine (example 17, step C) and compound of formula XVIII where R2 and R3 taken together form a C=O bond, R4 is hydrogen R14 is methyl Rp1 is acetyl and Rp4 is methyl (synthesized according to methods described in WO03/072588) following the procedures described in example 15, steps C and D.

MS (ESI): 968.5 ([MH]$^+$), 485.0 ([M+2H]$^{++}$)

Example 18

Preparation of I-18, compound of formula I where R1 is [2-[5-(3,5-dichloropyridine-4-yl-aminocarbonyl)-2-methoxy-phenoxy]ethyl]thio, R2 is 2-(4-morpholinyl)acetoxy, R3 and R4 are hydrogen, R12 and R13 taken together form a C=O group and R14 is methyl.

A] Preparation of 3-(2-chloro-ethoxy)-4-methoxy-benzoic acid 500 mg (2.97 mmol) of isovanillic acid are dissolved in 5 ml DMF and 1.07 g (7.74 mmol) potassium carbonate and 0.7 ml (8.49 mmol) 1-bromo-2-chloroethane are added. The mixture is heated to 50° C. for 6 hours and to 70° C. for one hour. Subsequently DMF is evaporated and 20 ml of water is added to the residue. The aqueous layer is extracted twice with 50 ml of ethyl acetate. The organic layers are combined and the solvent is evaporated under reduced pressure. The residue is dissolved in 20 ml THF and 20 ml methanol and 20 ml of 4N aqueous NaOH is added. The reaction mixture is stirred for 2 hours at room temperature and the organic solvents are evaporated. The aqueous phase is adjusted to pH=7 with concentrated aqueous HCl leading to precipitation of the product which is isolated by filtration and washed with water to give 347 mg of the desired product as grey solid.

B] Preparation of 3-(2-chloro-ethoxy)-N-(3,5-dichloro-pyridin-4-yl)-4-methoxy-benzamide 31 mg (0.74 mmol) sodium hydride are dissolved in 2 ml DMF and 134 mg (0.82 mmol) of 4-amino-3,5-dichloropyridine is added. The mixture is stirred for 3 hours at 28° C. to give "solution A".

50 mg (0.22 mmol) of compound 14-A, 99 mg (0.26 mmol) of HATU and 45 µl (0.26 mmol) of ethyldiisopropylamine are dissolved in 20 ml DMF and the resulting solution is stirred at 29° C. for 45 minutes. Solution A (see above) is added dropwise at 0-10° C. and the mixture is stirred at this temperature for 15 minutes. The pH of the mixture is adjusted to 6 by addition of aqueous HCl and DMF is evaporated under reduced pressure. The residue is dissolved in 70 ml ethyl acetate and the organic layer is washed twice with 50 ml 0.5 N aqueous HCl, with 50 ml water and twice with 50 ml brine, dried over Na$_2$SO$_4$ and concentrated in vacuo to give 120 mg of the crude product as brown solid. The crude product is purified by flash chromatography on silica gel (ethyl acetate/petroleum ether 1:2) to give 60 mg of the desired product as white solid.

$^1$H NMR (DMSO-d6): 3.86 (s, 3H), 3.96 (t, 2H), 4.30 (t, 2H), 7.14 (d, 1H), 7.58 (d, 1H), 7.70 (dd, 1H), 8.73 (s, 2H), 10.45 (s, 1H)

C] Preparation of compound of formula XIX where R1 is [(4-methoxyphenyl)methyl]thio and Rp$_1$ is acetyl and R14 is methyl 300 mg of compound VII-1 (example 1, product of step K) are suspended in 30 ml of 1 N HCl and the mixture is stirred at 40° C. for 13 hours. 2 ml of acetonitrile is added and stirring is continued for additional 17 hours. The reaction mixture is adjusted to pH=7 with aqueous 2N NaOH and the mixture is extracted twice with 30 ml of DCM. The combined organic layers are washed with water and with brine, dried over Na$_2$SO$_4$ and concentrated in vacuo to give the crude product as light-brown foam. The crude product is purified by flash chromatography on silica gel (DCM/MeOH 40:1) to give 130 mg of the desired product as a off-white solid.

MS (ESI): 808.3 ([MH]$^+$)

D] Preparation of compound of formula XXIV where R1 is [(4-methoxyphenyl)methyl]thio and Rb is CH$_2$Cl, Rp$_1$ is acetyl and R14 is methyl 60 mg (0.07 mmol) of compound of example 18 step C is dissolved in 5 ml DCM and 28 mg (0.16 mmol) 2-chloroacetic acid anhydride, 18 mg (0.15 mmol) DMAP and 15 mg pyridine are added. The mixture is stirred at 15° C. for 1 hour and subsequently poured into 50 ml of water. The aqueous phase is extracted twice with 20 ml DCM. The combined organic layers are washed with aqueous HCl 5%, water, saturated aqueous NaHCO$_3$ and with brine, dried over Na$_2$SO$_4$ and concentrated in vacuo to give the crude product as an off-white solid. The product is used without further purification for the next step.

MS (ESI): 884.4 ([MH]$^+$)

E] Preparation of compound of formula XXV where R1 is [(4-methoxyphenyl)methyl]thio and R2b and R2c taken together form a morpholine ring (including the nitrogen to which they are attached), Rp$_1$ is acetyl and R14 is methyl 600 mg (0.68 mmol) of compound of example 18 step C is dissolved in 30 ml acetone and 280 mg (3 eq.) potassium carbonate, 150 mg morpholine (1.7 mmol) and 20 mg NaI are added. The reaction mixture is stirred at 20° C. for 20 hours and at 50° C. for 12 hours. The solvent is evaporated and the water is added to the residue. The aqueous layer is extracted three times with 30 ml DCM. The combined organic layers are washed with water and with brine, dried over Na$_2$SO$_4$ and concentrated in vacuo to give the crude product. The crude product is purified by flash chromatography on silica gel (DCM/MeOH 80:1) to give 220 mg of the desired product as a white solid.

MS (ESI): 935.3 ([MH]$^+$), 468.2 ([M+2H]$^{++}$)

F] Preparation of compound of formula I where R1 is [2-[5-(3,5-dichloropyridine-4-yl-aminocarbonyl)-2-methoxy-phenoxy]ethyl]thio, R2 is 2-(4-morpholinyl)acetoxy, R3 and R4 are hydrogen, R12 and R13 taken together form a C=O group and R14 is methyl (I-18).

The title compound is prepared from 3-(2-chloro-ethoxy)-N-(3,5-dichloro-pyridin-4-yl)-4-methoxy-benzamide (example 18, step B) and compound of example 18, step E following the procedures described in example 15, steps C and D.

MS (ESI): 1111.3 ([MH]$^+$), 556.4 ([M+2H]$^{++}$)

Ret. Time (System Ca): 28.0 min

Example 19

Preparation of I-19, compound of formula I where R1 is [2-[5-(3,5-dichloropyridine-4-yl-aminocarbonyl)-2-methoxy-phenoxy]ethyl]thio, R2 is 3-(4-morpholinyl)-1-oxopropoxy, R3 and R4 are hydrogen, R12 and R13 taken together form a C=O group and R14 is methyl.

A] Preparation of compound of formula XXIV where R1 is [(4-methoxyphenyl)methyl]thio and Rb is —CH=CH$_2$, Rp$_1$ is acetyl and R14 is methyl 30 mg (0.04 mmol) of compound of example 18 step C is dissolved in 10 ml of DCM and 6.7 mg (2. eq.) acryloyl chloride and 11.3 mg triethylamine are added. The reaction mixture was stirred at room temperature over night and then additional 3.35 mg of acryloyl chloride are added. The reaction mixture is stirred at room temperature until no starting material remained (1.5 h). The mixture is washed with 10 ml of brine, dried over MgSO$_4$ and evaporated under reduced pressure to give the crude product (44 mg) which was used without further purification fir the next step.

MS (ESI): 862.2 ([MH]$^+$)

B] Preparation of compound of formula XXVI where R1 is [(4-methoxyphenyl)methyl]thio and R2b and R2c taken together form a morpholine ring (including the nitrogen to which they are attached), $Rp_1$ is acetyl and R14 is methyl 54 mg (0.06 mmol) of compound of example 19, step A is dissolved in 4 ml acetonitrile and 54.6 mg (0.63 mmol) morpholine is added. The reaction mixture is stirred at room temperature for 24 hours. The solvent is evaporated under reduced pressure and dried in vacuo. The crude product is used without further purification for the next step.

MS (ESI): 949.3 ([MH]$^+$), 475.2 ([M+2H]$^{++}$)

C] Preparation of compound of formula I where R1 is [2-[5-(3,5-dichloropyridine-4-yl-aminocarbonyl)-2-methoxy-phenoxy]ethyl]thio, R2 is 3-(4-morpholinyl)-1-oxopropoxy, R3 and R4 are hydrogen, R12 and R13 taken together form a C=O group and R14 is methyl (I-19).

The title compound is prepared from 3-(2-chloro-ethoxy)-N-(3,5-dichloro-pyridin-4-yl)-4-methoxy-benzamide (example 18, step B) and compound of example 19, step B following the procedures described in example 15, steps C and D.

MS (ESI): 1125.5 ([MH]$^+$), 563.5 ([M+2H]$^{++}$)
Ret. Time (System Ca): 28.0 min

B. BIOLOGICAL ACTIVITY

The compounds of the invention exhibit substantial inhibitory activity towards human phosphodiesterases (PDEs), in particular towards PDE4. The following assay has been used to determine the inhibitory activity of the compounds.

Assay

PDE4 specifically hydrolyzes cAMP and releases the product AMP. The potency of PDE inhibition by said agents is determined in an in vitro enzymatic assay. The assay is commercially available (IMAP™ FP assay Molecular Devices Corp.(MDS)) and is optimized for the use of human PDE4. Fluorescently labeled cAMP is hydrolyzed by PDE4 and in a second step, binding of labeled product to a large binding partner allowed product detection by fluorescence polarization (FP) measurements.

PDE4 is partially purified from undifferentiated human monocytic cells (U-937) according to Thorpy et al. 1992 (J. Pharmacol. Exp. Ther. 263: 1195). Final preparations are specific for cAMP and did not hydrolyze cGMP above the detection limit of the assay. In addition, PDE4 preparations are validated by inhibition studies with PDE4-specific and unspecific PDE inhibitors.

Stock solutions of test compounds are made in DMSO and diluted in assay buffer (10 mM Tris-HCl, 10 mM $MgCl_2$, 0.1% BSA 0.05% $NaN_3$, pH 7.2) to the desired concentrations. The solutions used in the assay contained test compound in assay buffer with 2% DMSO.

10 µl of substrate (at a concentration recommended by the manufacturer) are mixed with 5 µl of appropriately diluted PDE and 5 µl of test compound solution. 5 µl of reaction buffer with 2% DMSO are used for control reactions. The final concentration of DMSO in the assay is 0.5%, which did not significantly alter the PDE activity. After incubation for 90 minutes at room temperature, 60 µl of binding reagent are added as specified by the manufacturer. Binding is allowed to proceed for 30 minutes and fluorescence polarization is measured. Dose dependence of PDE inhibition is measured by assaying dilution series of test compounds in duplicates. $IC_{50}$ values are determined from the measured activities by curve fitting.

Results

| Example | $IC_{50}$ (PDE4) [µM] |
|---|---|
| 1 | 13.4 |
| 2 | 3.9 |
| 3 | 3.4 |
| 4 | 0.28 |
| 5 | 0.85 |
| 6 | 0.37 |
| 7 | 7.6 |
| 8 | 4.7 |
| 9 | 24.2 |
| 10 | 1.0 |
| 11 | 0.008 |
| 12 | 3.8 |
| 13 | 2.6 |
| 14 | 0.0049 |
| 15 | 0.48 |
| 16 | 0.11 |

The PDE4-inhibiting activity found for the compounds of this invention as shown in the examples is particularly surprising because the basic macrolide of the exemplified compounds which has the following formula:

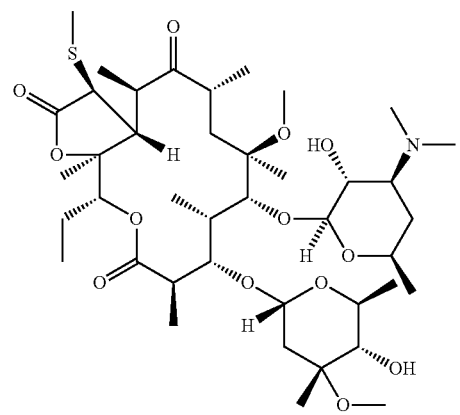 [SMILES: CC[C@H]1OC(=O)[C@H](C)[C@@H](O[C@H]2C[C@@](C)(OC)[C@@H](O)[C@H](C)O2)[C@H](C)[C@@H](O[C@@H]2O[C@H](C)C[C@H](N(C)C)[C@H]2O)[C@](C)(OC)C[C@@H](C)C(=O)[C@H](C)[C@H]2[C@H](SC)C(=O)O[C@@]21C]

does not show any PDE4-inhibiting activity up to a concentration of 50 µM in the assay used in the examples and, even if the substituent linked to said basic macrolide in one of the compounds of the present invention when used in free form shows a certain PDE4-inhibiting activity in said assay like, for example, the following compound

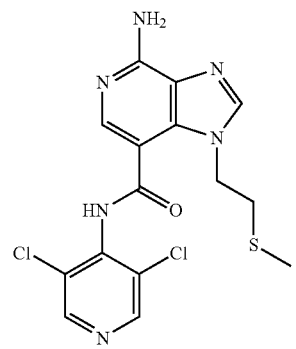 [SMILES: CSCCn1cnc2c(N)ncc(C(=O)Nc3c(Cl)cncc3Cl)c21]

which has a value for $IC_{50}$(PDE4) of 3.6 µM, the PDE4-inhibiting activity of the respective compound according to the present invention wherein the very same compounds are linked together to form a molecule of formula (I-A), generally show a PDE4-inhibiting activity which is strongly improved over the corresponding activity of its partial components as well as over the activity to be reasonably expected for a mixture of said partial components. In the present case, for example, an $IC_{50}$(PDE4) of 0.008 µM is found for the compound of Example 11 having the formula:

which is only about one fivehundredth of the $IC_{50}$(PDE4) for the macrolide substituent in free form.

The invention claimed is:

1. A macrolide compound of formula (I)

wherein

R1 is a residue —Y—X-Q;

Y is S, SO or $SO_2$;

X is a bond or a linear group consisting of hydrogen atoms and 1 to 9 atoms, each selected from the group consisting of C, N, O and S, of which up to 2 atoms can be N and one atom can be O or S, one carbon atom can appear as a CO group and the sulphur atom can appear as an $SO_2$ group and two adjacent C atoms can be present as —CH=CH— or —C≡C— and which group X is unsubstituted or is substituted with —COO—W or —CONH—W;

Q is a residue —V-A1-L-A2-W or, if X does not represent a bond, may also be —NR6R7;

V is a divalent aromatic or heterocyclic group, optionally substituted with $C_1$-$C_4$alkyl, $C_1$-$C_4$alkoxy, $C_3$-$C_7$cycloalkyloxy, $C_3$-$C_7$cycloalkyl—$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-$C_4$)alkylamino, $C_1$-$C_4$alkylthio, mercapto, hydroxy, carbamoyl, a carboxyl group, an oxo group, aryl or heterocyclyl, wherein said aryl or heterocyclyl may be unsubstituted or substituted with one or more of the above identified substituents other than aryl or heterocyclyl;

W is aryl or heterocyclyl optionally substituted with $C_1$-$C_4$alkyl, $C_1$-$C_4$alkoxy, $C_3$-$C_7$cycloalkyloxy, $C_3$-$C_7$cycloalkyl—$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, or an oxo group;

A1 and A2 are, independently of each other, either absent or a $C_1$-$C_4$alkylene group;

L is —O—, —S—, —$SO_2$—, —NH—, —CO—, —(CO)O—, —O(OC)—, —(CO)NH—, —NH(CO)—, —($SO_2$)NH—, —HN($SO_2$)—, —HN(CO)NH—, —O(CO)NH—, —HN(CO)O—, or can also be absent if A1 and/or A2 are present;

R2 is OR2a and

R3 is hydrogen or

R2 and R3 taken together with the carbon atom to which they are linked, represent a C=O group;

R2a is hydrogen, acetyl, —(C=O)CH2NR2bR2c, or —(C=O)CH2CH2NR2bR2c;

R2b and R2c are, independently of each other, hydrogen or C1-C6 alkyl which can be unsubstituted or substituted with $C_1$-$C_4$alkoxy, $C_3$-$C_7$cycloalkyloxy or $C_3$-$C_7$cycloalkyl-$C_1$-$C_4$alkoxy, halogen, halogen substituted alkyl groups, cyano, nitro, amino, alkylamino, dialkylamino, alkylthio, mercapto, hydroxy, carbamoyl, carboxyl, or oxo, and wherein said $C_1$-$C_6$ alkyl group can contain additionally up to two atoms can be N, O or S and one carbon atom can be as C=O or taken together with the nitrogen atom to which they are linked form a 4-7 membered-ring of which up to two atoms can be N, O or S and one carbon can be as C=O;

R4 is hydrogen;

R6 and R7 are independently of each other, hydrogen, methyl; or groups selected from the group consisting of aryl; aralkyl; heterocyclyl and heterocyclylalkyl, which groups are optionally substituted with $C_1$-$C_6$alkyl, $C_1$-$C_4$alkoxy, $C_3$-$C_7$cycloalkyloxy or $C_3$-$C_7$ cycloalkyl-$C_1$-$C_4$alkoxy, halogen, halogen substituted alkyl groups, halogen substituted alkoxy groups, nitro, amino, alkylamino, dialkylamino, alkylthio, mercapto, hydroxy, carbamoyl, carboxyl and oxo; and one of R6 and R7 can also be a group -L-A2-W;

R12 is hydrogen and

R13 is OR14 or

R12 and R13, taken together with the carbon atom to which they are linked, represent a C=O group;

R14 is, independently at each occurrence in formula I, hydrogen or a saturated or unsaturated aliphatic group with 1 to 6 carbon atoms; and

* indicates a chiral centre which is in the (R) or (S) form.

2. A compound of formula (I) according to claim 1 wherein R2a is hydrogen.

3. A compound of formula (I) according to claim 1 wherein R2 and R3, taken together with the carbon atom to which they are linked, represent a C=O group.

4. A compound according to claim 1 wherein R13 is hydroxyl or allyloxy.

5. A compound according to claim 1 wherein R12 and R13 taken together with the carbon atom to which they are linked, represent a C=O group.

6. A compound according to claim 5 wherein R14 represents hydrogen or methyl.

7. A compound according to claim 6 wherein OR14 in position 6 of the macrolide ring represents methoxy.

8. A compound according to claim 7 wherein Y is $SO_2$ or S.

9. A compound according to claim 8 wherein Q is a residue —V-A1-L-A2-W.

10. A compound according to claim 9 wherein V is a divalent group of formula

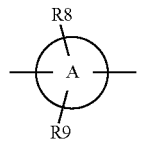

wherein

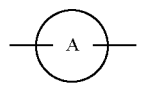

is a phenylene ring or a x-membered saturated or unsaturated divalent heterocyclo-aliphatic or heteroaromatic ring containing from 2 to (x-1) carbon atoms with x being 5 or 6, and from 1 to 4 hetero atoms selected from the group consisting of sulfur, and preferably oxygen and nitrogen, R8 and R9 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-C4)alkylamino, $C_1$-$C_4$alkylthio, mercapto, hydroxy, carbamoyl, a carboxyl group, an oxo group; or aryl or heterocyclyl, which may be unsubstituted or substituted with one or more of the above identified substituents other than aryl or heterocyclyl, or when both substituents R8 and R9 are located at adjacent carbon atoms of the ring

, these two substituents, taken together with said adjacent carbon atoms, can also form a 5- or 6-membered aromatic or a x-membered saturated or unsaturated heterocycloaliphatic or heteroaromatic ring containing from 2 to (x-1) carbon atoms with x being 5 or 6, and from 1 to 4 hetero atoms selected from the group consisting of sulfur and preferably, oxygen and nitrogen, and wherein V can have all together one to four substituents of the kind as defined for R8 and R9 and the free valences can be located either on one or on both rings of the group V.

11. A compound according to claim 10 wherein V is a divalent group of formula

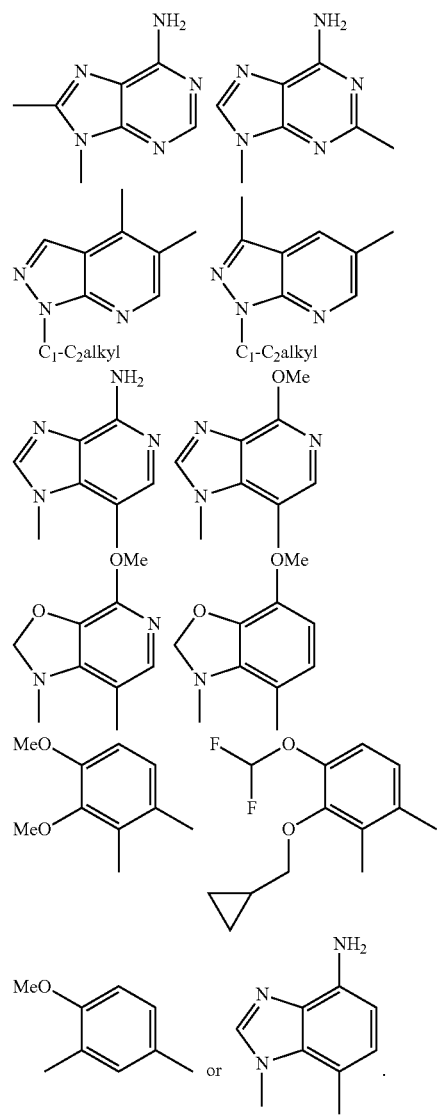

12. A compound according to claim 11 wherein W is heterocyclyl.

13. A compound according to claim 12 wherein W is a group of formula

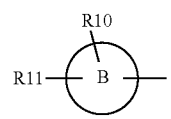

wherein

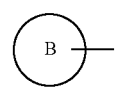

is a phenyl ring or a x-membered saturated or unsaturated heterocycloaliphatic or heteroaromatic ring containing from 2 to (x-1) carbon atoms with x being 5 or 6, and from 1 to 4 hetero atoms selected from the group consisting of sulfur, and preferably oxygen and nitrogen, R10 and R11 are independently selected from the group consisting of hydrogen, $C_1$-$C_4$alkyl, $C_1$-$C_4$alkoxy, $C_3$-$C_7$cycloalkyloxy, $C_3$-$C_7$cycloalkyl-$C_1$-$C_4$alkoxy, halogen, halogen-substituted $C_1$-$C_4$alkyl groups, halogen substituted $C_1$-$C_4$alkoxy groups, cyano, nitro, amino, $C_1$-$C_4$alkylamino, di($C_1$-C4) alkylamino, $C_1$-$C_4$alkylthio, mercapto, hydroxy, carbamoyl, a carboxyl group, and an oxo group; or when both substituents R10 and R11 are located at adjacent carbon atoms of the ring

, these two substituents, taken together with said adjacent carbon atoms, can also form a 5- or 6-membered aromatic or a x-membered saturated or unsaturated heterocycloaliphatic or heteroaromatic ring containing from 2 to (x-1) carbon atoms with x being 5 or 6, and from 1 to 3 hetero atoms selected from the group consisting of sulfur, oxygen and nitrogen, wherein W can have all together one to four substituents of the kind as defined for R10 and R11 and the free valence can be located on either ring of the group W.

14. The compound of claim 13 wherein
W is a group of one of the formulae

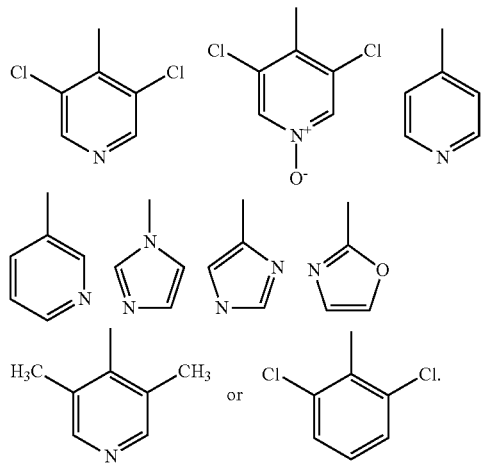

15. A compound according to claim 8 wherein
Q is —NR6R7.

16. A compound according to claim 14 wherein
A1, A2 are independently of each other either absent or a $C_1$-$C_2$alkylene group; and
L is —NH—, —(CO)NH— or —NH(CO)— or is absent.

17. A compound according to claim 14 wherein
A1, A2 are independently of each other either absent or a $C_1$-$C_2$alkylene group;
L is —NH—, —(CO)NH— or —NH(CO)—;

V is a divalent group of formula

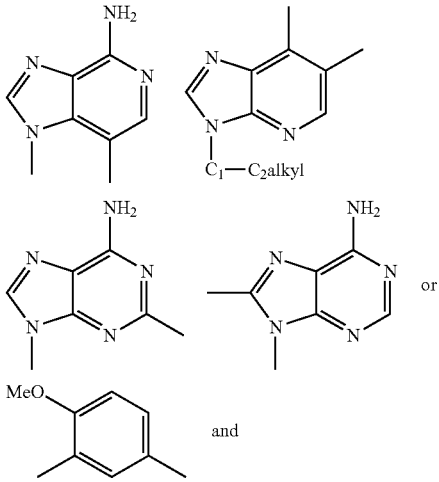

W is a group of formula

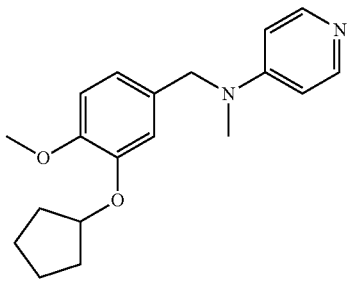

18. A compound according to claim 17 wherein
Y is —S— and
X is —CH$_2$-CH$_2$—NH— or —CH$_2$—CH$_2$—O— which are linked to residue Q via the NH group or the oxygen atom respectively, or —CH$_2$—CH$_2$—.

19. A compound according to claim 18 wherein —NR6R7 is a group of one of the following formulae

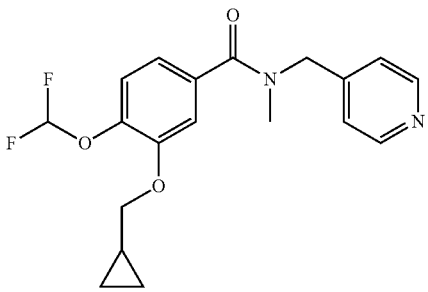

101
-continued
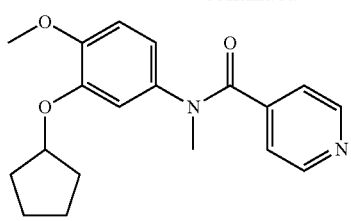
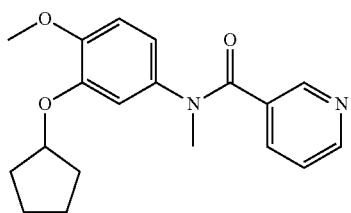
or
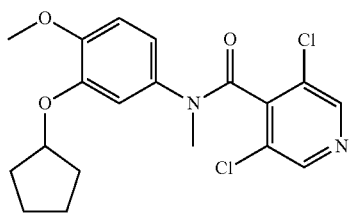
wherein
means a methoxy residue.
20. A compound according to claim 1 wherein said compound has one of the following formulae:
102
-continued
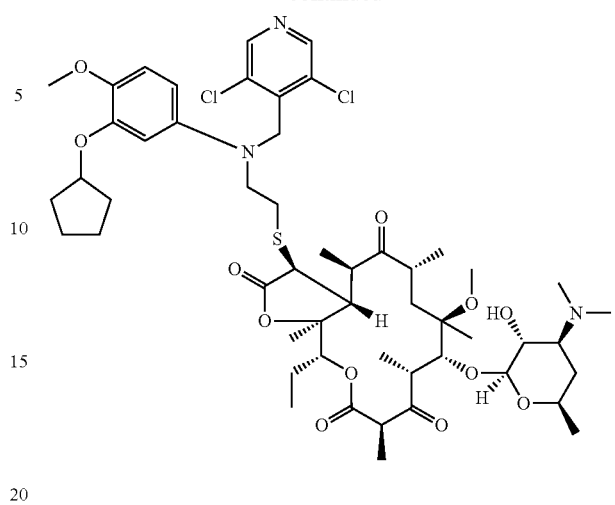
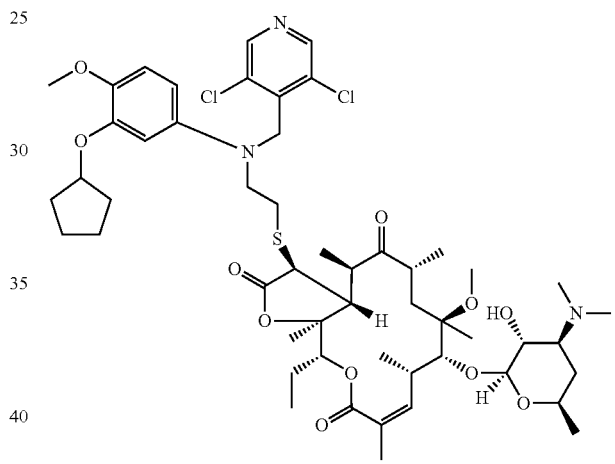
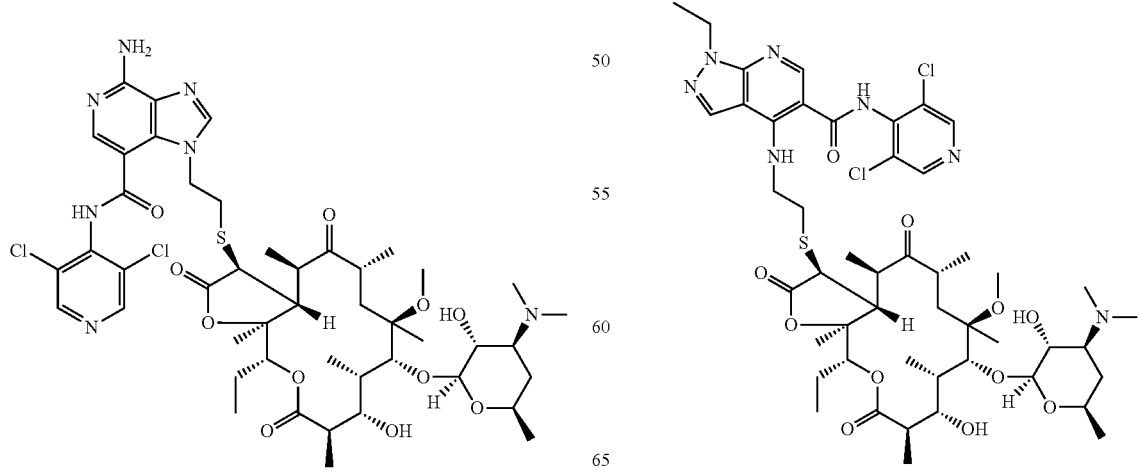

103
-continued

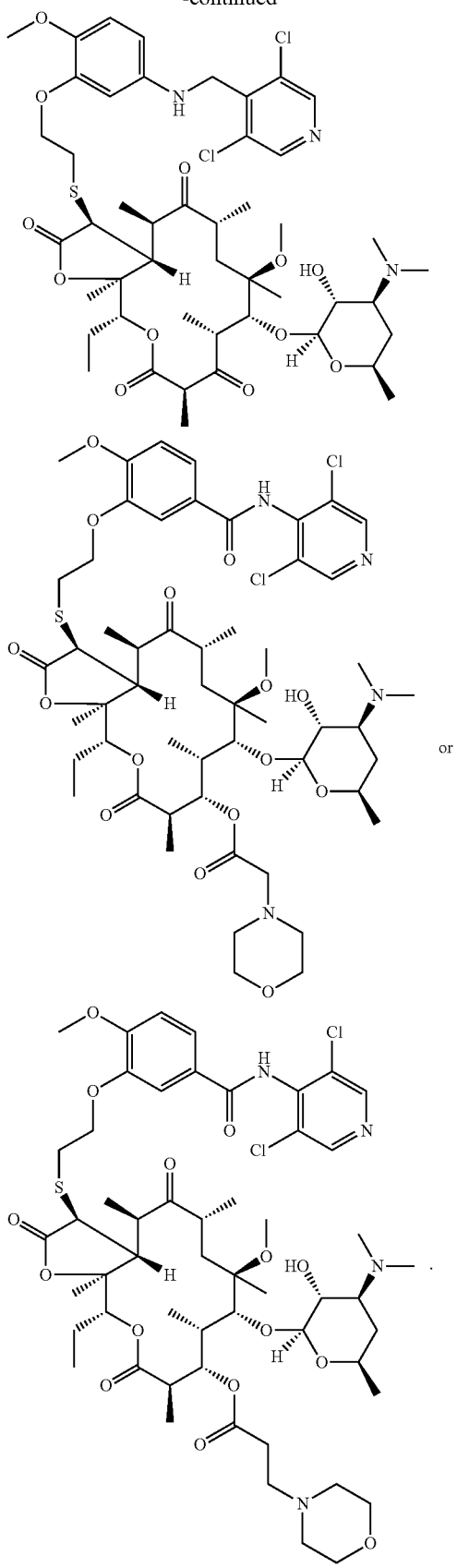

or

21. The compound of formula:

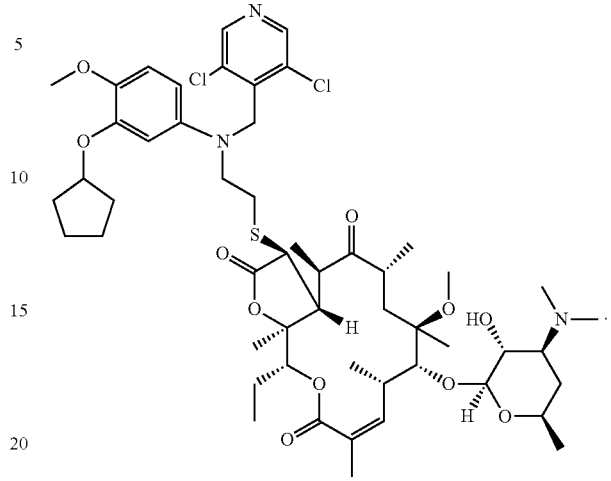

22. The compound of formula I of claim 1, wherein R2a and R4 are hydrogen.

23. The compound of claim 2 wherein R4 is hydrogen.

24. The compound of claim 13 wherein X is oxygen or nitrogen.

25. A method for treating cancer in a subject which is an animal or a human comprising administering to said subject in need thereof an effective amount of a macrolide compound of formula (I-A):

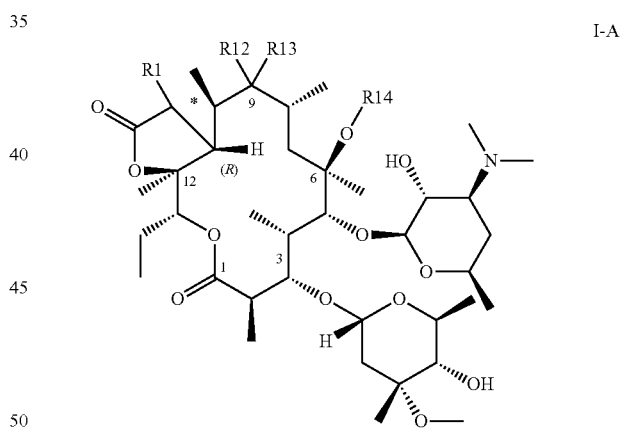

wherein

R1 is a residue —Y—X-Q;

Y is S, SO or $SO_2$;

X is a bond or a linear group consisting of hydrogen atoms and with up to 9 atoms, each selected from the group consisting of C, N, O and S, of which up to 2 atoms can be N and one atom can be O or S, one carbon atom can appear as a CO group and the sulphur atom can appear as an $SO_2$ group and two adjacent C atoms can be present as —CH=CH— or —C≡C— and which group X is unsubstituted or is substituted with —COO—W or —CONH—W;

Q is a residue —V-A1-L-A2-W or, if X does not represent a bond, may also be —NR6R7;

V is a divalent aromatic or heterocyclic group;

W is aryl or heterocyclyl; or in a group —V-A1-L-A2-W, wherein at least one of the groups A1; L or A2 is present, can also be a monovalent substituted or unsubstituted, saturated or unsaturated linear group with up to 5 atoms consisting of C, N, O and/or S of which one carbon can appear as a CO group one sulphur atom can appear as an SO$_2$ group, A1 and A2 are independently of each other either absent or a C$_1$-C$_4$alkylene group;

L is a single bond, —O—, —S—, —SO$_2$—, —NH—, —CO—, —(CO)O—, —O(OC)—, —(CO)NH—, —NH(CO)—, —(SO$_2$)NH—, —HN(SO$_2$)—, —HN(CO)NH—, —O(CO)NH—, —NH(CO)O—, or can also be absent if A1 and/or A2 are present;

R6, R7 are independently of each other selected from aryl; aralkyl; heterocyclyl and heterocyclylalkyl; and one of R6 and R7 can also be a group -L-W R12 is hydrogen and R13 is OR14 or R12 and R13 taken together with the carbon atom to which they are linked, represent a C=O group;

R14 is, independently at each occurrence in formula (I-A), hydrogen or a saturated or unsaturated aliphatic group with 1 to 6 carbon atoms; and

* indicates a chiral centre which is in the (R) or (S) form.

26. The method of claim 25 wherein said compound has one of the following formulae:

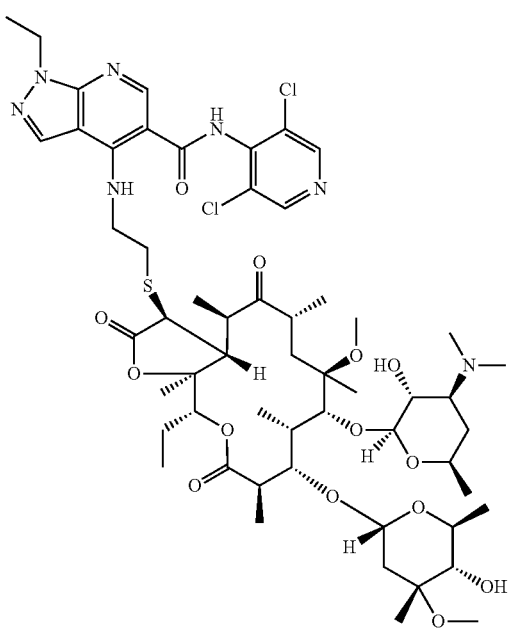

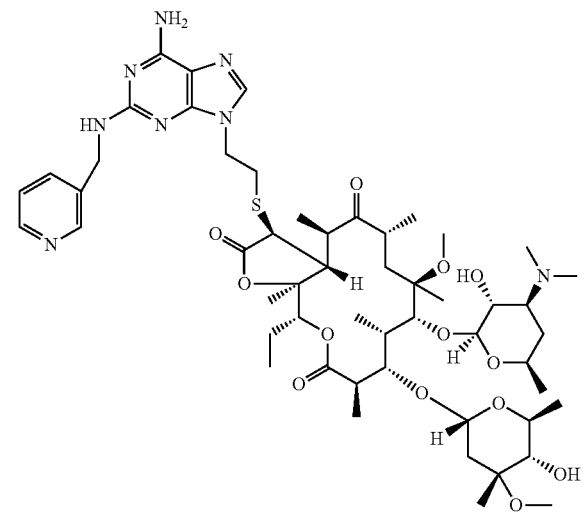

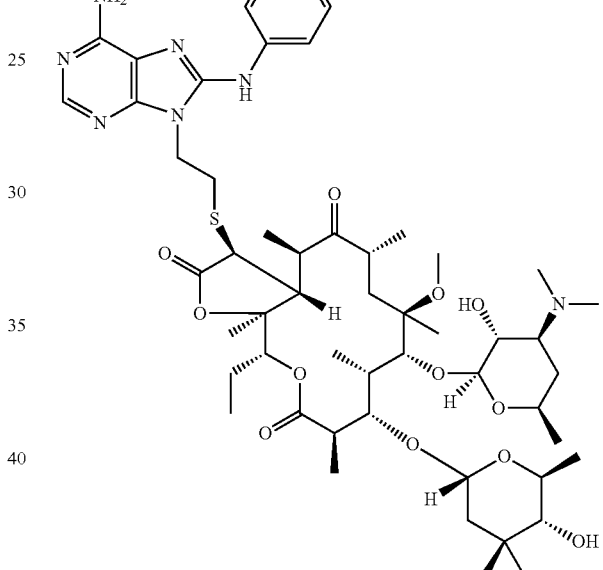

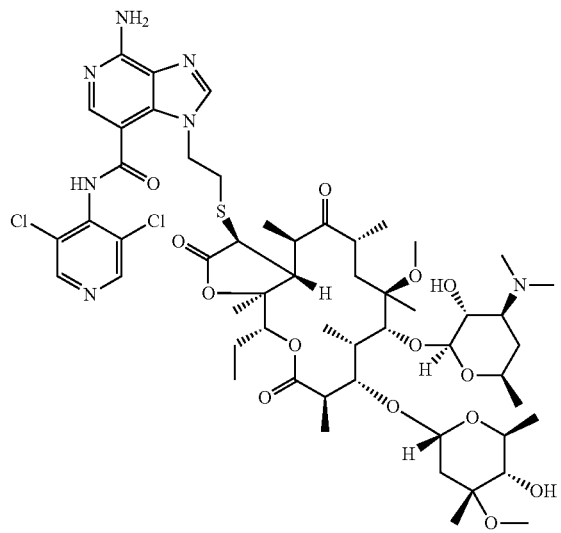

107
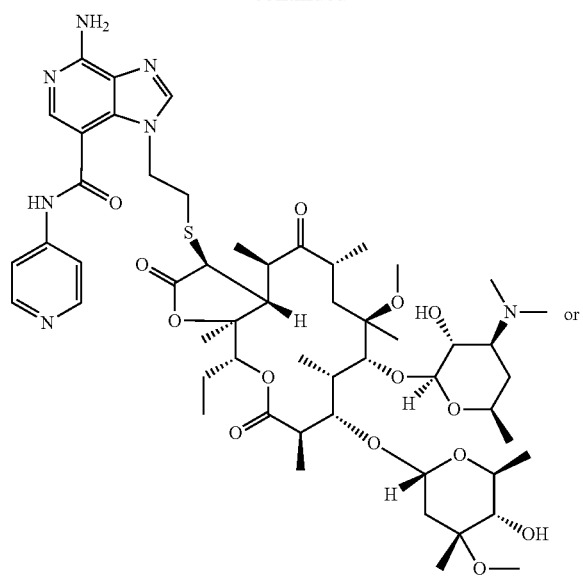
or
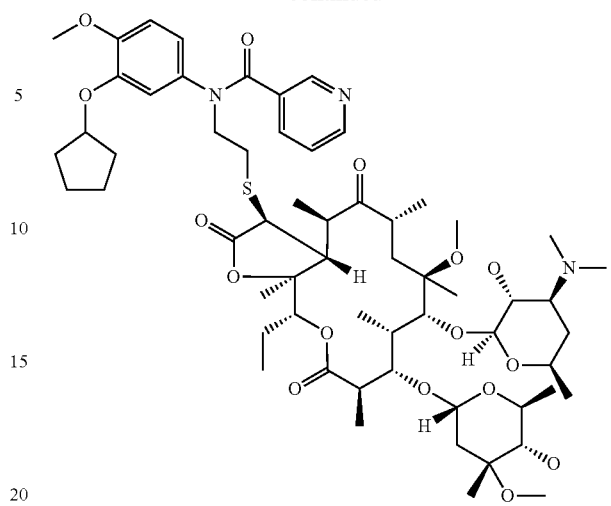
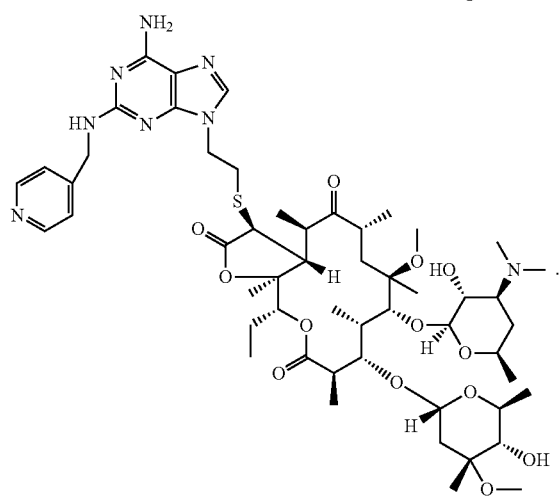
.
27. The method of claim 25 wherein said compound has one of the following formulae:
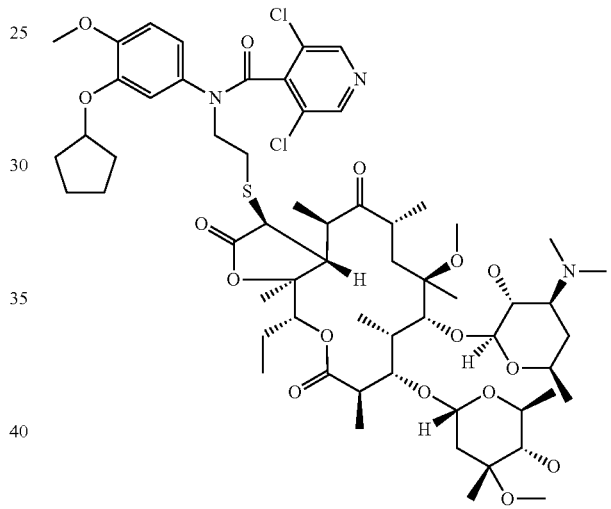
108
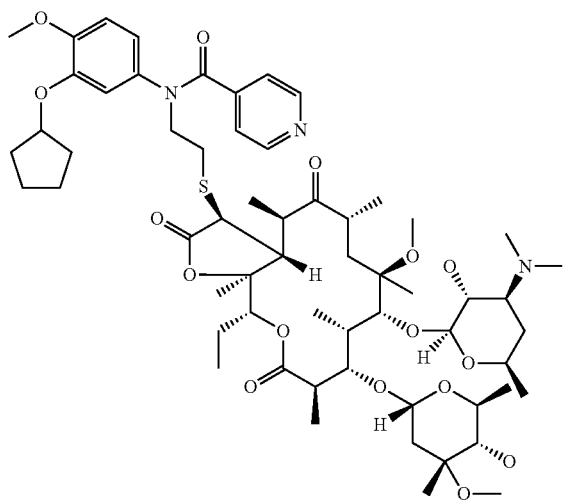
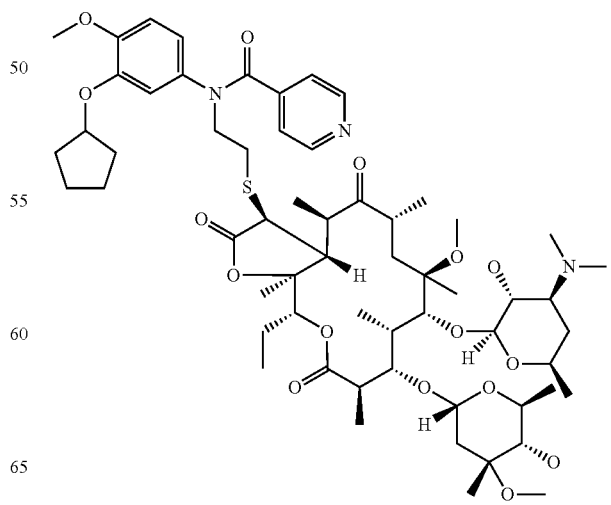

109
-continued
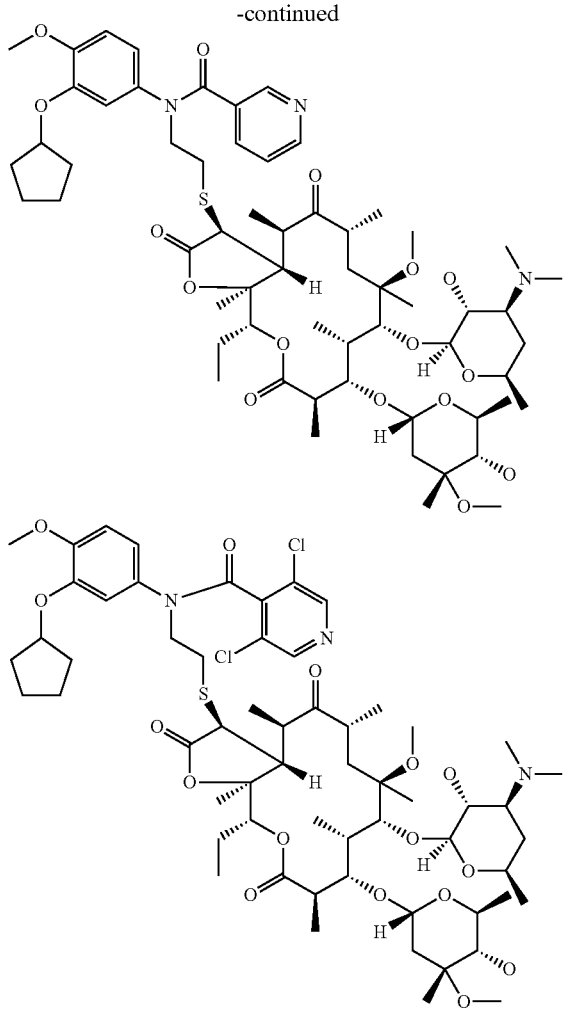
110
-continued
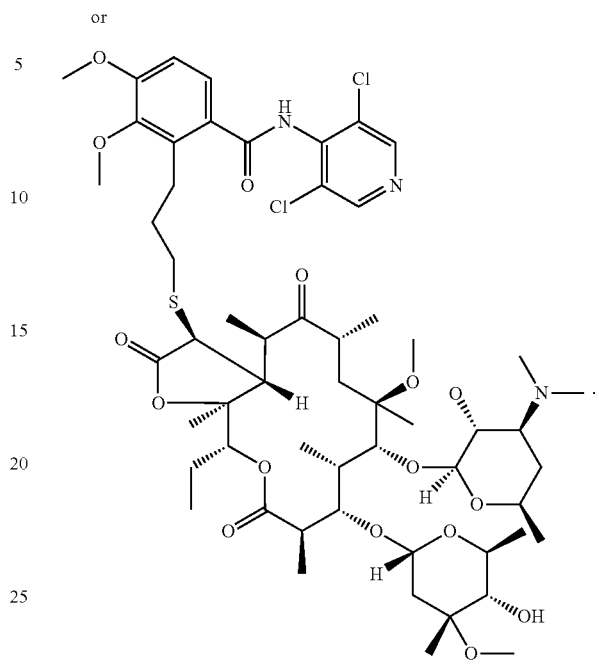
or
28. A pharmaceutical composition comprising a compound of claim 1 and a pharmaceutically acceptable carrier.
* * * * *